(12) United States Patent
Kalina, Jr. et al.

(10) Patent No.: US 12,279,822 B2
(45) Date of Patent: *Apr. 22, 2025

(54) GONIOSCOPIC DEVICES

(71) Applicant: GLAUKOS CORPORATION, San Clemente, CA (US)

(72) Inventors: Charles Raymond Kalina, Jr., Irvine, CA (US); Thomas W. Burns, Dana Point, CA (US); Chris Calcaterra, Coto De Caza, CA (US); Edward Collins, Laguna Niguel, CA (US); Timothy McCauley, Oceanside, CA (US); David S. Haffner, Mission Viejo, CA (US); Steven M. Henderson, Roswell, GA (US)

(73) Assignee: GLAUKOS CORPORATION, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/494,617

(22) Filed: Oct. 25, 2023

(65) Prior Publication Data

US 2024/0245294 A1 Jul. 25, 2024

Related U.S. Application Data

(63) Continuation of application No. 17/332,885, filed on May 27, 2021, now Pat. No. 11,826,104, which is a
(Continued)

(51) Int. Cl.
*A61B 3/00* (2006.01)
*A61B 3/117* (2006.01)

(52) U.S. Cl.
CPC ............ *A61B 3/117* (2013.01); *A61B 3/0033* (2013.01); *A61B 3/0083* (2013.01)

(58) Field of Classification Search
CPC ..... A61B 3/117; A61B 3/0033; A61B 3/0083; A61B 3/0091; A61B 3/1225; A61B 3/1233; A61B 3/1241; G02B 5/0808; G02B 7/002
(Continued)

(56) References Cited

U.S. PATENT DOCUMENTS

| 2,430,851 A | 11/1947 | Allen |
| D166,597 S | 4/1952 | Filsinger |

(Continued)

FOREIGN PATENT DOCUMENTS

| EP | 4282390 | 2/2024 |
| WO | WO 1994/010900 | 5/1994 |

(Continued)

OTHER PUBLICATIONS

Bahler et al., "Trabecular Bypass Stents Decrease Intraocular Pressure in Cultured Human Anterior Segments", American Journal of Ophthalmology, Dec. 2004, vol. 138, pp. 988-994.
(Continued)

*Primary Examiner* — Henry Duong
(74) *Attorney, Agent, or Firm* — Knobbe, Martens, Olson & Bear, LLP

(57) ABSTRACT

A gonioscopic attachment can attach to a gonioscope and can include atraumatic retention elements that are configured to engage an eye to retain the gonioscope relative to the eye. The gonioscopic attachment can be configured to position the gonioscope so that at least a portion of the concave distal surface of the gonioscopic optical element is spaced apart from the eye, and/or so that the curvature of the distal surface is angularly offset from the curvature of the eye. The gonioscope can include a fixation point configured to be visible to the subject when the gonioscope is positioned on the eye. In some embodiments, the retention elements can be
(Continued)

incorporated directly into the gonioscope. A coupling mechanism can couple the gonioscope to a lid speculum. The gonioscope can include a light pipe, which can be configured to directly light into the eye.

20 Claims, 26 Drawing Sheets

Related U.S. Application Data continuation of application No. 16/706,525, filed on Dec. 6, 2019, now Pat. No. 11,019,996, which is a continuation of application No. 15/559,391, filed as application No. PCT/US2016/023296 on Mar. 18, 2016, now Pat. No. 10,499,809.

(60) Provisional application No. 62/202,017, filed on Aug. 6, 2015, provisional application No. 62/136,376, filed on Mar. 20, 2015.

(58) Field of Classification Search
USPC .......................................................... 351/221
See application file for complete search history.

(56) References Cited

U.S. PATENT DOCUMENTS

| | | |
|---|---|---|
| D166,842 S | 5/1952 | Armbruster |
| D175,322 S | 8/1955 | Stegeman |
| D196,610 S | 10/1963 | Kolbeck et al. |
| 3,112,570 A | 12/1963 | Vasconcellos |
| D205,094 S | 6/1966 | Pulos et al. |
| D207,371 S | 4/1967 | Pulos |
| 3,469,903 A | 9/1969 | Grichnik et al. |
| D217,515 S | 5/1970 | Wells et al. |
| D217,516 S | 5/1970 | Wells et al. |
| 3,589,800 A | 6/1971 | Cardona |
| 3,753,611 A | 8/1973 | Ebbesen |
| 3,820,879 A | 6/1974 | Frisen |
| 4,007,980 A | 2/1977 | Bracher et al. |
| 4,033,679 A | 7/1977 | Sussman |
| 4,067,646 A | 1/1978 | Nohda |
| 4,134,647 A | 1/1979 | Ramos-Caldera |
| 4,134,667 A | 1/1979 | Schnall et al. |
| 4,205,747 A | 6/1980 | Gilliam et al. |
| 4,269,307 A | 5/1981 | LaHaye |
| 4,307,944 A | 12/1981 | Schirmer |
| 4,439,026 A | 3/1984 | Wilms |
| 4,469,413 A | 9/1984 | Shirayanagi |
| 4,568,157 A | 2/1986 | Kurwa |
| 4,598,984 A | 7/1986 | Rol |
| 4,627,694 A | 12/1986 | Volk |
| 4,664,490 A | 5/1987 | Rol |
| 4,682,866 A | 7/1987 | Volk |
| 4,721,378 A | 1/1988 | Volk |
| 4,728,183 A | 3/1988 | Heacock et al. |
| 4,736,836 A | 4/1988 | Alongi et al. |
| 4,738,521 A | 4/1988 | Volk |
| 4,799,784 A | 1/1989 | Safir |
| 4,907,872 A | 3/1990 | Schirmer et al. |
| 5,007,729 A | 4/1991 | Erickson |
| 5,024,518 A | 6/1991 | Richards et al. |
| 5,046,836 A | 9/1991 | Volk |
| 5,200,773 A | 4/1993 | Volk |
| 5,216,456 A | 6/1993 | Volk |
| 5,260,578 A | 11/1993 | Bliton et al. |
| 5,281,227 A | 1/1994 | Sussman |
| D345,213 S | 3/1994 | Shalon et al. |
| 5,309,187 A | 5/1994 | Crossman et al. |
| 5,359,372 A | 10/1994 | Kida et al. |
| 5,412,441 A | 5/1995 | Tibbling et al. |
| 5,424,789 A | 6/1995 | Volk |
| 5,472,440 A | 12/1995 | Beckman |
| 5,479,222 A | 12/1995 | Volk |
| 5,501,217 A | 3/1996 | Ishiguro et al. |
| 5,535,060 A | 7/1996 | Grinblat |
| 5,537,164 A | 7/1996 | Smith |
| 5,548,352 A | 8/1996 | Dewey |
| 5,601,549 A | 2/1997 | Miyagi |
| D379,514 S | 5/1997 | Laun et al. |
| D394,704 S | 5/1998 | Koepnick |
| 5,784,147 A | 7/1998 | Volk |
| 5,805,269 A | 9/1998 | Volk |
| 5,822,036 A | 10/1998 | Massie et al. |
| 5,830,139 A | 11/1998 | Abrue |
| 5,886,822 A | 3/1999 | Spitzer |
| 5,903,333 A | 5/1999 | Siminou et al. |
| 5,963,301 A | 10/1999 | Volk |
| 6,059,772 A | 5/2000 | Hsia et al. |
| 6,164,779 A | 12/2000 | Volk |
| 6,183,085 B1 | 2/2001 | Roggy et al. |
| 6,196,686 B1 | 3/2001 | Reiner |
| D444,236 S | 6/2001 | Koop et al. |
| 6,266,182 B1 | 7/2001 | Morita |
| 6,450,984 B1 | 9/2002 | Lynch et al. |
| 6,464,724 B1 | 10/2002 | Lynch et al. |
| 6,524,275 B1 | 2/2003 | Lynch et al. |
| 6,569,199 B1 | 5/2003 | Dotan et al. |
| 6,596,026 B1 | 7/2003 | Gross et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,698,886 B2 | 3/2004 | Pollack et al. |
| D489,130 S | 4/2004 | Sinding |
| D490,152 S | 5/2004 | Myall et al. |
| 6,730,056 B1 | 5/2004 | Ghaem et al. |
| 6,736,791 B1 | 5/2004 | Tu et al. |
| 6,767,098 B2 | 7/2004 | Erickson et al. |
| D493,887 S | 8/2004 | Roberts et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,939,298 B2 | 9/2005 | Brown et al. |
| 6,942,343 B2 | 9/2005 | Farberov |
| 6,955,656 B2 | 10/2005 | Bergheim et al. |
| 6,976,758 B2 | 12/2005 | Khaw et al. |
| 6,981,958 B1 | 1/2006 | Gharib et al. |
| D523,881 S | 6/2006 | Edwards et al. |
| 7,072,104 B2 | 7/2006 | Okamura et al. |
| 7,094,225 B2 | 8/2006 | Tu et al. |
| 7,125,119 B2 | 10/2006 | Farberov |
| 7,135,009 B2 | 11/2006 | Tu et al. |
| D534,194 S | 12/2006 | Hines et al. |
| 7,144,111 B1 | 12/2006 | Ross, III et al. |
| 7,148,970 B2 | 12/2006 | de Boer |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,220,238 B2 | 5/2007 | Lynch et al. |
| D547,450 S | 7/2007 | Hurlstone et al. |
| 7,244,024 B2 | 7/2007 | Biscardi |
| D549,326 S | 8/2007 | Aparici et al. |
| 7,261,687 B2 | 8/2007 | Yang |
| 7,273,475 B2 | 9/2007 | Tu et al. |
| 7,297,130 B2 | 11/2007 | Bergheim et al. |
| 7,357,504 B2 | 4/2008 | Fischer |
| 7,393,104 B2 | 7/2008 | Hara et al. |
| D574,867 S | 8/2008 | Lewis |
| 7,419,262 B2 | 9/2008 | Whalen |
| 7,431,710 B2 | 10/2008 | Tu et al. |
| 7,438,413 B2 | 10/2008 | Kashiwagi et al. |
| 7,447,408 B2 | 11/2008 | Bouma et al. |
| 7,448,752 B2 | 11/2008 | Levine |
| 7,480,058 B2 | 1/2009 | Zhao et al. |
| 7,488,303 B1 | 2/2009 | Haffner et al. |
| 7,494,220 B2 | 2/2009 | Copland |
| 7,501,645 B2 | 3/2009 | Shaver |
| 7,503,605 B2 | 3/2009 | Mears |
| 7,512,436 B2 | 3/2009 | Petty et al. |
| 7,520,611 B2 | 4/2009 | Franz et al. |
| 7,524,064 B2 | 4/2009 | Wyatt |
| 7,549,744 B2 | 6/2009 | Bradley |

(56) References Cited

U.S. PATENT DOCUMENTS

| | | |
|---|---|---|
| 7,563,241 B2 | 7/2009 | Tu et al. |
| 7,575,321 B2 | 8/2009 | Newman et al. |
| 7,614,747 B2 | 11/2009 | Foster |
| 7,618,372 B2 | 11/2009 | dela Houssaye |
| 7,678,065 B2 | 3/2010 | Haffner et al. |
| D613,402 S | 4/2010 | Roberts et al. |
| 7,708,403 B2 | 5/2010 | Newman |
| 7,708,711 B2 | 5/2010 | Tu et al. |
| 7,748,846 B2 | 7/2010 | Todd |
| 7,758,190 B2 | 7/2010 | Korb et al. |
| 7,766,480 B1 | 8/2010 | Graham et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,884,945 B2 | 2/2011 | Srinivasan et al. |
| D635,257 S | 3/2011 | Ellman |
| 7,925,133 B2 | 4/2011 | Bouma et al. |
| 7,951,155 B2 | 5/2011 | Smedley et al. |
| 7,954,947 B2 | 6/2011 | Sugita et al. |
| 7,963,654 B2 | 6/2011 | Aggarwala |
| 7,971,998 B2 | 7/2011 | Lesk et al. |
| 8,007,459 B2 | 8/2011 | Haffner et al. |
| D645,489 S | 9/2011 | Gille et al. |
| D645,490 S | 9/2011 | Gille et al. |
| 8,011,504 B1 | 9/2011 | Farberov |
| 8,062,244 B2 | 11/2011 | Tu et al. |
| 8,070,289 B2 | 12/2011 | Peyman |
| 8,070,290 B2 | 12/2011 | Gille et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,152,752 B2 | 4/2012 | Lynch et al. |
| 8,226,236 B2 | 7/2012 | Williams et al. |
| 8,273,050 B2 | 9/2012 | Bergheim et al. |
| 8,333,742 B2 | 12/2012 | Bergheim et al. |
| 8,337,445 B2 | 12/2012 | Tu et al. |
| 8,348,877 B2 | 1/2013 | Tu et al. |
| 8,369,669 B2 | 2/2013 | Bouma et al. |
| 8,388,568 B2 | 3/2013 | Lynch et al. |
| 8,506,515 B2 | 8/2013 | Burns et al. |
| 8,579,846 B2 | 11/2013 | Tu et al. |
| 8,617,094 B2 | 12/2013 | Smedley et al. |
| 8,771,217 B2 | 7/2014 | Lynch et al. |
| 8,801,648 B2 | 8/2014 | Bergheim et al. |
| 8,808,219 B2 | 8/2014 | Bergheim et al. |
| 8,814,820 B2 | 8/2014 | Bergheim et al. |
| 8,851,676 B2 | 10/2014 | John et al. |
| 8,882,781 B2 | 11/2014 | Smedley et al. |
| 9,066,782 B2 | 6/2015 | Tu et al. |
| D737,450 S | 8/2015 | Abelson |
| 9,155,654 B2 | 10/2015 | Tu et al. |
| 9,173,775 B2 | 11/2015 | Haffner et al. |
| 9,220,632 B2 | 12/2015 | Smedley et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,636,255 B2 | 5/2017 | Haffner et al. |
| 9,668,915 B2 | 6/2017 | Haffner et al. |
| 9,730,638 B2 | 8/2017 | Haffner et al. |
| 9,789,001 B2 | 10/2017 | Tu et al. |
| 9,827,143 B2 | 11/2017 | Lynch et al. |
| 9,962,290 B2 | 5/2018 | Burns et al. |
| 9,987,472 B2 | 6/2018 | Tu et al. |
| 9,993,368 B2 | 6/2018 | Bergheim et al. |
| D833,008 S | 11/2018 | Kalina, Jr. et al. |
| 10,188,551 B2 | 1/2019 | Rangel-Friedman et al. |
| 10,206,813 B2 | 2/2019 | Haffner et al. |
| D846,738 S | 4/2019 | Kalina, Jr. et al. |
| 10,245,178 B1 | 4/2019 | Heitzmann et al. |
| 10,271,989 B2 | 4/2019 | Haffner et al. |
| 10,285,853 B2 | 5/2019 | Rangel-Friedman et al. |
| 10,285,856 B2 | 5/2019 | Tu et al. |
| 10,406,029 B2 | 9/2019 | Tu et al. |
| 10,413,178 B2 | 9/2019 | Graham et al. |
| 10,485,701 B2 | 11/2019 | Haffner et al. |
| 10,485,702 B2 | 11/2019 | Bergheim et al. |
| 10,492,950 B2 | 12/2019 | Lynch et al. |
| 10,499,809 B2 | 12/2019 | Kalina, Jr. et al. |
| 10,517,759 B2 | 12/2019 | Crimaldi et al. |
| 10,568,762 B2 | 2/2020 | Lynch et al. |
| D886,997 S | 6/2020 | Kalina, Jr. et al. |
| 10,674,906 B2 | 6/2020 | Kalina, Jr. et al. |
| 10,813,789 B2 | 10/2020 | Haffner et al. |
| D901,683 S | 11/2020 | Kalina, Jr. et al. |
| 10,828,195 B2 | 11/2020 | Burns et al. |
| 10,828,473 B2 | 11/2020 | Haffner et al. |
| 10,959,941 B2 | 3/2021 | Haffner |
| 11,019,996 B2 | 6/2021 | Kalina, Jr. et al. |
| 11,019,997 B2 | 6/2021 | Kalina, Jr. et al. |
| 11,116,625 B2 | 9/2021 | Kalina, Jr. |
| D938,585 S | 12/2021 | Kalina, Jr. et al. |
| 11,197,780 B2 | 12/2021 | Haffner et al. |
| 11,253,394 B2 | 2/2022 | Haffner et al. |
| 11,318,043 B2 | 5/2022 | Heitzmann et al. |
| 11,376,040 B2 | 7/2022 | Kalina, Jr. et al. |
| 11,426,306 B2 | 8/2022 | Haffner et al. |
| 11,523,938 B2 | 12/2022 | Rangel-Friedman et al. |
| 11,559,430 B2 | 1/2023 | Crimaldi et al. |
| 11,564,833 B2 | 1/2023 | Burns et al. |
| 11,744,458 B2 | 9/2023 | Kalina, Jr. et al. |
| 11,826,104 B2 | 11/2023 | Kalina, Jr. et al. |
| 11,925,578 B2 | 3/2024 | Heitzmann et al. |
| 11,944,573 B2 | 4/2024 | Haffner et al. |
| 11,992,551 B2 | 5/2024 | Haffner |
| 2002/0133168 A1 | 9/2002 | Smedley et al. |
| 2002/0143284 A1 | 10/2002 | Tu et al. |
| 2003/0055372 A1 | 3/2003 | Lynch et al. |
| 2003/0060752 A1 | 3/2003 | Bergheim et al. |
| 2003/0090898 A1 | 5/2003 | Goldstein et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0232015 A1 | 12/2003 | Brown et al. |
| 2003/0236484 A1 | 12/2003 | Lynch et al. |
| 2004/0024345 A1 | 2/2004 | Gharib et al. |
| 2004/0036839 A1 | 2/2004 | Fischer et al. |
| 2004/0111050 A1 | 6/2004 | Smedley et al. |
| 2004/0147870 A1 | 7/2004 | Burns et al. |
| 2004/0154946 A1 | 8/2004 | Solovay et al. |
| 2004/0196431 A1 | 10/2004 | Farberov |
| 2004/0210185 A1 | 10/2004 | Tu et al. |
| 2004/0216749 A1 | 11/2004 | Tu |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0165413 A1 | 7/2005 | Conston et al. |
| 2005/0209549 A1 | 9/2005 | Bergheim et al. |
| 2005/0250788 A1 | 11/2005 | Tu et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0050229 A1 | 3/2006 | Farberov |
| 2006/0074375 A1 | 4/2006 | Bergheim et al. |
| 2006/0084907 A1 | 4/2006 | Bergheim et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2007/0046948 A1 | 3/2007 | Podoleanu et al. |
| 2007/0088432 A1 | 4/2007 | Solovay et al. |
| 2007/0195269 A1 | 8/2007 | Wei et al. |
| 2007/0276483 A1 | 11/2007 | Aharoni et al. |
| 2007/0282244 A1 | 12/2007 | Tu et al. |

(56) References Cited

U.S. PATENT DOCUMENTS

| | | |
|---|---|---|
| 2007/0282245 A1 | 12/2007 | Tu et al. |
| 2007/0291277 A1 | 12/2007 | Everett et al. |
| 2007/0293807 A1 | 12/2007 | Lynch et al. |
| 2008/0043199 A1 | 2/2008 | Whalen |
| 2008/0045878 A1 | 2/2008 | Bergheim et al. |
| 2008/0068560 A1 | 3/2008 | Knighton et al. |
| 2008/0183121 A2 | 7/2008 | Smedley et al. |
| 2009/0046251 A1 | 2/2009 | Peyman et al. |
| 2009/0076436 A2 | 3/2009 | Gharib et al. |
| 2009/0128776 A1 | 5/2009 | Keating et al. |
| 2009/0137989 A1 | 5/2009 | Kataoka |
| 2009/0149829 A1 | 6/2009 | Collins |
| 2009/0157062 A1 | 6/2009 | Hauger et al. |
| 2009/0180123 A1 | 7/2009 | Knighton et al. |
| 2009/0225324 A1 | 9/2009 | Berstein et al. |
| 2010/0027857 A1 | 2/2010 | Wang |
| 2010/0056979 A1 | 3/2010 | Smedley et al. |
| 2010/0091244 A1 | 4/2010 | Volk |
| 2010/0118269 A1 | 5/2010 | Shea et al. |
| 2010/0118270 A1 | 5/2010 | Shea et al. |
| 2010/0134759 A1 | 6/2010 | Silvestrini |
| 2010/0208201 A1 | 8/2010 | Knighton et al. |
| 2010/0249562 A1 | 9/2010 | Zhang et al. |
| 2010/0265461 A1* | 10/2010 | Gille ............... A61B 3/117 351/219 |
| 2011/0026789 A1 | 2/2011 | Hsu et al. |
| 2011/0103658 A1 | 5/2011 | Davis et al. |
| 2011/0213342 A1 | 9/2011 | Tripathi et al. |
| 2012/0078158 A1 | 3/2012 | Haffner et al. |
| 2012/0078362 A1 | 3/2012 | Haffner et al. |
| 2012/0099077 A1 | 4/2012 | Abt |
| 2012/0242957 A1 | 9/2012 | Mordaunt |
| 2012/0257167 A1 | 10/2012 | Gille et al. |
| 2012/0259195 A1 | 10/2012 | Haffner et al. |
| 2013/0018295 A1 | 1/2013 | Haffner et al. |
| 2013/0090534 A1 | 4/2013 | Burns et al. |
| 2013/0103145 A1* | 4/2013 | John ............... A61F 9/0017 351/219 |
| 2013/0182223 A1* | 7/2013 | Wardle ............ A61B 3/117 351/219 |
| 2013/0253404 A1 | 9/2013 | Tu |
| 2013/0253405 A1 | 9/2013 | Tu |
| 2013/0271729 A1 | 10/2013 | Ranchod |
| 2013/0281910 A1 | 10/2013 | Tu |
| 2013/0310930 A1 | 11/2013 | Tu et al. |
| 2014/0307229 A1 | 10/2014 | Hassan et al. |
| 2015/0223981 A1 | 8/2015 | Smedley et al. |
| 2015/0327764 A1 | 11/2015 | Graham et al. |
| 2015/0342875 A1 | 12/2015 | Haffner |
| 2016/0045363 A1 | 2/2016 | Haffner et al. |
| 2016/0354309 A1 | 12/2016 | Heitzmann et al. |
| 2017/0135857 A1 | 5/2017 | Haffner et al. |
| 2017/0181622 A1 | 6/2017 | Graham et al. |
| 2017/0231491 A1 | 8/2017 | Tanassi et al. |
| 2017/0340201 A1 | 11/2017 | Rill |
| 2018/0021170 A1 | 1/2018 | Haffner et al. |
| 2018/0028361 A1 | 2/2018 | Haffner et al. |
| 2018/0070817 A1 | 3/2018 | Kalina, Jr. et al. |
| 2018/0085065 A1 | 3/2018 | Haffner et al. |
| 2018/0161205 A1 | 6/2018 | Tu et al. |
| 2018/0280194 A1 | 10/2018 | Heitzmann et al. |
| 2018/0303665 A1 | 10/2018 | Heitzmann et al. |
| 2018/0310821 A1 | 11/2018 | Kalina, Jr. et al. |
| 2018/0333296 A1 | 11/2018 | Heitzmann et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0104936 A1 | 4/2019 | Gunn et al. |
| 2019/0224046 A1 | 7/2019 | Heitzmann et al. |
| 2019/0321225 A1 | 10/2019 | Smedley et al. |
| 2020/0155349 A1 | 5/2020 | Haffner et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2021/0369447 A1 | 12/2021 | Kalina, Jr. |
| 2022/0000663 A1 | 1/2022 | Haffner et al. |
| 2022/0015628 A1 | 1/2022 | Kalina, Jr. et al. |
| 2022/0119350 A1 | 4/2022 | Murphy et al. |
| 2022/0233349 A1 | 7/2022 | Haffner et al. |
| 2022/0233354 A1 | 7/2022 | Haffner et al. |
| 2022/0313486 A1 | 10/2022 | Heitzmann et al. |
| 2022/0330979 A1 | 10/2022 | Kalina, Jr. et al. |
| 2023/0053931 A1 | 2/2023 | Haffner et al. |
| 2023/0090539 A1 | 3/2023 | Haffner et al. |
| 2023/0157868 A1 | 5/2023 | Haffner et al. |
| 2023/0210694 A1 | 7/2023 | Crimaldi et al. |
| 2023/0293344 A1 | 9/2023 | Burns et al. |
| 2023/0301830 A1 | 9/2023 | Heitzmann et al. |
| 2023/0372303 A1 | 11/2023 | Liu et al. |
| 2024/0065887 A1 | 2/2024 | Heitzmann et al. |
| 2024/0090762 A1 | 3/2024 | Kalina, Jr. et al. |
| 2024/0207091 A1 | 6/2024 | Heitzmann et al. |

FOREIGN PATENT DOCUMENTS

| | | |
|---|---|---|
| WO | WO 2000/64389 | 11/2000 |
| WO | WO 2000/64390 | 11/2000 |
| WO | WO 2000/64391 | 11/2000 |
| WO | WO 2000/64393 | 11/2000 |
| WO | WO 2001/97727 | 12/2001 |
| WO | WO 2002/36052 | 5/2002 |
| WO | WO 2002/080811 | 10/2002 |
| WO | WO 2002/087418 | 11/2002 |
| WO | WO 2002/089699 | 11/2002 |
| WO | WO 2003/073968 | 9/2003 |
| WO | WO 2009/158517 | 12/2009 |
| WO | WO 2013/109771 | 7/2013 |
| WO | WO 2015/180923 | 12/2015 |
| WO | WO 2017/087713 | 5/2017 |
| WO | WO 2003/015659 | 2/2023 |
| WO | WO 2023/22551 | 11/2023 |
| WO | WO 2023/225551 | 11/2023 |

OTHER PUBLICATIONS

"Beam Steering by Wedge Prisms," last updated Jun. 15, 2006, available at: http://micro.magnet.fsu.edu/primer/java/prismsandbeamsplitters/wedgeprisms/index.html.

Beck, Allen D., et al., "360° Trabeculotomy for Primary Glaucoma," Arch. Ophthalmol. 113 (Sep. 1995), pp. 1200-1202.

Buskirk, E. Michael et al., "Lens Depression and Aqueous Outflow in Enucleated Primate Eyes", American Journal of Ophthalmology, vol. 76, No. 5, Nov. 1973, pp. 632-640.

http://glaucomatoday.com/2016/1 O/gonioscopy-is-essential-for-migs/ Posted Oct. 2016.

Guttman, Cheryl, "Continuous IOP Monitoring Possible with Microsensor: Implantable Device Aims to Overcome Deficiencies of Current Monitoring Techniques", (Improvement in Patient Management) (Intraocular Pressure), Ophthalmology Times, Oct. 15, 2003, as cited in HighBeam Research, http://www.highbeam.com/DocPrint.aspx?DocId=1G1:109595800.

Haag-Streit Contact Glasses Brochure, retrieved Mar. 20, 2007.

https://entokey.com/gonioscopy-2/ Uploaded Oct. 2016.

Newell, Frank W., Ophthalmology Principles and Concepts, 1996, Anne S. patterson/Mosby, Eighth edition, pp. 10-21 and 32.

Nickells, Robert W., "Apoptosis of Retinal Ganglion Cells in Glaucoma: An Update of the Molecular Pathways Involved in Cell Death", Survey of Ophthalmology, vol. 43, Supplement 1, Jun. 1999, pp. S-151 through S-161.

Ocular Hill Surgical Gonioprism from at least as early as Jun. 29, 2007 in 3 pages, downloaded from http://www.ocularinc.com.

Ocular Khaw Surgical Gonioprism from at least as early as Jun. 29, 2007 in 3 pages, downloaded from http://ocularinc.com.

Ocular Swan Autoclavable Gonioprism from at least as early as Jun. 29, 2007 in 3 pages, downloaded from http://ocularinc.com.

Product No. E8989; Name: Berdahl Gonio Prism Stabilizer, Feb. 2015, http://storzeye.com/products/49940/other-eye-instruments/berdahl-gonio-prism-stabilizer/e8989.aspx.

(56) References Cited

OTHER PUBLICATIONS

U.S. Clinical Wick Trials, Oct. 11, 1999, website http://www.cornea.org/us.htm. Allingham, R. R., et al., "Morphometric Analysis of Schlemm's Canal in Normal and Glaucomatous Human Eyes", Glaucoma Paper Presentation, (abstract only—not dated).

Vandenburgh et al., "A Novel Ocular Hypotensive Lipid: Initial Safety and Efficacy of AGN 192024", Glaucoma Clinical Pharmacology II, Abstract B58, IVOS 1998 vol. 39, (cover page and page No. S258).

Volk, "Aspheric Ophthalmic Lenses", Refraction, International Ophthalmology Clinics, vol. 5, No. 2, Jun. 1965.

https://web.archive.org/web/20170106073123/http://ocularinc.com/ Available Jan. 6, 2017.

Examination Report in Australian application No. 2022259798, dated Sep. 5, 2024, in 4 pages.

* cited by examiner

GONIOSCOPIC DEVICES

CROSS-REFERENCE TO RELATED APPLICATIONS

This application is a continuation of U.S. patent application Ser. No. 17/332,885, filed May 27, 2021, titled "GONIOSCOPIC DEVICES," which is a continuation of Ser. No. 16/706,525, filed Dec. 6, 2019, titled "GONIOSCOPIC DEVICES," which is a continuation of U.S. patent application Ser. No. 15/559,391, filed Sep. 18, 2017, titled "GONIOSCOPIC DEVICES," which is a U.S. National Phase of PCT/US2016/023296, having an international filing date of Mar. 18, 2016, designating the United States, and titled "GONIOSCOPIC DEVICES," which claims the benefit of U.S. Provisional Patent Application No. 62/136,376, filed Mar. 20, 2015, and titled "GONIOSCOPIC DEVICES," and U.S. Provisional Patent Application No. 62/202,017, filed Aug. 6, 2015, and titled "GONIOSCOPIC DEVICES." The entirety of each of the above-identified applications is hereby incorporated by reference and made a part of this specification for all that it discloses.

BACKGROUND

Field of the Disclosure

Various embodiments disclosed herein relate to ophthalmoscopic devices, systems, and/or methods for viewing structures of the eye including but not limited to the anterior chamber. In some embodiments, the devices, systems, and/or methods can include a gonioscope or a gonioscopic attachment for stabilizing the eye.

Description of the Related Art

Gonioscopy is a technique used for viewing the inner parts of the eye, such as the anterior chamber of the eye (e.g., the iridocorneal angle or anterior chamber angle) during a surgical procedure, for evaluation, and/or for classification of normal and abnormal structures. Devices used for gonioscopy are known as gonioscopes. Observation of the anterior chamber and especially the iridocorneal angle or anterior chamber angle, which can be difficult or impossible to see with the use of simple microscopes, is commonly used for diagnosis of eye diseases. For example, the classification of glaucoma can rely heavily upon knowledge of the anterior chamber anatomy, particularly that of the anterior chamber angle. Additionally, some surgical procedures used to treat glaucoma involve placing a small tubular stent into the trabecular meshwork in the anterior chamber angle formed by the iris and the cornea. Proper placement of the stent may depend on visualization of the trabecular meshwork.

The anterior chamber of a human eye is commonly evaluated with an illuminated microscope (e.g., a slit lamp stereromicroscopy), but the anterior chamber angle is typically hidden from ordinary view because of total internal reflection of light rays emanating from the anterior chamber angle structures. A small optical device known to ophthalmologists as a gonioscope can be used to enhance visibility of the anterior chamber. During surgical applications, it may be hand held by the surgeon in place over the patient's cornea while he/she is performing the surgical procedure. Although various gonioscopic devices exist, there remains a need for improved gonioscopic devices.

SUMMARY OF CERTAIN EXAMPLE EMBODIMENTS

Certain example embodiments are summarized below for illustrative purposes. The embodiments are not limited to the specific implementations recited herein. Embodiments of the present disclosure can relate to devices and methods for viewing the inner parts of the eye, such as the anterior chamber angle or other portions of the anterior chamber.

Various embodiments disclosed herein can relate to a gonioscopic attachment configured to attach to a gonioscope for use on a subject's eye. The gonioscopic attachment can include a generally C-shaped body having an open side, the body configured to receive a gonioscope to removably attach the body to the gonioscope. The gonioscopic attachment can include a first arm positioned on the side of the body opposite the open side, the first arm extending distally from the body by a first distance, one or more first retention elements disposed on the first arm, a second arm positioned on the body at one side of the open side, the second arm extending distally from the body by a second distance that is less than the first distance, one or more second retention elements disposed on the second arm, a third arm positioned on the body at another side of the open side, the third arm extending distally from the body by a third distance that is less than the first distance, and one or more third retention elements disposed on the third arm. The first, second, and third retention elements can be configured to engage an eye to retain the gonioscope relative to the eye.

One or more of the first arm, the second arm, and the third arm can include a tapered distal end that can be configured to slide under tissue adjacent to the eye when pressed against the tissue. One or more of the first arm, the second arm, and the third arm can include a rounded tip at a distal end thereof. The first, second, and/or third retention elements can include cleats having a generally frustoconical shape. The retention elements can be sufficiently blunt so as to deform tissue of the eye without piercing into the tissue of the eye when pressed against the tissue of the eye.

The first distance can be at least about 100% larger than the second distance and the third distance. The first distance can be at least about 300% larger than the second distance and the third distance. The first distance can be no more than about 1,500% larger than the second distance and the third distance. The body can be configured to flex when the gonioscope is attached to the body such that the body applies a clamping force on the gonioscope.

The retention elements can be configured to position the gonioscope so that at least a portion of a concave distal surface of the gonioscope is spaced apart from the eye. The retention elements can be configured to position the gonioscope so that at least about 50% of a concave distal surface of the gonioscope is spaced apart from the eye. The retention elements can be configured to position the gonioscope so that the curvature of the concave distal surface is offset from a corresponding curvature of the eye by an angle between about 3 degrees and about 20 degrees. The body can include a plurality of engagement features configured to engage the gonioscope at locations that are disposed on a first generally circular path, and the plurality of retention elements can be disposed on a second generally circular path, and the second generally circular path can be offset from the first generally circular path by an angle between about 5 degrees and about 30 degrees.

Various embodiments disclosed herein can relate to a gonioscopic attachment configured to attach to a gonioscope for use on a subject's eye. The gonioscopic attachment can include a body configured to removably attach to a gonioscope and a plurality of atraumatic retention elements, which can be coupled to the body and can be configured to engage an eye to retain the gonioscope relative to the eye.

Various embodiments disclosed herein can relate to a gonioscopic attachment configured to attach to a gonioscope for use on a subject's eye. The gonioscopic attachment can include a body configured to removably attach to a gonioscope having a concave distal surface and a plurality of retention elements, which can be coupled to the body and can be configured to engage an eye to retain the gonioscope relative to the eye. The plurality of retention elements can be configured to position the gonioscope so that at least a portion of the concave distal surface is spaced apart from the eye.

The plurality of retention elements can be configured to engage the eye without causing trauma to the eye. The plurality of retention elements can be sufficiently blunt so as to deform tissue of the eye without piercing into the tissue of the eye when pressed against the tissue of the eye. The plurality of retention elements can have a minimum radius of curvature of at least about 0.002 inches. The plurality of retention elements can have a minimum radius of curvature of at least about 0.003 inches. The plurality of retention elements can have at least a portion with a radius of curvature of less than or equal to about 0.015 inches. The retention elements can be configured to contact the sclera of the eye when the gonioscope is positioned for viewing an anterior chamber of the eye. The retention elements can be configured to not contact the cornea of the eye when the gonioscope is positioned for viewing an anterior chamber of the eye. The gonioscopic attachment can be configured such that the gonioscopic attachment and the gonioscope do not directly contact the cornea of the eye when in use.

The gonioscopic attachment can include one or more arms extending distally from the body, and at least one of the retention elements can be disposed on a distal portion of the one or more arms. The gonioscopic attachment can include a first arm extending distally from the body by a first distance, where at least one of the retention elements can be disposed on the first arm, and a second arm extending distally from the body by a second distance, where at least one of the retention elements can be disposed on the second arm. The first distance can be larger than the second distance. The gonioscopic attachment can include a third arm extending distally from the body by a third distance, which can be substantially the same as the second distance. At least one of the retention elements can be disposed on the third arm. The body can be generally C-shaped having an open side, and the second arm can be positioned at a first end of the body, and the first arm can be positioned at an apex of the body opposite of the open side, and the third arm can be positioned at a second end of the body. The first distance can be at least about 50% larger than the second distance. The first distance can be at least about 100% larger than the second distance. The first distance can be at least about 300% larger than the second distance. In some implantations, the first distance is no more than about 1,500% larger than the second distance.

The body can be generally C-shaped. The body can have an open side configured to removably receive the gonioscope, and wherein the body is configured to flex when the gonioscope is attached to the body such that the body applies a clamping force on the gonioscope. The body can include at least one groove configured to receive a corresponding feature on the gonioscope. The body can include one or more tabs configured to secure the body to the gonioscope.

One or more of the retention elements can be generally V-shaped. One or more of the retention elements can have a generally frustoconical shape. The retention elements can include textile, cloth, or fabric material.

The gonioscopic attachment can include a coupling mechanism configured to couple the gonioscopic attachment to a lid speculum. The gonioscopic attachment can include one or more elongate flexible tethers. The gonioscopic attachment can include a first tether extending in a first direction from an arm of the gonioscopic attachment, and a second tether extending in a second direction opposite of the first direction from the arm of the gonioscopic attachment. The coupling mechanism can be configured such that the gonioscopic attachment can be movable between a disengaged position and an engaged position when coupled to the lid speculum. The gonioscopic attachment can include a lid speculum coupled to the gonioscopic attachment via the coupling mechanism.

The gonioscopic attachment can include one or more handle attachment features configured to removably receive a handle. The plurality of retention elements can be configured to position the gonioscope so that at least about 50% of the concave distal surface is spaced apart from the eye. The plurality of retention elements can be configured to position the gonioscope so that at least about 75% of the concave distal surface is spaced apart from the eye. The plurality of retention elements can be configured to position the gonioscope so that the full concave distal surface is spaced apart from the eye. The plurality of retention elements can be configured to position the gonioscope so that the curvature of the concave distal surface is offset from a corresponding curvature of the eye by an angle between about 3 degrees and about 20 degrees. The plurality of retention elements can be configured to position the gonioscope so that the curvature of the concave distal surface is offset from a corresponding curvature of the eye by an angle between about 7 degrees and about 15 degrees. The plurality of retention elements can be configured to position the gonioscope so that the curvature of the concave distal surface is offset from a corresponding curvature of the eye by an angle of about 10 degrees. The body can include a plurality of engagement features configured to engage the gonioscope at locations that are disposed on a first generally circular path, and the plurality of retention elements can be disposed on a second generally circular path, and the second generally circular path can be offset from the first generally circular path by an angle between about 5 degrees and about 30 degrees. The second generally circular path can be offset from the first generally circular path by an angle between about 10 degrees and about 20 degrees. The second generally circular path can be offset from the first generally circular path by an angle of about 17 degrees.

The plurality of retention elements can be positioned to be distributed around the gonioscope across a circumferential angle of at least about 220 degrees. The plurality of retention elements can be positioned to be distributed around the gonioscope across a circumferential angle of less than or equal to about 320 degrees. The plurality of retention elements can be positioned to be distributed around the gonioscope such that each gap between adjacent retention elements has a circumferential angle that is less than or equal to about 145 degrees. The plurality of retention elements can be positioned to be distributed around the gonioscope such that at least one of the gaps between adjacent retention elements has a circumferential angle that is at least about 60 degrees.

The gonioscopic attachment can include an arm that can have a tapered distal end that is configured to slide under tissue adjacent to the eye when pressed against the tissue. The gonioscopic attachment can include an arm having a rounded tip at a distal end.

Various embodiments disclosed herein can relate to a gonioscope assembly, which can include a gonioscope, and the gonioscopic attachments disclosed herein. The concave distal surface of the gonioscope can have a radius of curvature that generally corresponds to a curvature of a cornea of a subject's eye. The concave distal surface of the gonioscope can have a radius of curvature between about 5 mm and about 11 mm.

The gonioscope can include a gonioscopic optical element and at least one fixation point configured to be visible to the subject when the gonioscope is positioned on the eye. The gonioscope can include multiple fixation points having different appearances and different locations. The gonioscope can include three or more fixation points having different appearances and aligned along a linear path. The fixation point can include a light source. The at least one fixation point can include a plurality of light sources configured to be selectively illuminated. The fixation point can include a light pipe. The gonioscopic optical element can be overmolded around the light pipe. A portion of the light pipe can be disposed outside the gonioscopic optical element, and a portion of the light pipe can extend into a recess in the gonioscopic optical element. The light pipe can be configured to direct light from a microscope into the eye to be visible to the subject.

The gonioscope assembly can include a removable handle. The gonioscope can include one or more handle attachment features configured to removably receive an attachment feature on the handle to removably couple the handle to the gonioscope. The handle can be configured to attach to the gonioscope or gonioscopic attachment by a loose engagement that can be disengaged by lifting the handle away from the gonioscope or gonioscopic attachment without moving the position of the gonioscope or gonioscopic attachment on the eye. The handle can be removably attachable at multiple orientations. The handle can be removably attachable at a right-handed orientation and at a left-handed orientation.

Various embodiment disclosed herein can relate to a gonioscope, which can include a gonioscopic optical element having a concave distal surface, a handle coupled to the gonioscopic optical element, and a plurality of retention elements coupled to the gonioscopic optical element and configured to engage an eye to retain the gonioscope relative to the eye. The plurality of retention elements can be configured to position the gonioscopic optical element so that at least a portion of the concave distal surface is spaced apart from the eye. The plurality of retention elements can be configured to engage the eye without causing trauma to the eye.

Various embodiments disclosed herein can relate to a gonioscope, which can include a gonioscopic optical element having a concave distal surface, a handle coupled to the gonioscopic optical element, and a plurality of atraumatic retention elements coupled to the gonioscopic optical element and configured to engage an eye to retain the gonioscope relative to the eye. The plurality of retention elements can be stationary relative to the gonioscopic optical element.

The gonioscope can include at least one fixation point configured to be visible to the subject when the gonioscope is positioned on the eye. The at least one fixation point can include various features described herein.

Various embodiments disclosed herein can relate to a gonioscope, which can include a gonioscopic optical element having a concave distal surface, a handle coupled to the gonioscopic optical element, and at least one fixation point configured to be visible to the subject when the gonioscope is positioned on the eye.

The gonioscope can include a coupling mechanism configured to couple the gonioscope to a lid speculum. The gonioscope can include one or more elongate flexible tethers. The gonioscope can include a first tether extending in a first direction from an arm of the gonioscope, and a second tether extending in a second direction opposite of the first direction from the arm of the gonioscope. The coupling mechanism can be configured such that the gonioscope can be movable between a disengaged position and an engaged position when coupled to the lid speculum.

The gonioscope can include a removable handle. The can include one or more handle attachment features configured to removably receive an attachment feature on the handle to removably couple the handle to the gonioscope. The handle can be configured to attach to the gonioscope by a loose engagement that can be disengaged by lifting the handle away from the gonioscope without moving the position of the gonioscope on the eye. The handle can be removably attachable at multiple orientations. The handle can be removably attachable at a right-handed orientation and at a left-handed orientation.

Various embodiments disclosed herein can relate to a gonioscopic instrument, which can include a gonioscopic optical element and a coupling mechanism configure to couple the gonioscopic optical element to a lid speculum. The gonioscopic instrument can include a gonioscopic attachment attached to the gonioscopic optical element, wherein the coupling mechanism is configured to attach the gonioscopic attachment to the lid speculum. The gonioscopic instrument can include a lid speculum coupled to the gonioscopic optical element via the coupling mechanism.

Various embodiments disclosed herein can relate to a gonioscope, which can include a gonioscopic optical element having a concave distal surface, a handle coupled to the gonioscopic optical element, and a light pipe disposed in the handle and configured to direct light into an eye.

The light pipe can be configured to direct light through the gonioscopic optical element to the eye. The light pipe can be configured to direct light through scleral tissue of the eye to illuminate Schlemm's canal. The light pipe can be configured to direct light to transilluminate or retroilluminate the anterior chamber of the eye. The light pipe can be configured to direct light to transilluminate or retroilluminate the trabecular meshwork. The light pipe and the gonioscopic optical element can be integrally formed.

The gonioscope can include a light inlet configured to receive light so that the received light propagates along the light pipe. The gonioscopic optical element can be at a distal end of the handle, and the light inlet can be at a proximal end of the handle. The gonioscope can include a light collector configured to direct light into the light pipe. The light collector can include an input end that is wider than an output end. The input end can be configured to receive light from outside the gonioscope, and the output end can be configured to direct the light into the light inlet so that the light propagates along the light pipe. The gonioscope can include a removable cap configured to cover the light inlet when attached to the gonioscope to impede light from entering the light pipe.

The gonioscope can include a light source configured to input light into the light pipe, and a power source configured to provide electrical power to the light source. The gonioscope can include a user interface having one or more user input elements for a user to control the light source. The gonioscope can include a controller configured to receive input from the user interface and configured to control the light source based on the received input. The gonioscope can include a lighting assembly that includes the light source and the power source, and the lighting assembly can be removably attachable to the handle. The light source and power source can be disposed inside the handle.

The handle can be removable from the gonioscopic optical element. The handle can include a recess that is configured to receive the light pipe therein when the handle is coupled to the gonioscopic optical element. The light pipe can include a first light pipe portion and a second light pipe portion, and the first light pipe portion can be inside the handle, and the second light guide portion can be coupled to the gonioscopic optical element and configured to be received into the recess of the handle.

The handle can include an outer handle portion that surrounds at least a portion of the light pipe. The outer handle portion can have a reflective inner surface. The light pipe can be formed by a hollow interior of the outer handle portion, and the reflective inner surface can reflect light to propagate along the light pipe. The light pipe can include a transparent material configured to propagate light along the light pipe by total internal reflection. The gonioscope can include a cladding material disposed between the light pipe and the outer handle portion. The cladding material can have a lower index of refraction that is lower than an index of refraction of the transparent material of the light pipe. The gonioscope can include a gap between the outer handle portion and the transparent material of the light pipe, the gap having a material with an index of refraction that is lower than an index of refraction of the transparent material of the light pipe.

BRIEF DESCRIPTION OF THE DRAWINGS

The following drawings and the associated descriptions are provided to illustrate example embodiments of the present disclosure and do not limit the scope of the claims.

DETAILED DESCRIPTION OF CERTAIN EMBODIMENTS

Figure 1:
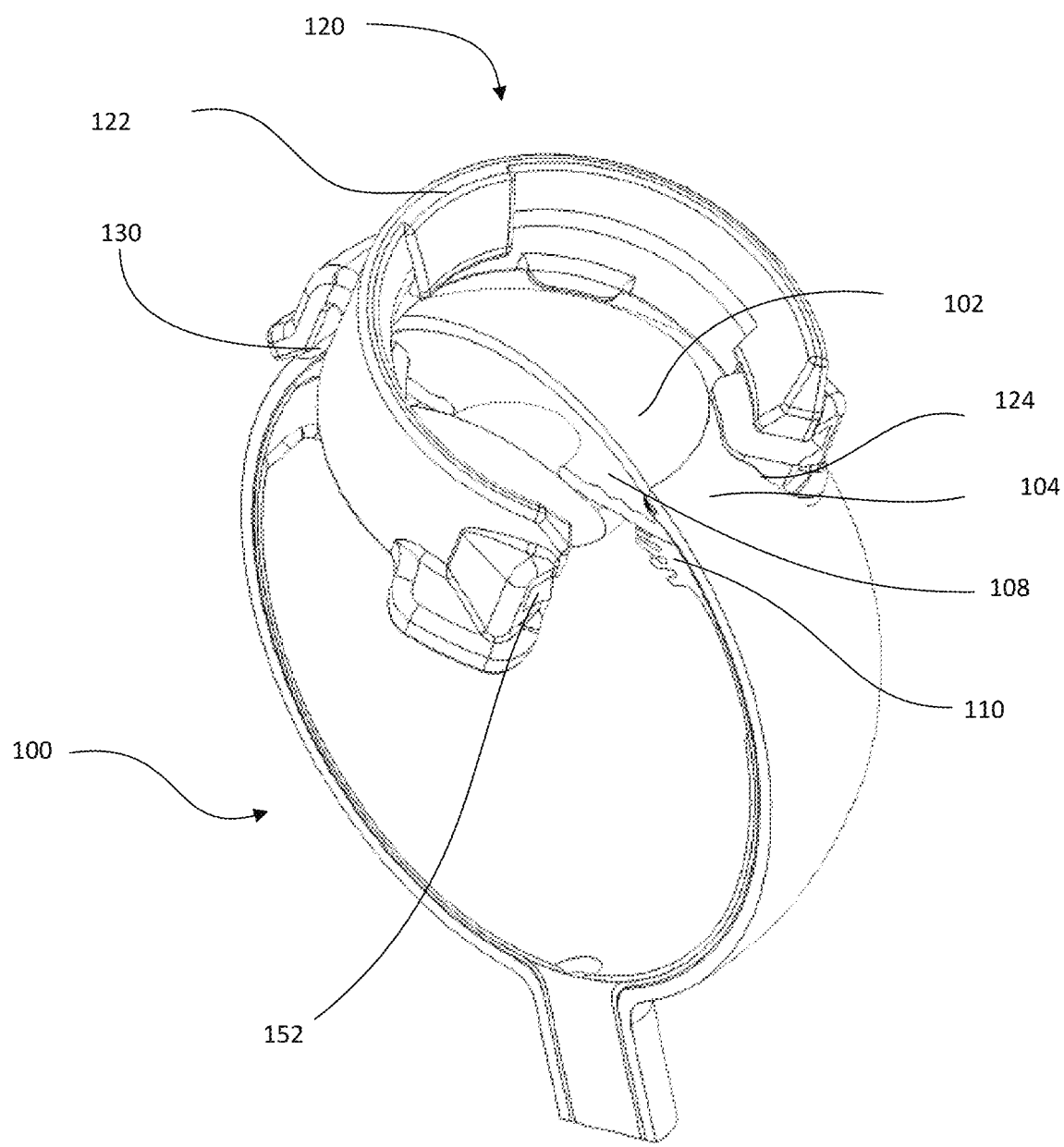
FIG. 1 is a perspective view of an example embodiment of a gonioscopic attachment on a patient's eye.

Certain embodiments will now be described with reference to the accompanying figures, wherein like numerals refer to like elements throughout. In some instances like elements are referred to using reference numbers having the same last two digits, where the first one or two digits can refer to the figure number. The terminology used in the description presented herein is not intended to be interpreted in any limited or restrictive manner, simply because it is being utilized in conjunction with a detailed description of certain specific embodiments. Furthermore, embodiments described herein may comprise several novel features, no single one of which is solely responsible for its desirable attributes or which is essential to practicing the inventions herein described.

A gonioscope may be used during medical procedures such as minimally invasive glaucoma surgery (MIGS). Such procedures may involve injections and/or implantations that require access to the subconjunctival space in different positions and angles.

In some instances, a patient's eye can move during a surgical procedure. A stabilizing mechanism can be used (e.g., on a gonioscope or on an attachment that is coupled to a gonioscope) to align the gonioscope and restrain or reduce the patient's eye from moving relative to the gonioscope. Aligning the gonioscope and stabilizing the patient's eye can enable the surgeon to operate efficiently and more accurately by viewing the anterior chamber at an optimal angle while reducing intraoperative eye movement.

Intraoperative eye movement can present challenges for a user of the gonioscope (e.g., a surgeon or other medical practitioner) and the patient. For example, the user may be challenged in adjusting the gonioscope on a patient's eye to align the gonioprism at a desired viewing angle. Also, manually stabilizing a conventional gonioscope to the patient's eye can be difficult, in some instances, due to fluid present in corneal surface such as natural bodily fluid and/or viscoelastic gel (e.g., index matching gel) used during operation.

In some embodiments, a gonioscopic stabilizer can be used to stabilize the gonioscope. The gonioscopic stabilizer can facilitate placement and alignment of the gonioscope to the patient's eye at a desired viewing angle. The gonioscopic stabilizer can use atraumatic retention features, as opposed to sharp or aggressively textured retention features or retention elements that may cause trauma to ocular tissue (e.g. scleral, conjunctival, and/or corneal tissue). In some embodiments, the gonioscopic stabilizer can be configured to not contact the cornea. For example, the retention elements can be configured to engage the sclera or other ocular tissue that is not the cornea. Direct contact to the cornea may, in some cases, not provide proper alignment and stabilization. Direct contact to the cornea may also cause corneal abrasions and patient discomfort, which can present challenges (e.g., postoperatively).

Intraoperative eye movement of a patient can be reduced or restrained by the patient. In some embodiments, a gonioscope can include a fixation point that is visible to the patient. For example, a user can instruct a patient to gaze at a certain fixation point to restrain eye movement.

A gonioscopic attachment designed to stabilize a patient's eye can be used with a gonioscope. By way of example, stabilization and alignment of patients' eyes can be used in procedures such as glaucoma surgery (e.g., minimally invasive glaucoma surgery (MIGS)), laser trabeculoplasty, such as selective laser trabeculoplasty (SLT) or argon laser trabeculoplasty (ALT), fundus laser, vitrectomy laser, and suture lysis optics where ocular retention and eye/lens stabilization would be beneficial. To stabilize and align a patient's eye, a gonioscopic attachment can be used with a gonioscope. A gonioscopic attachment can be used for lateral stabilization of a gonioscopic optical element on the eye. A gonioscopic attachment can be used to restrain the eye to ensure visualization. A gonioscopic attachment can be used to restrain the eye due to lack of patient compliance. A gonioscopic attachment can be used to restrain the eye to prevent trauma during surgery. A gonioscopic attachment can be used with the microscope, for example by maximizing light in and light out while providing a minimally distorted view.

In some embodiments, a gonioscopic attachment can be used interchangeably with various different gonioscopes having different designs. In some embodiments, a gonioscopic attachment can be shaped or otherwise configured to be used with a specific type of gonioscope. In some implementations, the gonioscopic attachment can be configured to be used with an Ocular Hill surgical gonioprism (which is sometimes referred to as a Hill gonioprism). The design of a gonioscopic attachment can be modified to accommodate various gonioscopic optical elements. A gonioscopic attachment can be used clinically during an examination of a patient's eye. A gonioscopic attachment can be used before or after a surgical operation. A gonioscopic attachment can be used during a surgical operation, such as during implantation of an optical stent (e.g., into the trabecular meshwork). The gonioscopic attachment can be configured to lift the gonioscopic optical element off of the eye during use, for example such that at least part of the concave contact surface of the gonioscope can be suspended above the corresponding structure (e.g., the cornea) of the eye. In some embodiments, the gonioscopic attachment can position the gonioscopic optical element such that the concave contact surface is offset by an angle (e.g., of about 10 degrees in some implementations) from sphere-on-sphere contact between the eye (e.g., the cornea) and the concave contact surface of the gonioscope. An index matching gel can be used to fill the space between the eye and the contact surface on the gonioscope optical element.

A gonioscopic attachment can be configured to align the gonioscope optical element view using circumferential retention elements (e.g., distributed across at least part of a circumference around the gonioscopic optical element or eye). The retention elements can comprise a multi-point contact system. For example, at least some of the retention elements can be disposed on one or more arms (e.g., three arms) forming a plurality of (e.g., three) contact areas that are spaced apart from one another. The plurality of arms of the gonioscopic attachment can be configured to suspend the gonioscope optical element from the patient's eye during use. One or more of the arms can be longer than the other arms, to offset the gonioscopic optical element from the corresponding structure of the eye (e.g., the cornea). Accordingly, the gonioscopic attachment can place and seamlessly align the gonioscope optical element at a desired angle relative to the eye. The retention elements can be disposed on distal surfaces of the arms. The retention elements can interface with the scleral and/or conjunctival tissues only, while minimizing the potential corneal contact with the retention elements, the gonioscope optical element, and/or other portions of the gonioscopic system.

A user, such as a physician, can apply a minimal downward force to the patient's eye with a gonioscope attached to the gonioscopic attachment to restrain the eye. The retention elements can restrain the eye at multiple points. The retention elements can have an atraumatic retention structure. The atraumatic structure can comprise a polymer, such as plastic.

FIG. 1 is a perspective view of an example embodiment of a gonioscopic attachment on a patient's eye. In FIG. 1, the eye is shown as a cross-sectional view. During use the gonioscopic attachment 120 can be coupled to a gonioscope, such as a Hill gonioprism. The gonioscope is omitted from view in FIG. 1 to facilitate viewing of the gonioscopic attachment 120. The gonioscopic attachment 120 can be used on a patient's eye 100 which includes cornea 102, sclera 104, anterior chamber 108, ciliary body 110, etc. The gonioscopic attachment 120 can be configured to avoid contact with the cornea 102 during use. In some implementations, the gonioscopic attachment can contact only the sclera during clinical use. The gonioscopic attachment 120 can be configured to restrain the patient's eye 100 from movement, while the user (e.g., a surgeon or other medical practitioner) views through a gonioscope attached to the gonioscopic attachment 120 to view portions of the eye 100, such as the anterior chamber 108. The user can use a microscope to view the eye through the gonioscope. The gonioscopic attachment 120 can comprise a body 122 and a plurality of retention elements 130. The body 122 can comprise a distal surface 124, which can have a generally concave shape, in some embodiments. The body 122 can be C-shaped. The retention elements 130 can be configured to contact the sclera 104, and not the cornea 102.

The retention elements 130 can be located on the distal side of the body 122. For example, the retention elements 130 can be adjacent to the distal surface 124. The retention elements 130 can be disposed on the distal surface 124. The retention elements 130 can be configured to contact certain portions of the patient's eye, while avoiding contact with other portions. For example, the retention elements 130 can be configured to contact the sclera 104 and/or conjunctival tissue, while avoiding contact with the cornea 102. The gonioscopic attachment 120 can be configured to avoid contact with the lid speculum, not shown, during use. The retention elements 130 can comprise atraumatic structures. The retention elements 130 can comprise a multi-point contact structure with multiple contact points configured to be distributed around the eye 100 on the area surrounding the cornea 102. The retention elements 130 can have minimal contact surface area, in some cases.

Figure 11:
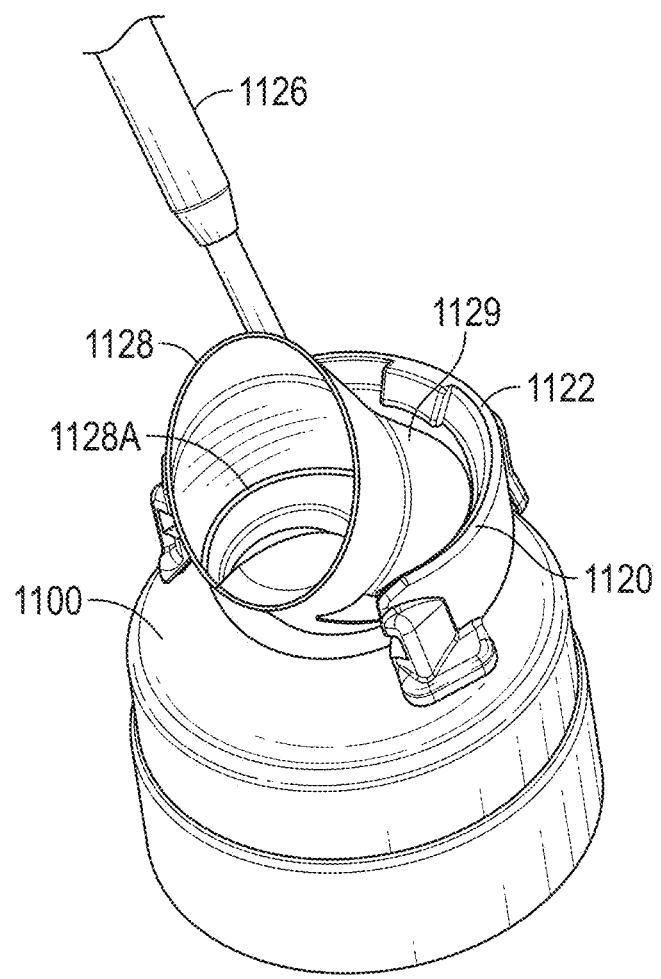
FIG. 11 is a perspective view of a gonioscope used with an example embodiment of a gonioscopic attachment on a model eye.

The C-shaped body 122 can be used to attach (e.g., to clamp) the gonioscopic attachment 120 onto a gonioscope. For example, the gonioscope can include a gonioscopic optical element that can have a distal portion that has a generally cylindrical outer shape comprising a distal circumference. The body 122 can surround and clamp onto the distal circumference of the distal end of the gonioscope optical element. The retention elements 130 can be stationary relative to the gonioscope and/or stationary relative to the body 122 of the gonioscopic attachment 120. FIG. 11 is a perspective view of a gonioscope used with an example embodiment of a gonioscopic attachment on a model eye 1100. A gonioscope can comprise a handle 1126, a handle attachment element 1129 that couples the handle to the gonioscopic optical element (e.g., a gonioscope clamping portion that clamps onto the gonioscopic optical element and has the handle coupled thereto), and a gonioscope optical element 1128. The gonioscopic attachment 1120 can attach to the gonioscopic optical element 1128, the handle 1126, the handle attachment element 1129, any combination thereof, or any other part of the gonioscope such that the gonioscopic attachment is positioned to contact the eye during use, as discussed herein. The gonioscope optical element can comprise a proximal surface 1128A and a distal surface 1225A (which can be seen in FIG. 12). The distal surface 1225A can be a contact surface having a concave surface that generally corresponds to the curvature of the cornea 102 (e.g., having a radius of curvature between about 5 mm and about 11 mm). During use, light from structures inside the eye (e.g., the anterior chamber angle) can propagate to the cornea. Instead of reflecting back into the eye by total internal reflection, as can happen when no gonioscope is used, the light can exit the eye and enter the gonioscopic optical element 1128 via the distal surface 1225A. An index matching gel can be used between the cornea and the distal surface of the gonioscopic optical element to facilitate the passage of light from the eye into the gonioscopic optical element. The light can then exit the gonioscopic optical element 1128 via the proximal surface 1128A to be viewed by a medical practitioner (e.g., using a microscope).

The body 122, 1122 can clamp onto the gonioscope, such as onto the handle attachment element 1129 or the gonioscopic optical element 1128. When being attached to the gonioscope, the two sides of the C-shaped body 122 can flex away from each other to make room for the gonioscope to enter the C-shaped body 122. Then the two sides of the C-shaped body 122 can move back towards each other to hold gonioscopic attachment onto the gonioscope. In some embodiments, the C-shaped body can be sized or otherwise configured such that it remains in a flexed state when attached to the gonioscope, such that the two sides of the C-shaped body press towards each other to clamp against the gonioscope. For example, the diameter of the C-shaped body can be smaller than the diameter of the attachment portion of the gonioscope. The body can include at least one groove 152 configured to removably receive a corresponding feature on the gonioscope. The body 122 can be configured to flex when the gonioscope is attached to the body such that the body applies a clamping force on the gonioscope. The C-shape of the body 122 can be stretched open a little so that it clamps around the gonioscope when attached.

Figure 13:
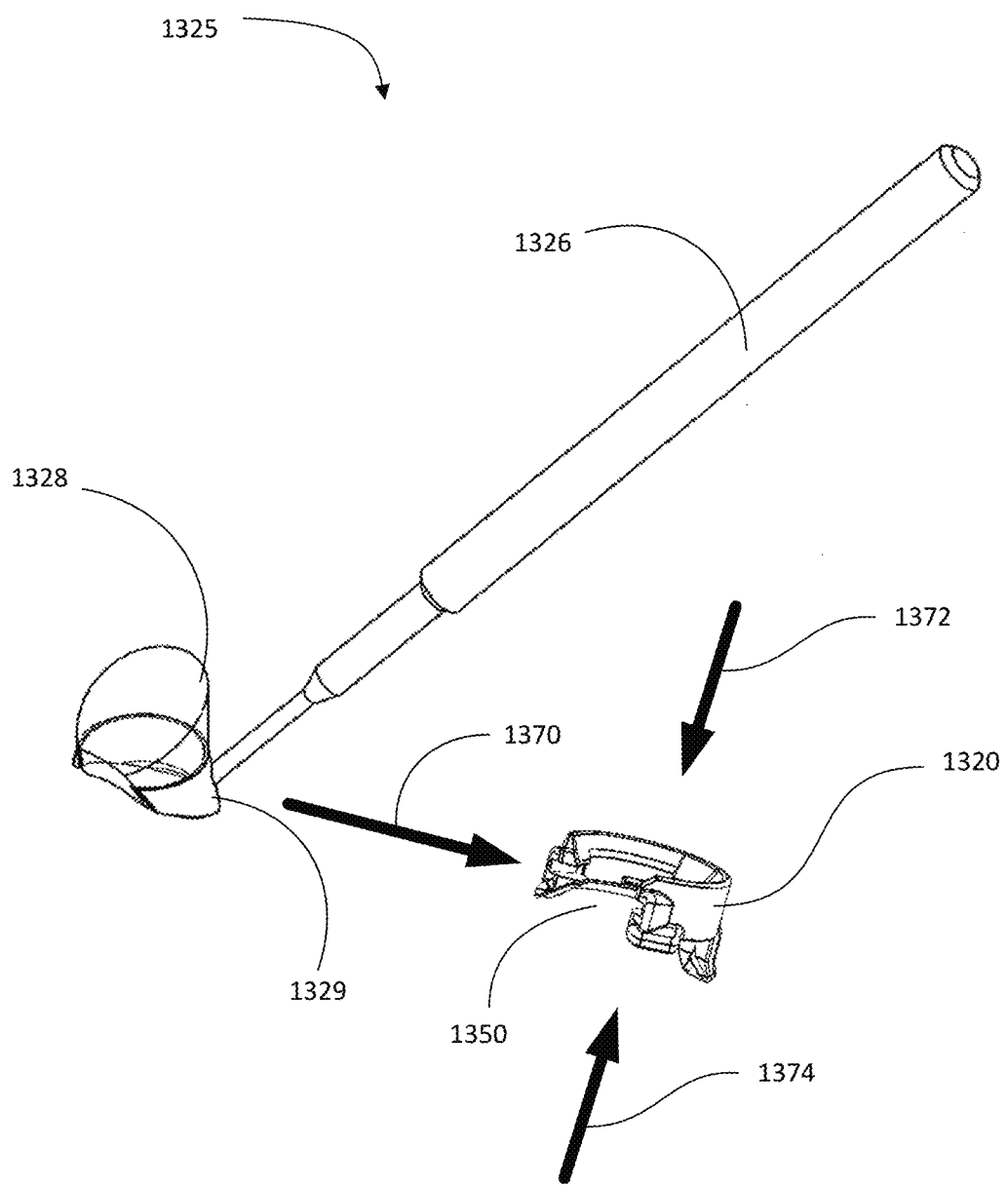
FIG. 13 is a perspective view showing an example embodiment of a gonioscope and a gonioscopic attachment in a detached configuration.

By way of example, FIG. 13 shows an example embodiment of a gonioscope 1325 and a gonioscopic attachment 1320 detached therefrom. The gonioscope 1325 can be a Hill gonioprism, although other types of gonioscopes can be used in some implementations. The gonioscope 1325 can include a gonioscopic optical element 1328, which can be the same as or similar to the other gonioscopic optical elements described and shown herein. The gonioscope 1325 can include a handle 1326. A handle attachment element 1329 can couple the handle 1326 to the gonioscopic optical element 1328. The handle attachment element 1329 can be a C-shaped member, for example, that clamps onto the gonioscopic optical element 1328 with the handle extending therefrom. The arrows in FIG. 13 show how the gonioscope 1325 can be attached to the gonioscopic attachment 1320. For example, as shown by arrow 1370, the handle attachment element 1329 and/or gonioscopic optical element 1328 (e.g., the distal ends thereof) can slide through the open side 1350 and can engage one or more grooves or interface with one or more tabs on the gonioscopic attachment 1320, as discussed herein. As shown by arrow 1372, in some embodiments, the gonioscope 1325 can be inserted into the top or proximal side of the gonioscopic attachment 1320. As discussed herein, the gonioscopic attachment 1320 can have one or more tapered portions (e.g., on the top or proximal side) such that when the gonioscope 1325 (e.g., the gonioscopic optical element 1328 or the handle attachment element 1329 presses on the one or more tapered portions, the gonioscopic attachment 1320 can deform to receive the gonioscope 1325. As shown by arrow 1374, in some embodiments the gonioscope 1325 can be inserted into the gonioscopic attachment 1320 from the bottom or distal side, and the body of the gonioscopic attachment 1320 can flex to receive the gonioscope similar to the insertion of the gonioscope 1325 from the top or proximal side. The gonioscopic attachment 1320 can be similar to, or the same as, any of the various other gonioscopic attachments disclosed herein.

The body 122 can be made of a polymer material, such as plastic. The body 122 can comprise, for example, silicone, silicone derivatives, Acrylonitrile butadiene styrene (ABS), acrylic, acrylic derivatives, biocompatible methacrylates (e.g., poly(methyl methacrylate) (PMMA)), collamer, olefins (e.g., polypropylene), polyimide, combinations thereof, and the like. The retention elements 130 can be made of the same material as the body 122, and can be integrally formed with the body 122. In some embodiments, the body 120 and the retention elements 130 can comprise different materials. For example, the body 120 can comprise a plastic material, while the retention elements 130 can comprise a textile, cloth, or fabric material. Various other materials can be used, in some implementations, such as metal or ceramic materials.

The user can place the gonioscope attached to the gonioscopic attachment 120 on a patient's eye 100. The retention elements 130 engage the eye 100 to retain the gonioscope relative to the eye. A light (e.g., from the microscope) can be directed at a desired angle to the proximal surface 1128A. A user may view portions of the eye 100, such as the anterior chamber 108, through the proximal surface 1128A by using a device such as a microscope, for example.

Engaging the cornea 102 with a gonioscopic attachment may cause trauma to the eye 100. For example, the endothelial cells on the surface of the cornea 102 can be easily damaged and can be more sensitive and/or more fragile than the scleral tissue 104. The retention elements 130 can be configured to not contact the cornea 120 when the gonioscope is positioned for viewing an anterior chamber 108. For example, the retention elements 130 can be configured to position the gonioscope so that at least a portion (e.g., at least about 50%) of the concave distal surface 1225A (e.g., the distal contact surface of the gonioscopic optical element) is spaced apart from the eye (e.g., from the cornea). The retention elements 130 can be configured to position the gonioscope so that at least about 75% of the concave distal surface 1225A is spaced apart from the eye. The retention elements 130 can be configured to position the gonioscope so that the full concave distal surface 1225A is spaced apart from the eye 100. In some embodiments, the gonioscopic attachment 120 can be configured to offset the concave distal surface 1225A from the corresponding surface (e.g., the surface of the cornea 102) on the eye 100, as discussed in connection with FIG. 12.

The retention elements 130 can be disposed on a generally circular path located on the distal surface 124 of the gonioscopic attachment 120. The retention elements 130 can be disposed on a generally circular path that can have a circumference larger than the circumference of the cornea 102, such that the gonioscopic attachment 120 does not contact the cornea 102 during clinical use. The outer circumference of the retention elements 130 can avoid contacting the lid speculum. For example, the outer circumference of the retention elements 130 can comprise an ellipsoid comprising a major axis and a minor axis. The minor axis of the retention elements 130 can be smaller than the distance between the open eyelids, for example. By way of example, the retention elements 130 can be disposed on a generally circular path that has a diameter that is at least about 10 mm, at least about 11 mm, at least about 12 mm, at least about 13 mm, at least about 14 mm, or at least about 15 mm, although values outside these ranged can be used in some implementations. In some embodiments, the retention elements 130 can be disposed on a generally circular path that has a diameter that is less than or equal to about 20 mm, less than or equal to about 15 mm, less than or equal to about 14 mm, less than or equal to about 13 mm, or less than or equal to about 12 mm, although values outside these ranges can be used in some implementations.

Figure 6:
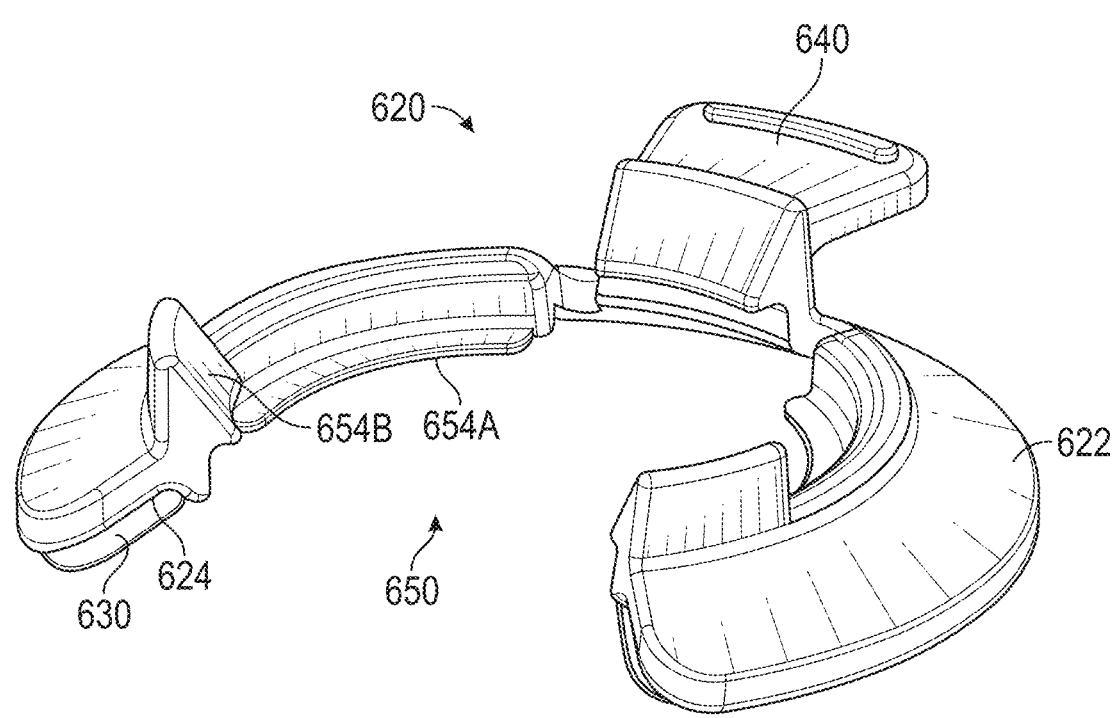
FIG. 6 is a perspective view of an example embodiment of a gonioscopic attachment having a circumferential retention element.

Various different types of retention elements 130 can be used for the gonioscopic attachment 120. FIG. 6 is a perspective view of an example embodiment of a gonioscopic attachment having a circumferential retention element. The gonioscopic attachment 620 can comprise a body 622 (which can be generally C-shaped), at least one circumferential retention element 630 (which can extend at least partially around a circumference defined by the path of the C-shaped body 622), one or more distal tabs 654A (which can restrict or limit movement of the gonioscope in the distal direction relative to the gonioscopic attachment 620), one or more proximal tabs 654B (which can restrict or limit movement of the gonioscope in the proximal direction relative to the gonioscopic attachment 620), an open side 650, and an peripheral tab 640. The body 622 can comprise a distal surface 624.

The body 622 be have a generally C-shaped. The at least one circumferential retention element 630 can be located on the distal surface 624 and extend generally in a distal direction along at least a portion of the circumference of the body 622. The retention element 630 can be a textile, cloth, or fabric material, or any other suitable friction element that is configured to hold the gonioscopic attachment 620 in place relative to the eye when a small amount of distally directed force is applied. Although the retention element 630 is mostly hidden from view in FIG. 6, in some embodiments the retention element 630 (e.g., which can be a textile, cloth, or fabric material) can be generally C-shaped, and in some cases can extend along substantially the full circumferential length of the body 622. The one or more retention elements 630 can be attached to the body 622 using an adhesive or using any other suitable attachment mechanism such as stitching.

The peripheral tab 640 can extend radially outwardly from the body 622. The peripheral tab 640 can be grippable, such as to facilitate positioning of the gonioscopic attachment 620 relative to the gonioscope. For example, the user can manipulate (e.g., pull or push) on the peripheral tab 640 to facilitate attachment or removal of the gonioscopic attachment to or from the gonioscope. In some embodiments, the peripheral tab 640 can extend from one of the proximal tabs 654B. Manipulating the peripheral tab 640 can pull that proximal tab 654B radially outwardly to make room for the gonioscope to be removed from the gonioscopic attachment, or to make room for the gonioscope to be attached thereto. The peripheral tab 640 and the opening 650 can be located on opposite sides of one another. The peripheral tab 640 can be configured to point generally towards a patient's nasal duct during use. The body 622 can be configured to surround and clamp a portion of a gonioscope, as discussed herein. The one or more distal tabs 654A can be configured to prevent a gonioscope from coming off of the gonioscopic attachment 620 in the distal direction. The one or more proximal tabs 654B can be configured to prevent a gonioscope from coming off of the gonioscopic attachment 620 in the proximal direction. In some embodiments, the one or more proximal tabs 654B can have a tapered or slanted proximal surface, such that when the gonioscope is pressed distally into the gonioscopic attachment 620, the one or more proximal tabs 654B can be displaced radially outwardly to make room for the gonioscope to move past the proximal tabs 654B into the attached position. A limited contact area between a gonioscopic retention device and the patient's eye can reduce the trauma to the eye. Retention elements of a gonioscopic device can also elevate portions of a gonioscope and align the gonioscope at an angle from the curvature of the eye to provide a user with a desired viewing angle. A gonioscopic device can comprise an access path to allow surgical procedures while using the gonioscope. For example, as shown and discussed herein, at least some of the retention elements can be disposed on one or more arms, which can elevate the gonioscope and/or gonioscopic attachment, which can provide space for medical instruments such as those used for eye surgery (e.g., placement of a stent in the trabecular meshwork).

Figure 2:
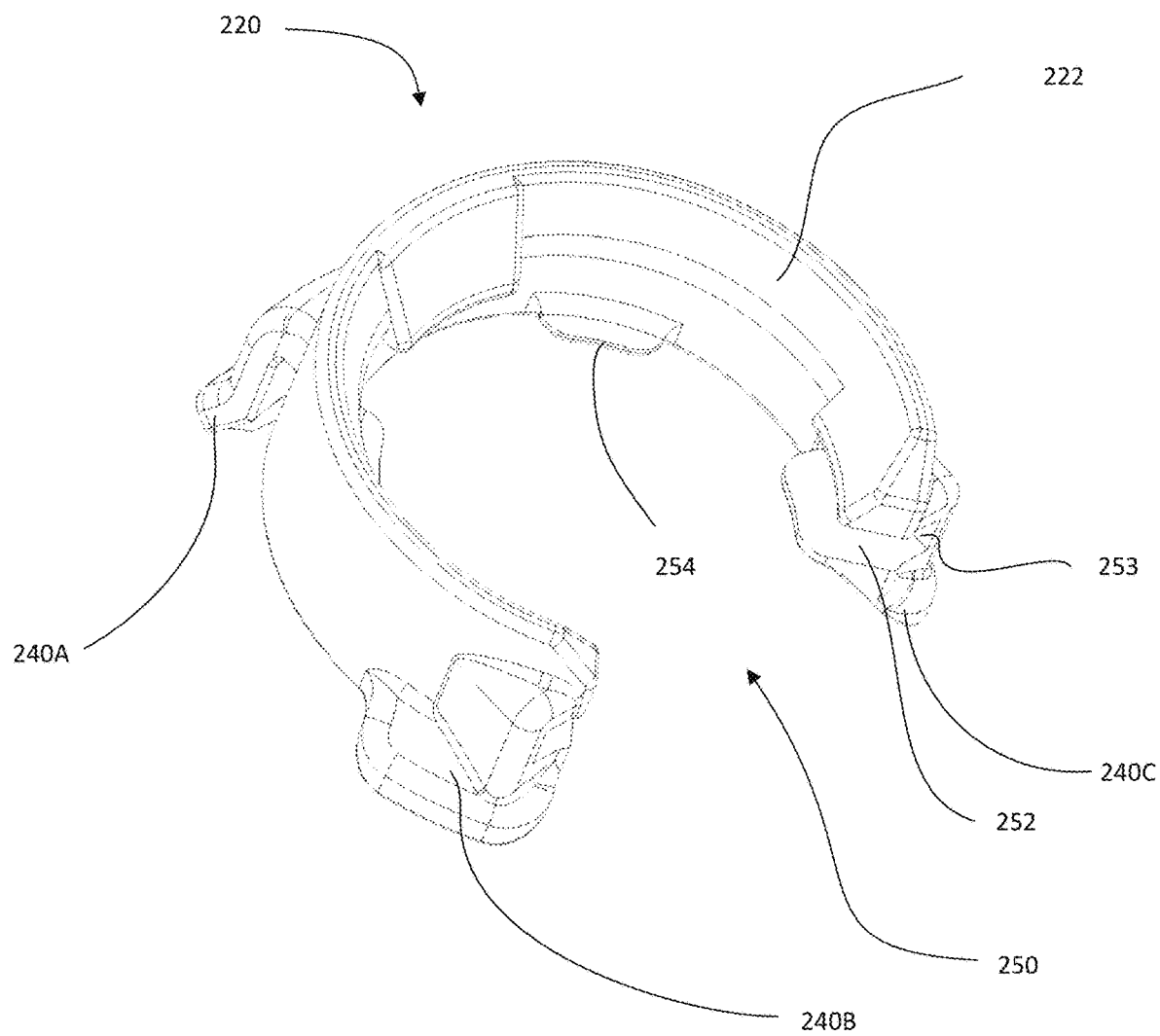
FIG. 2 is a detailed perspective view of an example embodiment of a gonioscopic attachment.

FIG. 2 is a detailed perspective view of an example embodiment of a gonioscopic attachment. The gonioscopic attachment 220 can include a body 222, a plurality of arms 240A, 240B, 240C, a groove 252, a plurality of tabs 254, and an open side 250. The plurality of arms can comprise a first arm 240A, a second arm 240B, and a third arm 240C. The groove 252 can comprise a sidewall 253.

The body 222 can be configured to removably attach to a gonioscope. The plurality of arms 240A, 240B, 240C can extend from the body and can include retention elements configured to engage an eye to retain the gonioscope relative to the eye. The arms 240A-C can extend distally and/or radially outward so that the retention elements to not contact the cornea during use (e.g., instead engaging the sclera of the eye). The first arm 240A can extend from on or near the middle section of the body 222 (e.g., at or near the apex of the generally C-shaped body 222). The first arm 240A can generally point to a nasal duct of the patient during use. The first arm 240A can be configured to engage a nasal side of the eye during use, such as for use during a surgical operation in which a stent is inserted through an incision on the temporal side of the eye and implanted into the nasal side of the eye. Other orientations are possible. For example, the gonioscopic attachment can be oriented with the first arm 240A to engage the temporal side of the eye, such as during a surgical operation in which a temporal implantation is inserted through a nasal corneal incision.

The first arm 240A can have sufficient length to engage the eye (e.g., the sclera) at an area that is spaced apart from the cornea by a distance such that the retention elements on the arm 240A do not interfere with a surgical placement of a stent near the edge of the cornea on the nasal side (e.g., in the trabecular meshwork). In some instances, if the retention elements were disposed too close to the location of the stent implantation, the retention elements could produce a backstop that could interfere with, or make more difficult, the stent implantation. During an example stent implantation, a tool can be inserted into the eye near the temporal side of the cornea. The open side 250 of the body can face the temporal side during use, and the open side 250 can facilitate insertion of the tool for the stent implantation. The stent can be advanced to the nasal side of the cornea where it can be implanted (e.g., in the trabecular meshwork).

By way of example, the first arm 240A can have sufficient length to engage the eye (e.g., the sclera) at an area that is spaced apart from the cornea by a distance that is at least about 0.5 mm, at least about 0.75 mm, at least about 1 mm, at least about 1.5 mm, at least about 2 mm, at least about 3 mm, at least about 4 mm, at least about 5 mm, or more. The distance can also be less than or equal to about 15 mm, less than or equal to about 12 mm, less than or equal to about 10 mm, less than or equal to about 8 mm, less than or equal to about 6 mm, less than or equal to about 5 mm, less than or equal to about 4 mm, less than or equal to about 3 mm, or less. The gonioscopic attachment 220 can be configured to position the retention elements on at least a portion of the nasal side so that all the retention elements are spaced away from the corresponding nasal end of the gonioscope by a distance of at least about 5 mm, at least about 7.5 mm, at least about 10 mm, at least about 12.5 mm, at least about 15 mm, or more. The distance can also be less than or equal to about 30 mm, less than or equal to about 20 mm, less than or equal to about 15 mm, or less. In some implementations, values outside these ranges can be used.

The gonioscopic attachment 220 can include one or more engagement features configured to engage one or more corresponding features on the gonioscope. By way of example, the gonioscopic attachment 220 can have a groove 252, which can be located near the open side 250. The groove 252 can be configured to slidably accept a corresponding feature of a gonioscope. For example, the groove 252 can be shaped and sized to accept a handle attachment element 1129 shown in FIG. 11. The plurality of tabs 254 can engage portions of the gonioscope (e.g., the handle attachment element 1129) and prevent the gonioscopic attachment 220 from coming off the gonioscope during use. A user may slide the gonioscope (e.g., the handle attachment element 1129) through the groove 252. The body 222 can deflect to accept the gonioscope (e.g., the handle attachment element 1129) as the open side 250 temporarily widens, and at least partially return towards its unflexed shape once the gonioscope (e.g., the handle attachment portion 1129) is fully inserted and clamped onto the body 222. In some embodiments, the body 222 can remain partially flexed when the gonioscope is fully inserted, such that the body 222 applies a force and squeezes against the gonioscope. The open side 250 may provide access for a tool or applicator to be inserted, for example, to insert hardware such as a stent into the eye. In some embodiments, the body 222 of the gonioscopic attachment 220 can have a closed shape instead of the C-shaped shown in FIG. 2 (e.g., extending across a circumferential angle of a full 360 degrees). The body 222 can extend across a circumferential angle of about 180 degrees, about 210 degrees, about 240 degrees, about 270 degrees, about 300 degrees, about 330 degrees, about 360 degrees, or any value in the ranges between the identified angles. In some embodiments, the open side 250 can be omitted, such as for use in a procedure in which entry to the eye is unnecessary (e.g., SLT or ALT procedures).

Figure 3:
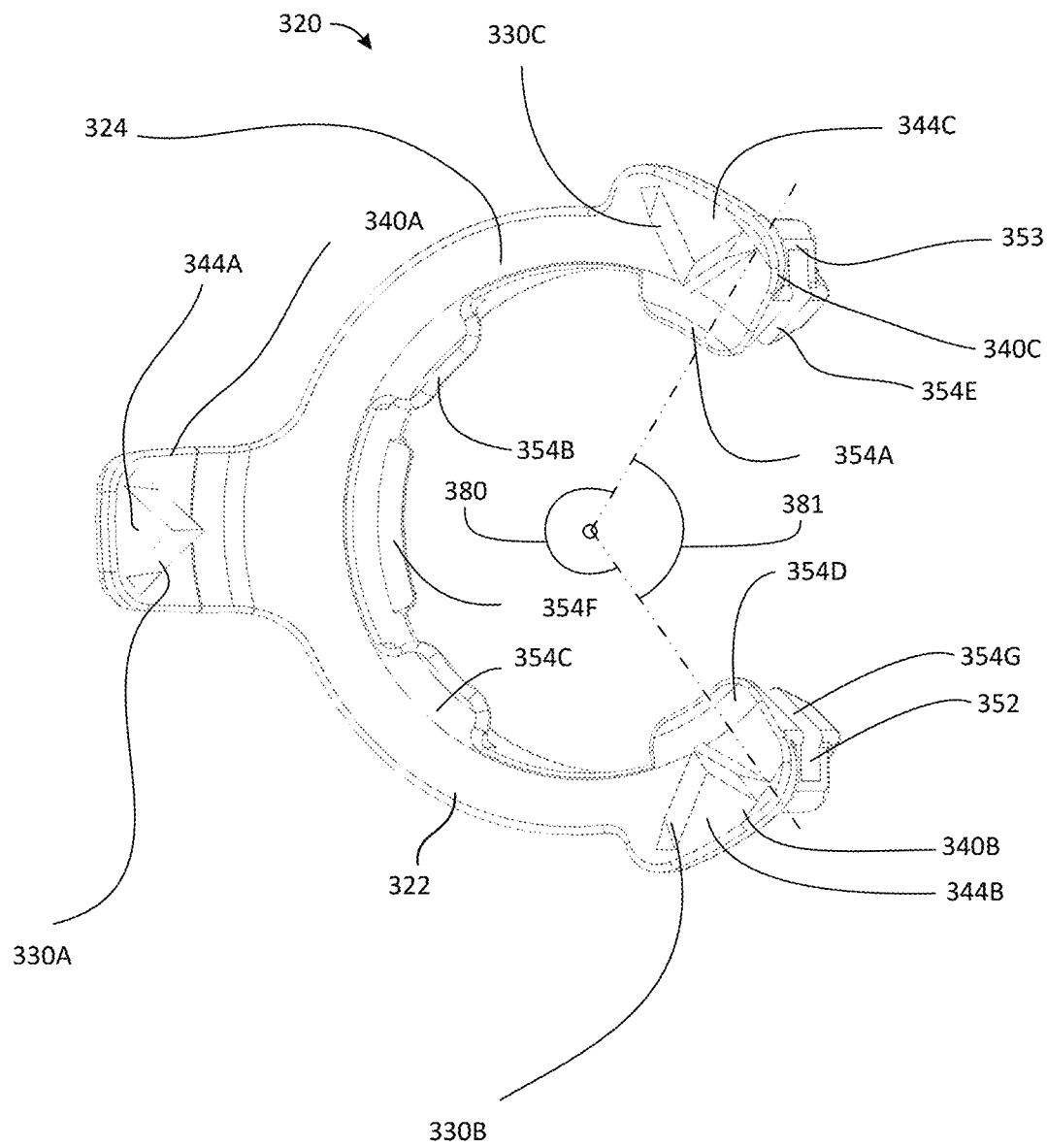
FIG. 3 is a bottom view of an example embodiment of a gonioscopic attachment.

A gonioscopic attachment can comprise or more arms extending distally and/or radially outward from the body, and the one or more arms can have the retention elements. The retention elements can be disposed on a distal portion of the one or more arms. FIG. 3 is a bottom view of an example embodiment of a gonioscopic attachment. The gonioscopic attachment can comprise a body having a distal surface 324.

The gonioscopic attachment can have one or more arms, such as a first arm 340A, a second arm 340B, and a third arm 340C. Although various example embodiments are shown and described as having three arms, a different number of arms can be used. In some embodiments, the gonioscopic attachment can have a single arm (e.g., arm 340A), and one or more of the retention elements can be disposed on the distal side of the body 322. In some embodiments, two, four, five, or any other suitable number of arms can be used. The arms 340A, 340B, 340C can be positioned to distribute the retention elements around the gonioscope across a circumferential angle 380. The first arm 340A can comprise a first distal portion 344A and a first atraumatic retention element 330A located on the first distal portion 344A. The second arm 340B can comprise a second distal portion 344B and a second atraumatic retention element 330B located on the second distal portion 344B. The third arm 340C can comprise a third distal portion 344C and a third atraumatic retention element 330C located on the third distal portion 344C. The gonioscopic attachment can comprise one or more distal tabs, one or more proximal tabs, and a sidewall 353 can be formed in between. The one or more distal tabs can comprise a first distal tab 354A, a second distal tab 354B, a third distal tab 354C, and a fourth distal tab 354D. The one or more distal tabs can be configured to prevent the gonioscope from moving distally relative the gonioscopic attachment 320, when attached thereto. The one or more proximal tabs can comprise a first proximal tab 354E, a second proximal tab 354F, and a third proximal tab 354G. The one or more proximal tabs can be configured to prevent the gonioscope from moving proximally relative to the gonioscopic attachment 320 when attached thereto.

The one or more arms 340A, 340B, 340C can be configured to position the gonioscopic attachment and the gonioscope so that at least a portion of the concave distal surface 1225A of the gonioscope (not shown in FIG. 3) can be spaced apart from the eye. The one or more arms 340A, 340B, 340C can be configured to position the gonioscopic attachment and the gonioscope so that at least about 50% of the concave distal surface 1225A can be spaced apart from the eye. The one or more arms 340A, 340B, 340C can be configured to position the gonioscopic attachment and the gonioscope so that at least about 75% of the concave distal surface 1225A can be spaced apart from the eye, or so that the concave distal surface 1225A is fully separated from the eye and does not directly contact the eye. In some implementations, index matching gel can be disposed between the eye and the concave distal surface 1225A of the gonioscope.

The retention elements 330A-C can be positioned to be distributed around the gonioscope across a circumferential angle 380 of at least about 220 degrees, at least about 230 degrees, at least about 250 degrees, at least about 270 degrees, at least about 290 degrees, or more. For example, the one or more arms 340A, 340B, 340C can be positioned to distribute the retention elements 330A-C around the gonioscope across the circumferential angle 380. In some embodiments, the retention elements 330A-C can be positioned to be distributed around the gonioscope across a circumferential angle 380 of less than or equal to about 320 degrees, less than or equal to about 310 degrees, less than or equal to about 290 degrees, less than or equal to about 270 degrees, less than or equal to about 250 degrees, or less. In some embodiments, the retention elements 330A-C can be positioned to be distributed around the gonioscope across a circumferential angle 380 of about 270 degrees.

The retention elements 330A-C can be positioned to be distributed around the gonioscope such that each gap between adjacent retention elements has a circumferential angle 381 that is less than or equal to about 145 degrees, less than or equal to about 135 degrees, less than or equal to about 120 degrees, less than or equal to about 105 degrees, less than or equal to about 90 degrees, less than or equal to about 75 degrees, less than or equal to about 60 degrees, or less. The retention elements 330A-C can be positioned to be distributed around the gonioscope such that at least one of the gaps between adjacent retention elements has a circumferential angle that is at least about 60 degrees, at least about 75 degrees, at least about 90 degrees, at least about 105 degrees, at least about 120 degrees, or more. The retention elements 330A-C can be distributed to restrain movement of the gonioscopic attachment 320 relative to the eye in various different directions.

The plurality of distal tabs 354A, 354B, 354C, 354D can prevent a gonioscope from moving distally once the gonioscope is clamped in. The plurality of proximal tabs 354E, 354F, 354G can prevent a gonioscope from moving proximally once the gonioscope is clamped in. One or more of the plurality of proximal tabs 354E, 354F, 354G can comprise a proximally tapered surface. The proximally tapered surface of the proximal tabs 354E, 354F, 354G can be configured to accept a portion of a gonioscope by sliding the gonioscope into the gonioscopic attachment from the proximal direction.

Figure 5:
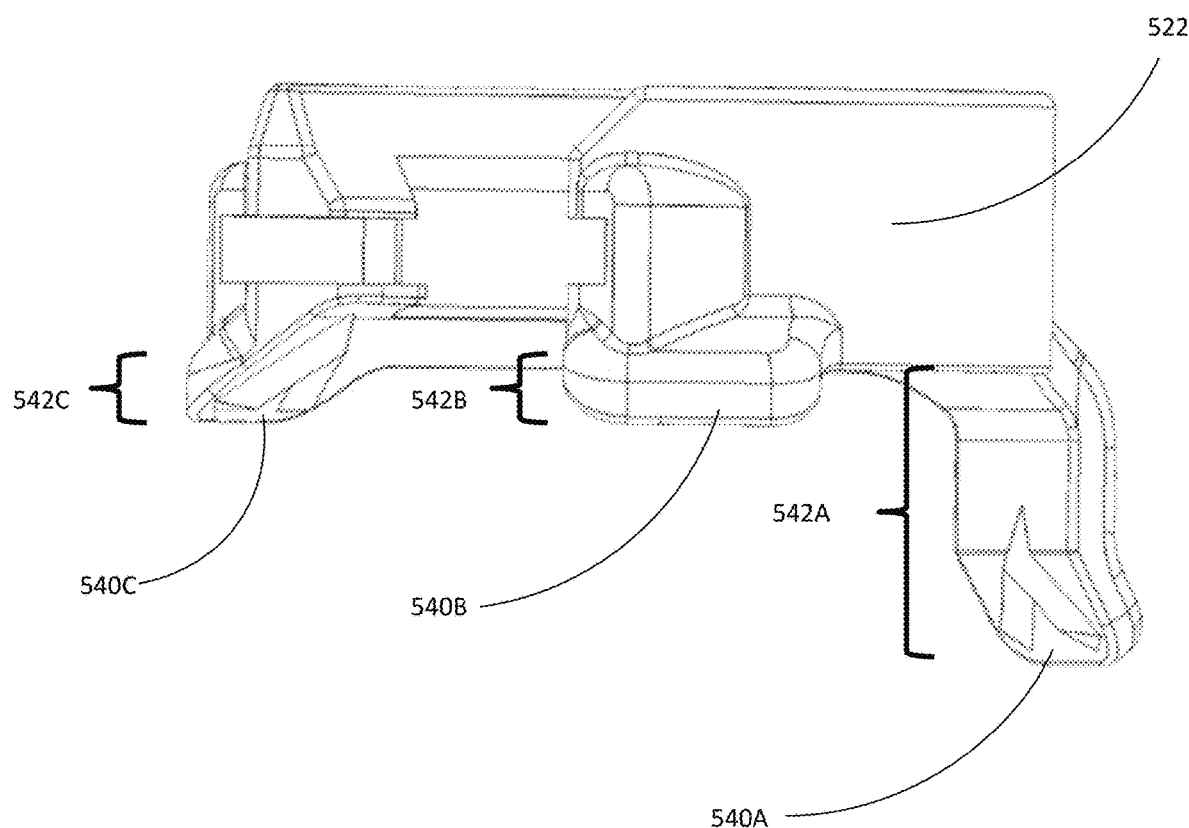
FIG. 5 is a detailed side view of an example embodiment of a gonioscopic attachment.

The arms of the gonioscopic attachment can comprise different distances from the body. FIG. 5 is a detailed side view of an example embodiment of a gonioscopic attachment. The second arm 540B can extend distally from the body 522 by a second distance 542B. The first arm 540A can extend distally from the body 522 by a first distance 542A that is greater than the second distance 542B. The gonioscopic attachment can have a third arm 540C extending distally from the body 522 by a third distance 542C, which can be substantially the same as the second distance 542B, and at least one of the retention elements can be disposed on the third arm 540C. The first distance 542A can be at least about 1.2 times the second distance 542B and/or the third distance 542C. The first distance 542A can be at least about 1.5 times the second distance 542B and/or the third distance 542C. The first distance 542A can be at least about 2 times larger than the second distance 542B and/or the third distance 542C. The first distance 542A can be at least about 3 times larger than the second distance 542B and/or the third distance 542C. The first distance 542A can be at least about 20% larger, about 50% larger, about 100% larger (e.g., double), about 120% larger, about 150% larger, about 200% larger, about 300% larger, about 400% larger, about 500% larger, about 700% larger, about 1,000% larger, about 1,500% larger, or more than the second distance 542B and/or the third distance 542C, although other values can be used in some implementations. The first distance 542A can be larger than the second distance 542B and/or the third distance 542C by any range bounded by any combination of the values listed above. In some embodiments, the arm 540A can have a length of at least about 3 mm, at least about 5 mm, at least about 7.5 mm, at least about 10 mm, at least about 12.5 mm, at least about 15 mm, or more. The arm 540A can have a length that is less than or equal to about 40 mm, less than or equal to about 30 mm, less than or equal to about 20 mm, less than or equal to about 15 mm, less than or equal to about 10 mm, or less. Values outside these ranges can be used in some implementations.

The gonioscopic attachment can align a gonioscopic optical element at a desired viewing angle. For example, in certain situations, a user may want the gonioscope to be elevated and tilted at an angle away from the corneal surface

Figure 4:
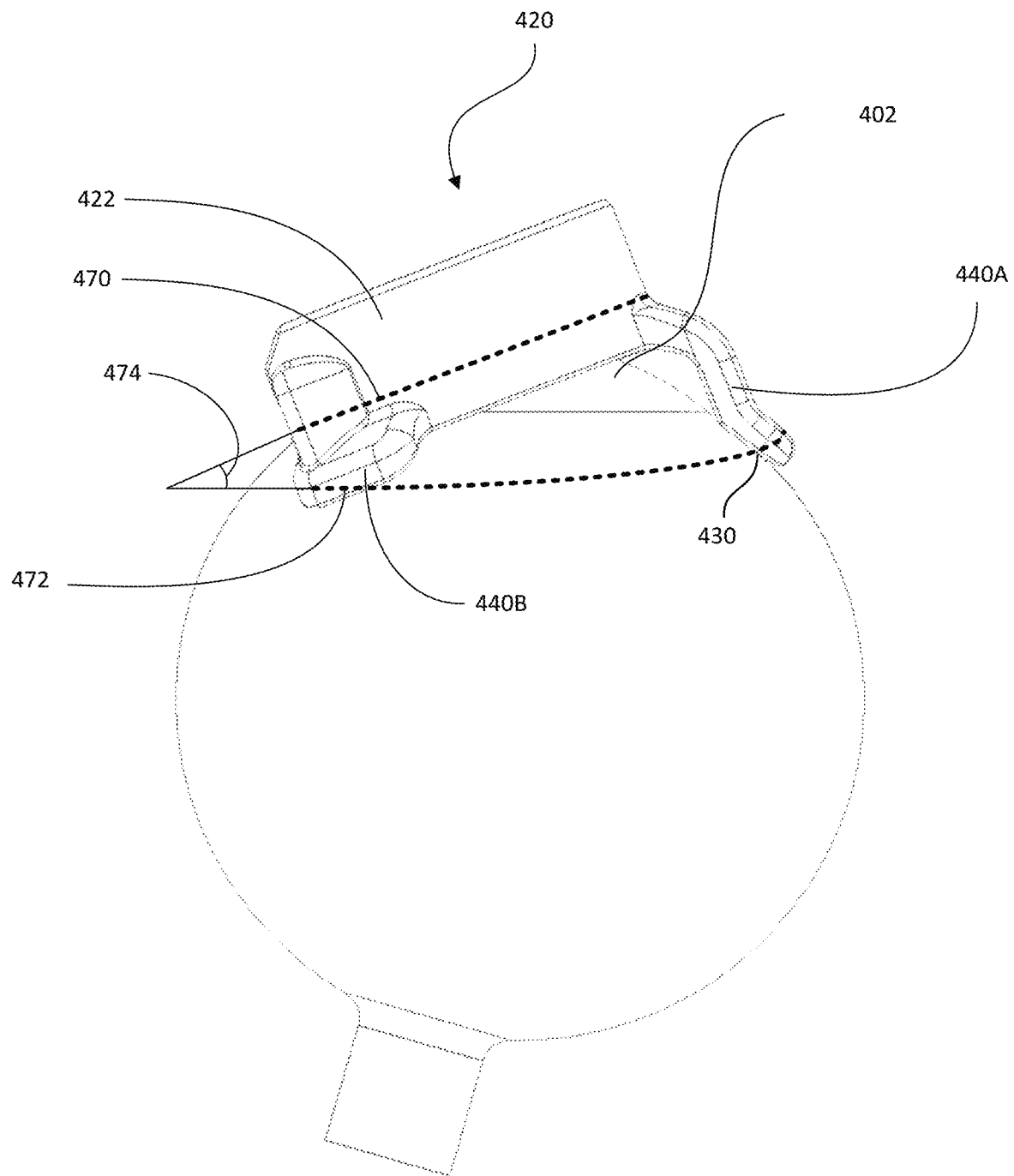
FIG. 4 is a side view of an example embodiment of a gonioscopic attachment on a patient's eye.

402. FIG. 4 is a side view of an example embodiment of a gonioscopic attachment on a patient's eye. The gonioscopic attachment can comprise a body 422 comprising a plurality of engagement features configured to engage one or more corresponding features on the gonioscope to secure the gonioscopic attachment 420 to the gonioscope. The gonioscope is omitted from view in FIG. 4, but it is to be understood the gonioscope would be attached to the gonioscopic attachment 420 during use. The body 422 can be configured to engage the gonioscope at locations that are disposed on a first generally circular path 470. For example, the engagement features (e.g., the groove 352 and the one or more tabs 354) can be disposed on the first generally circular path 470. The plurality of retention elements 430 can be disposed on a second generally circular path 472. The second generally circular path 472 can be offset from the first generally circular path 470 by a circular path offset angle 474. The circular path offset angle 474 can be between about 5 degrees and about 30 degrees, although angles outside this range can be used in some implementations. The circular path offset angle can be between about 10 degrees and about 20 degrees. The offset angle can be about 17 degrees, in some embodiments. As can be seen in FIG. 4, the arm 440A can be configured to elevate the corresponding side of the gonioscopic attachment 420. For example, the arm 440A can be longer than the arm 440B, as discussed herein, such that the side of the gonioscopic attachment 420 having the arm 440A can be elevated further above the eye than the side of the gonioscopic attachment 420 having the arm 440B.

Figure 12:
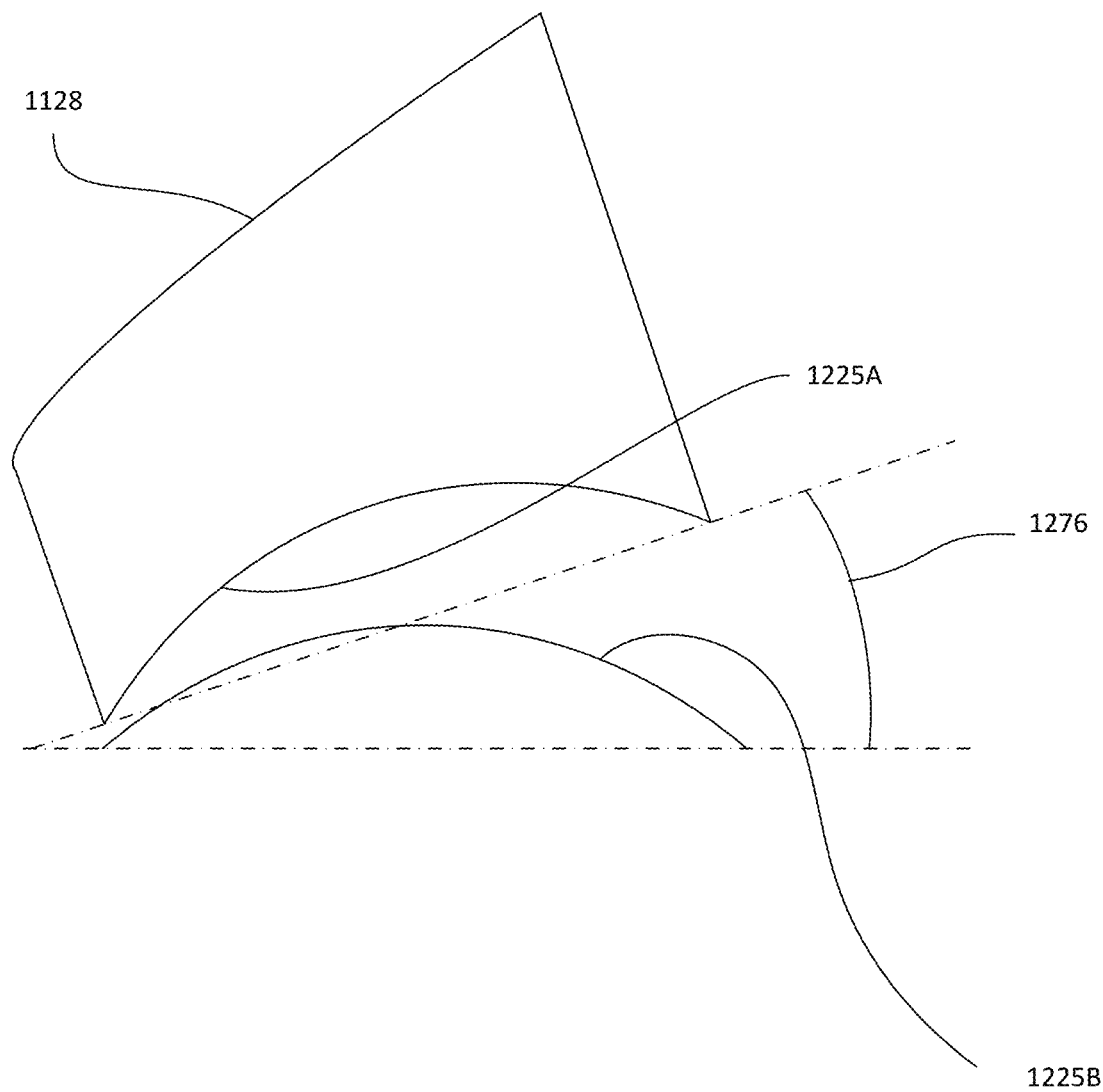
FIG. 12 is a schematic drawing showing an example curvature offset angle between a distal surface curvature of the gonioscope and the corresponding curvature of the eye.

FIG. 12 is a schematic drawing showing an example curvature offset angle between a distal surface curvature of the gonioscope and the corresponding curvature of the eye. A gonioscopic attachment can comprise a plurality of retention elements. The plurality of retention elements, which can be disposed on the arms 340A, 340B, 340C shown and described in reference to FIG. 3 or on the arms of other embodiments disclosed herein, can be configured to position the gonioscope so that all or part of the concave distal surface 1225A is spaced apart from the eye. A gonioscope can have a gonioscopic optical element that has a concave distal surface 1225A that corresponds to the curvature of the eye 1225B (e.g., the curvature of the cornea). A gonioscopic attachment can comprise a plurality of retention elements that are configured to position the gonioscope so that the curvature of the concave distal surface 1225A is offset from a corresponding curvature of the eye (e.g., of the cornea) by a curvature offset angle 1276. The curvature offset angle 1276 can be between about 3 degrees and about 20 degrees, or any range contained therein, although values outside this range can be used in some implementations. The curvature offset angle 1276 can be between about 5 degrees and about 17 degrees, between about 7 degrees and about 15 degrees. The curvature offset angle 1276 can be about 10 degrees.

The plurality of retention elements can be configured to engage the eye without causing trauma to the eye. The retention elements can comprise an atraumatic shape. The atraumatic retention elements can have a shape that is sufficiently blunt that the retention elements do not pierce or cause other trauma to the eye when pressed against the eye (e.g., against the sclera), while also restraining movement between the eye and the gonioscopic attachment. For example, the atraumatic retention elements can include protrusions that can be pressed against the tissue of the eye (e.g., the sclera) to deform the tissue of the eye without piercing into the tissue of the eye. The retention element structures that are configured to engage the eye can have a minimum radius of curvature of about 0.002 inches or more, of about 0.003 inches or more, of about 0.004 inches or more, of about 0.005 inches or more, of about 0.007 inches or more, of about 0.009 inches or more, of about 0.01 inches or more, or of about 0.012 inches or more. The retention element structures that are configured to engage the eye can have at least a portion with a radius of curvature that is less than or equal to about 0.02 inches, less than or equal to about 0.015 inches, less than or equal to about 0.012 inches, less than or equal to about 0.01 inches, less than or equal to about 0.009 inches, less than or equal to about 0.008 inches, less than or equal to about 0.007 inches, less than or equal to about 0.006 inches, or less than or equal to about 0.0057 inches. Values outside these ranges can be used for the radii of curvature on the retention elements, in some implementations.

Figure 7A:
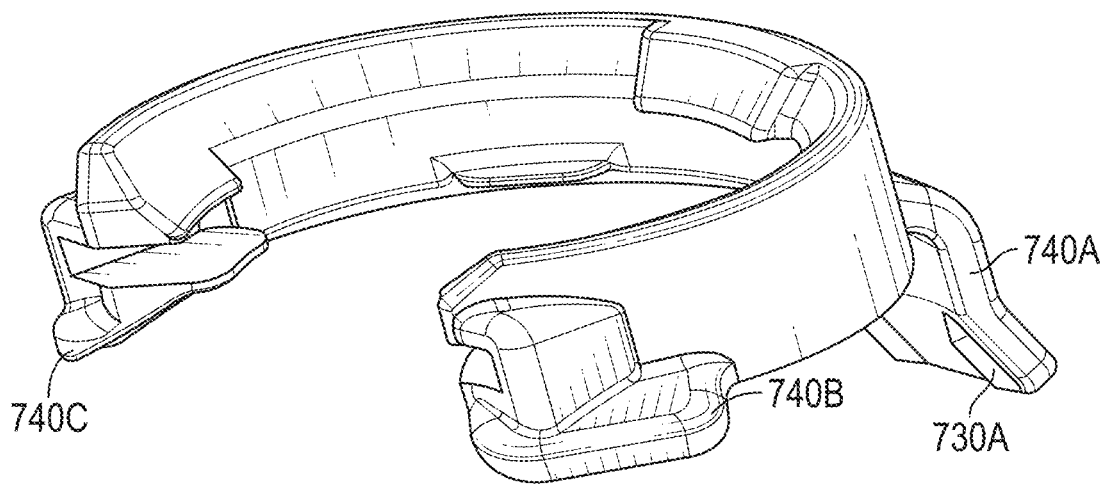
FIGS. 7A and 7B are perspective views of an example embodiment of a gonioscopic attachment.
Figure 7B:
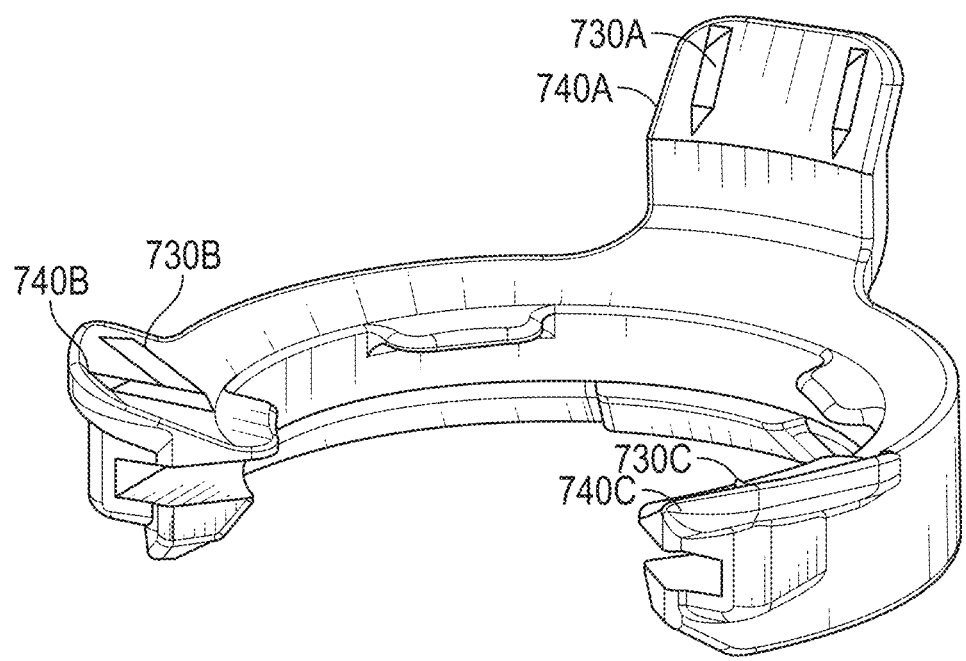
Figure 8A:
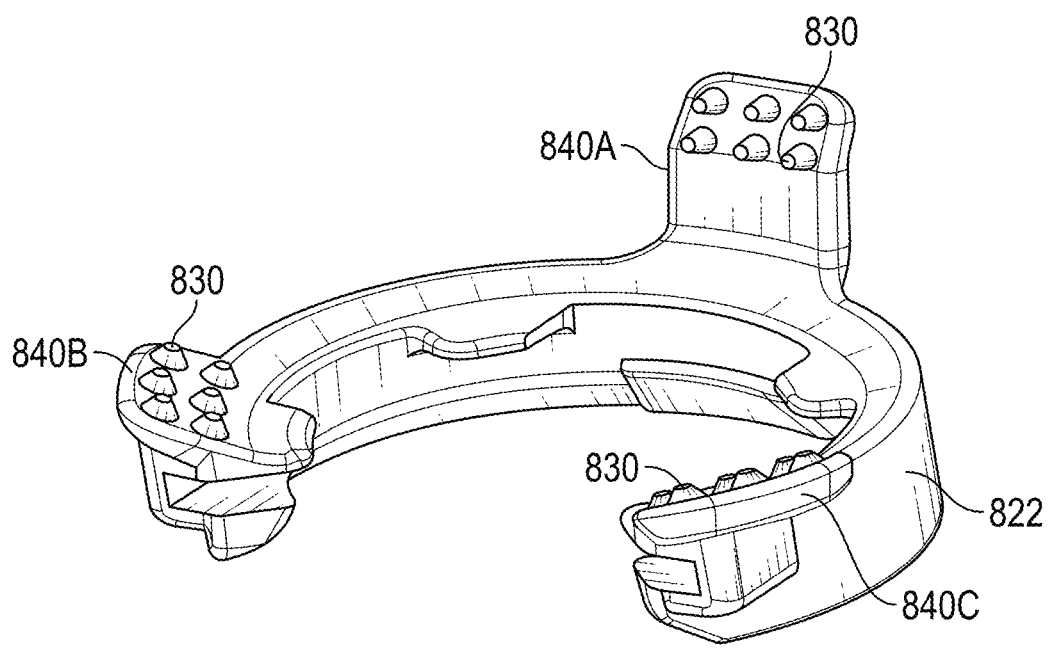
FIG. 8A is a bottom view of an example embodiment of a gonioscopic attachment comprising frustoconical shaped atraumatic retention elements.

The retention elements 330A, 330B, 330C shown and described in reference to FIG. 3 can have generally V-shaped retention elements. In some embodiments, retention elements having different shapes can be used on one gonioscopic attachment. The retention elements can be one or more ridges (e.g., parallel or V-shaped), one or more cleats, etc. For example, an example embodiment of a gonioscopic attachment shown in FIGS. 7A and 7B can have a first arm 740A, a second arm 740B, and a third arm 740C. The first arm can have a first retention element 730A having two parallel ridges. The second arm 740B can comprise a second retention element 730B having generally a V-shape. The third arm 740C can comprise a third retention element 730C. FIG. 8A shows an example embodiment in which the retention elements 830 are cleats. The retention elements can have a generally frustoconical shape. FIG. 8A shows six cleats 830 on each of the first arm 840A, the second arm 840B, and the third arm 840C. Various different numbers of cleats 830 can be used. For example, each of the arms 840A, 840B, and/or 840C (or any other suitable location on the gonioscopic attachment) can have one, two, three, four, five, six, eight, ten, fifteen, twenty cleats 830, or more or any range bounded by any of the values listed above. The retention features (e.g., cleats 830) can be integrally formed with the body 822 of the gonioscopic attachment. Many variations are possible. The retention elements can have a generally frustoconical cross-section along an elongated frustoconical ridge shape. In some embodiments, the retention elements can include fabric, cloth, or textile material, or other friction elements configured to engage the eye to restrain movement of the gonioscope and/or gonioscopic attachment relative to the eye. In some embodiments, one or more of the arms 840A, 840B, 840C can be omitted. For example, the retention features (e.g., cleats 830) can be disposed on the body 822 of the gonioscopic attachment, which can be C-shaped.

Figure 8B:
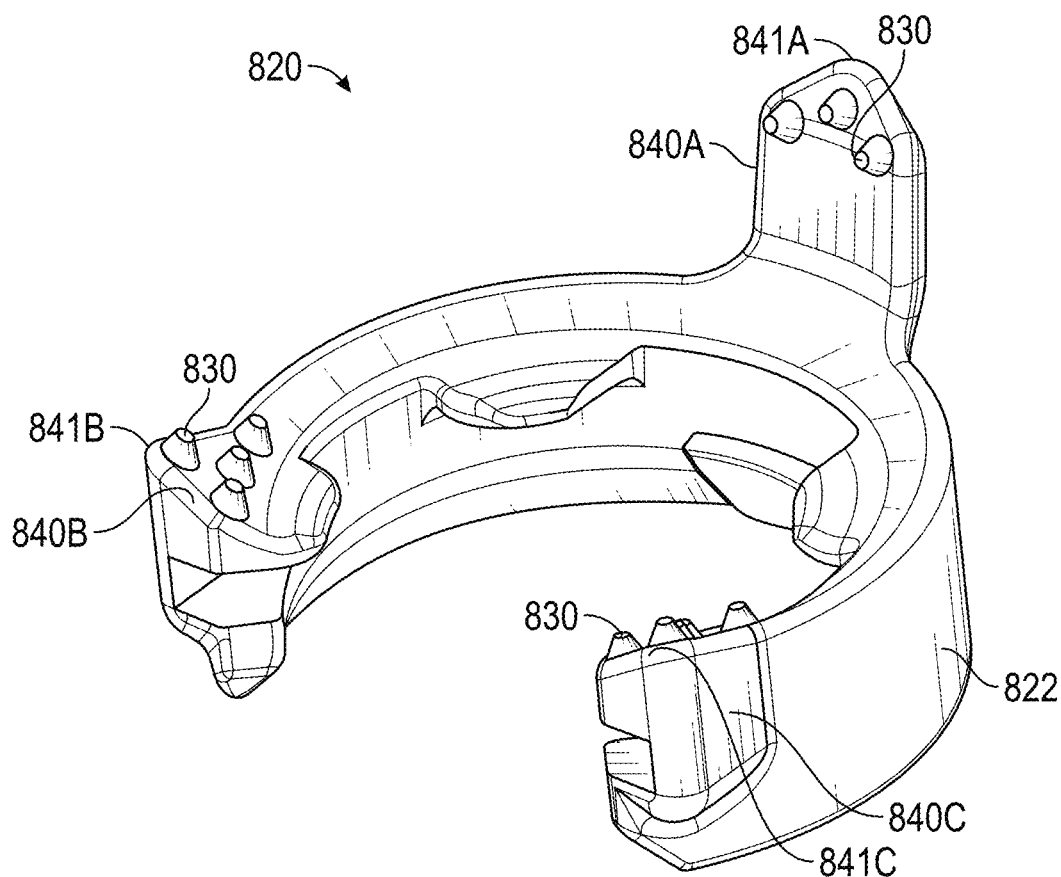
FIG. 8B shows a perspective view of an underside of an example embodiment of a gonioscopic attachment that can be configured to slide under tissue adjacent to the eye of the subject, such as under the eyelid.
Figure 8C:
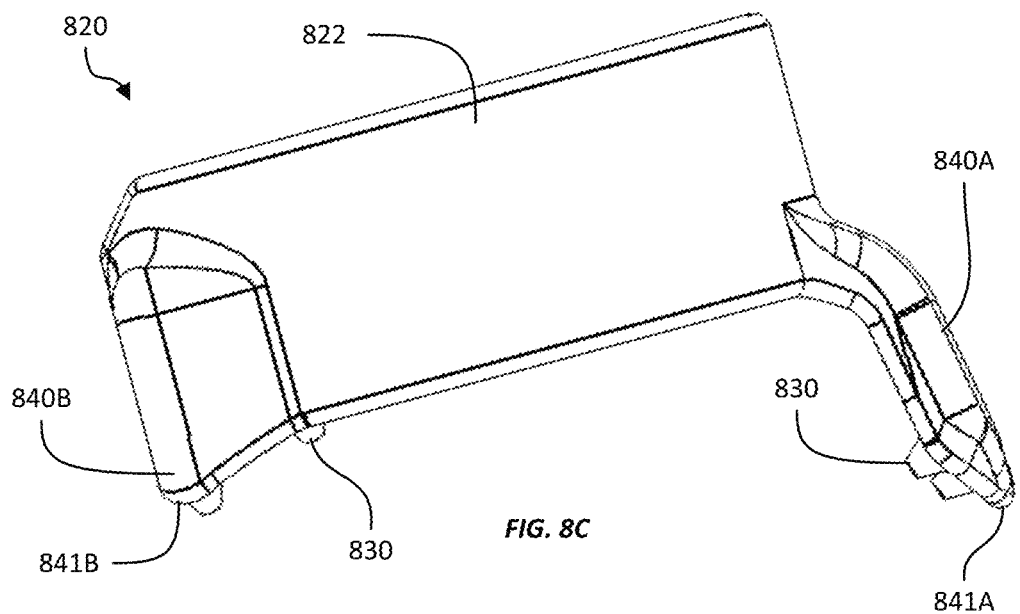
FIG. 8C shows a side view of the gonioscopic attachment of FIG. 8B.
Figure 8D:
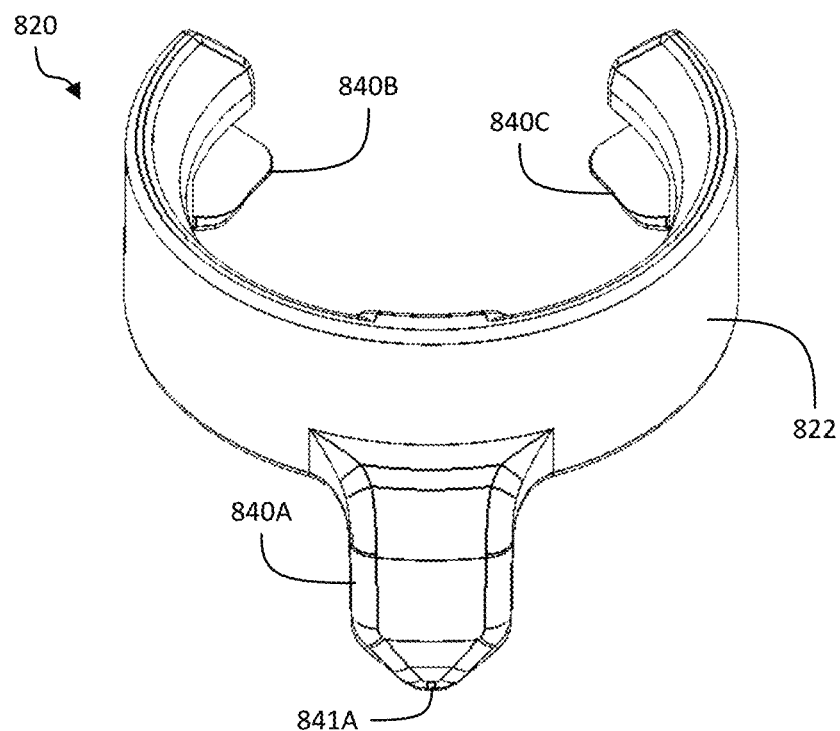
FIG. 8D shows a top view of the gonioscopic attachment of FIG. 8B.

In some situations the eye of the subject can move while the gonioscope and/or gonioscopic attachment is contacting the eye. For example, the subject might move the eye, and the gonioscope and/or gonioscopic attachment can move along with the eye, especially if retention features are engaged with tissue of the eye (e.g., tissue of the sclera). Also, a medical practitioner may move the eye (e.g., during a surgery or other medical procedure). For example, when the retention features are engaged with the eye (e.g., with the sclera) a medical practitioner can manipulate the gonioscope in order to move the eye to a desired position, like operating a joystick. As the eye moves, if the gonioscope and/or gonioscope attachment bumps into the tissue surrounding the eye (e.g., the eyelid), the gonioscope can be moved relative to the eye, which can interfere with imaging inside the eye. Also, the tissue adjacent the eye can limit the range of motion of the gonioscope, which can impede the medical practitioner from positioning the gonioscope at a desired position, if the desires position would cause the gonioscope and/or gonioscopic attachment to bump into or press against the tissue adjacent to the eye. FIG. 8B shows a perspective view of an underside of an example embodiment of a gonioscopic attachment 820 that can be configured to slide under tissue adjacent to the eye of the subject, such as under the eyelid. FIG. 8C is a side view of the gonioscopic attachment 820 of FIG. 8B. FIG. 8D is a top view of the gonioscopic attachment 820 of FIG. 8B. The features described in connection with FIGS. 8B-8D can be incorporated into the other example embodiments for gonioscopes and gonioscopic attachments disclosed herein. One or more of the arms 840A, 840B, and/or 840C can be configured to side under tissue adjacent to the eye when pressed against the tissue. For example, the arm 840A can have a distal end 841A that is tapered, so that when the distal end 841A of the arm 840A moves into contact with the eyelid or other tissue adjacent to the eye, the arm 840A can slide under the eyelid. As can be seen in FIG. 8C, the thickness of the arm 840A can decrease towards the distal end 841A. Accordingly, the distal end 841A of the arm 840A can be tapered in one or two different dimensions (e.g., the dimension shown in FIG. 8C and/or the dimension shown in FIG. 8D). In some embodiments, the features described in connection with the distal end 841A of the arm 840A can also apply to the distal end 841B of the arm 840B and/or to the distal end 841C of the arm 840C.

One or more of the ends 841A, 841B, and/or 841C can be tapered to a rounded point. The rounded point can be sharp enough the slide under the eyelid or other tissue adjacent the eye when the gonioscope is pressed against the tissue, and the rounded point can be sufficiently rounded so as to not puncture or cut the eye or the surrounding tissue. For example, the rounded point can have a minimum radius of curvature of about 0.002 inches or more, of about 0.003 inches or more, of about 0.004 inches or more, of about 0.005 inches or more, of about 0.007 inches or more, of about 0.009 inches or more, of about 0.01 inches or more, of about 0.012 inches or more, of about 0.015 inches or more, of about 0.02 inches or more, of about 0.03 inches or more, of about 0.05 inches or more. The rounded point can have a radius of curvature that is less than or equal to about 0.1 inches, less than or equal to about 0.075 inches, less than or equal to about 0.05 inches, less than or equal to about 0.03 inches, less than or equal to about 0.02 inches, less than or equal to about 0.015 inches, less than or equal to about 0.012 inches, less than or equal to about 0.01 inches, less than or equal to about 0.009 inches, less than or equal to about 0.008 inches, less than or equal to about 0.007 inches, less than or equal to about 0.006 inches, or less than or equal to about 0.0057 inches. Values outside these ranges can be used in some implementations.

A gonioscope optical element can include an optical fixation point. The optical fixation point can be located in the optical path of a patient. Optical fixation points can be used to help a patient orient their eye to align with the gonioscopic optical element and/or a microscope. The fixation point can be used with the gonioscopic attachments described above during procedures and treatments such as, for example, glaucoma surgery (e.g., minimally invasive glaucoma surgery (MIGS), laser trabeculoplasty (e.g., SLT/ALT), fundus laser, vitrectomy laser, and suture lysis optics where ocular retention and eye/lens stabilization would be beneficial. The fixation point can be actively illuminated (LED) or passively illuminated (e.g., with light emitted from a microscope light). Multiple fixation points differentiated via color and/or shape may allow a user, such as a physician or other medical practitioner, to further refine the patient's eye orientation. An optical fixation point can be used to orient the eye of the patient. Multiple optical fixation points can be used to further help orient the eye to the gonioscopic optical element.

FIGS. 9A to 9E are schematic drawings of different views of some example embodiments of a gonioscopic fixation point used with a gonioscopic optical element. The gonioscopic optical element 928 can comprise a proximal surface 928A and a distal surface 928B. In some embodiments, the gonioscopic optical element 928 can include a thick side 928C, and a thin side 928D. The gonioscopic fixation point 960 can be configured to be visible to the subject when the gonioscope is positioned on the eye. The gonioscopic fixation point 960 can be located on the thick side 928C of the gonioscopic optical element 928. The location of the gonioscopic fixation point 960 can be configured to provide a desired viewing angle (e.g., for a medical practitioner to use in examining and/or operating on the patient's eye). For example, the location of the gonioscopic fixation point 960 can be such that when a patient looks directly at the gonioscopic fixation point 960, the medical practitioner can view a desired structure of the inside of the eye (e.g., the anterior chamber angle) through the proximal surface of the gonioscopic optical element 928.

Figure 10A:
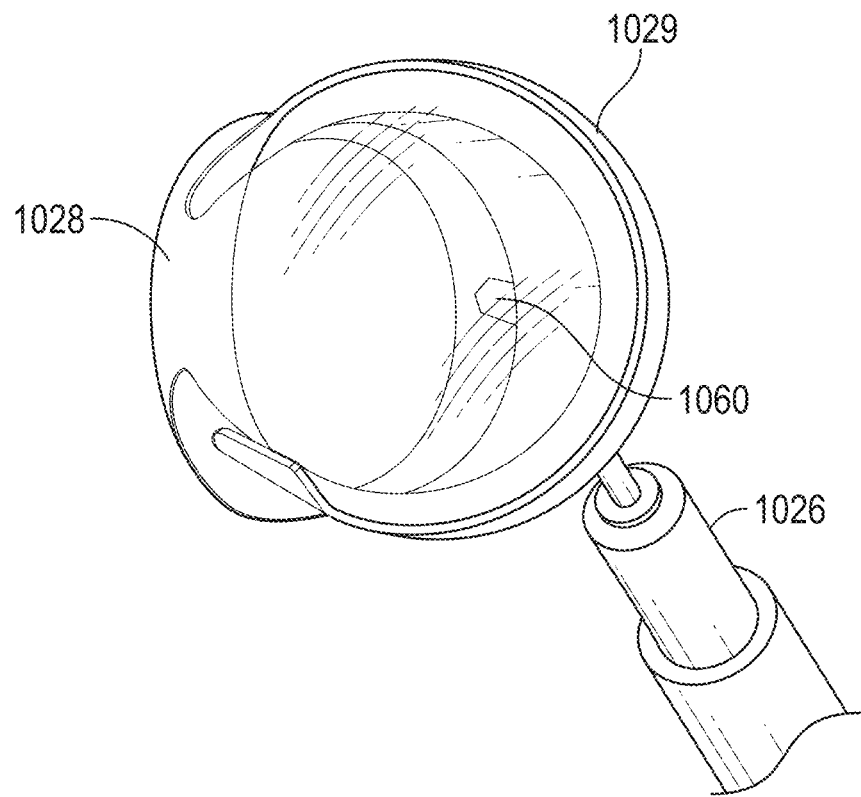
FIG. 10A is a picture showing an example location for a fixation point on a gonioscope from the patient's perspective.
Figure 10B:
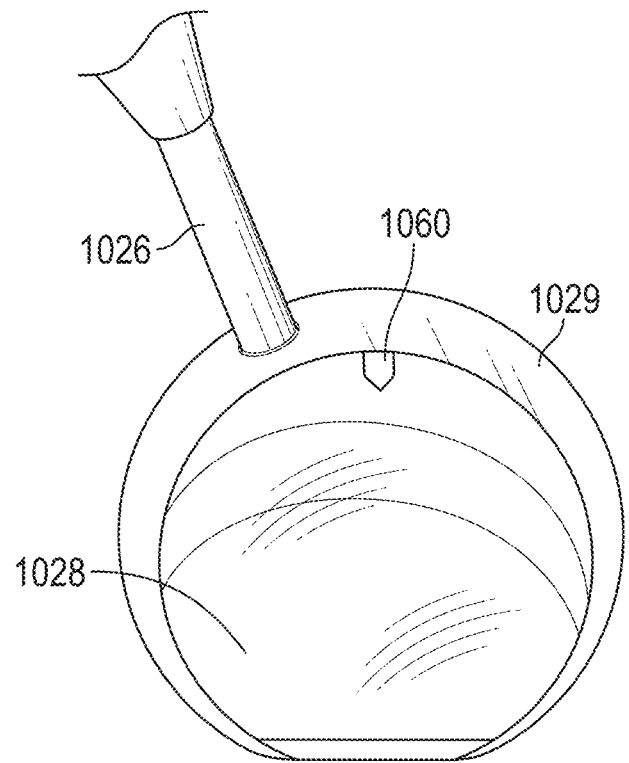
FIG. 10B is a picture showing an example location for a fixation point on a gonioscope from the user's perspective.
Figure 10C:
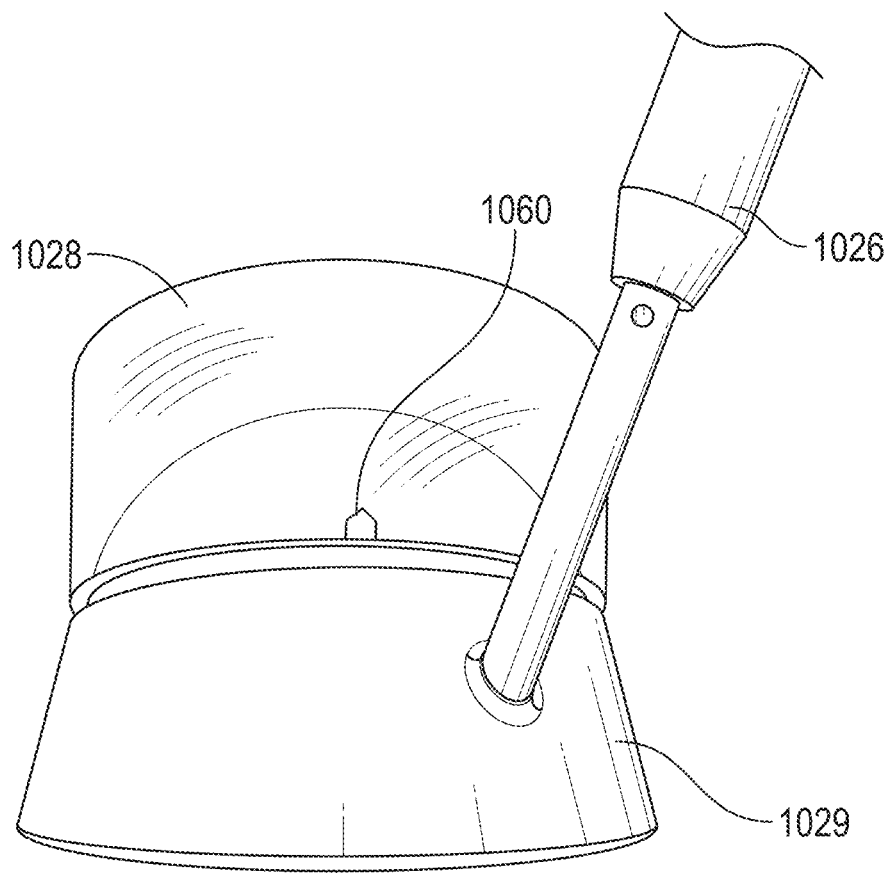
FIG. 10C is a picture showing a side view of an example location for a fixation point on a gonioscope.

FIGS. 10A to 10C show an example embodiment of a gonioscope having a gonioscopic fixation point from different perspectives. FIG. 10A provides a view from the patient's perspective. FIG. 10B provides a view from the perspective of a user (e.g., a medical practitioner). FIG. 10C provides a view from the side. A gonioscopic fixation point 1060 can be located on a gonioscopic optical element 1028 of a gonioscope. The location of a gonioscopic fixation point 1060 can be oriented on a surface of the gonioscopic optical element 1028 facing a handle 1026 of the gonioscope. A handle attachment element 1029 can couple the handle 1026 to the gonioscopic optical element 1028.

Figure 9A:
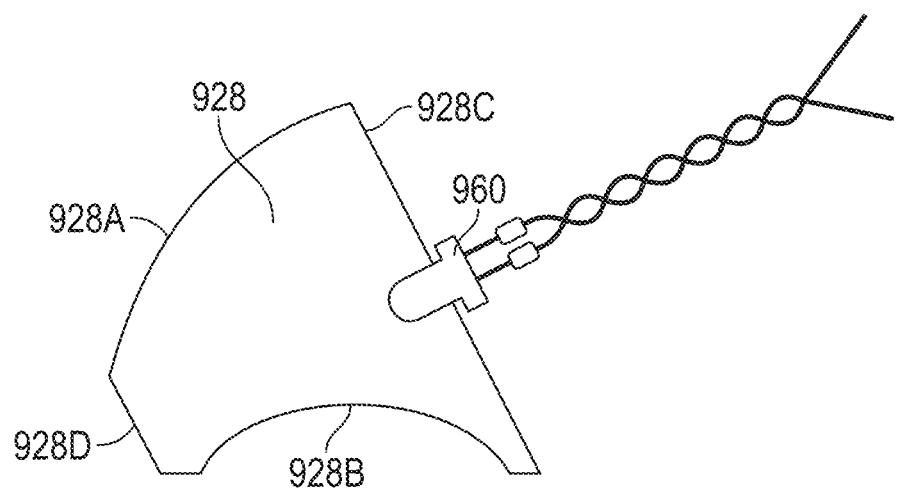
FIGS. 9A and 9B are schematic side views of different example embodiments of a gonioscopic optical element having at least one fixation point.

As shown in FIG. 9A, the gonioscopic fixation point 960 can include a light source. For example, the gonioscopic fixation point 960 can be a light emitting diode (LED), although other types of light sources can also be used. The gonioscope can include a power source, such as a battery, which can be contained in or on the handle of the gonioscope. The power source can provide electrical power to one or more light sources to provide one or more fixation elements. The gonioscopic fixation point 960 can be actively illuminated. In some embodiments, the gonioscopic optical element 928 can include a recess (e.g., on the thick side 928C, as shown in FIG. 9A), and the light source can be at least partially disposed in the recess.

Figure 9B:
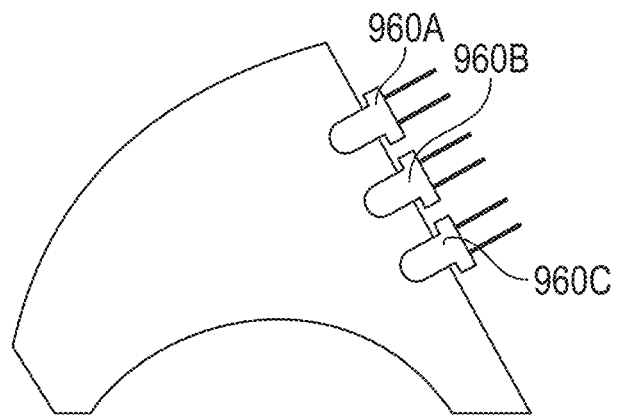
Figure 9C:
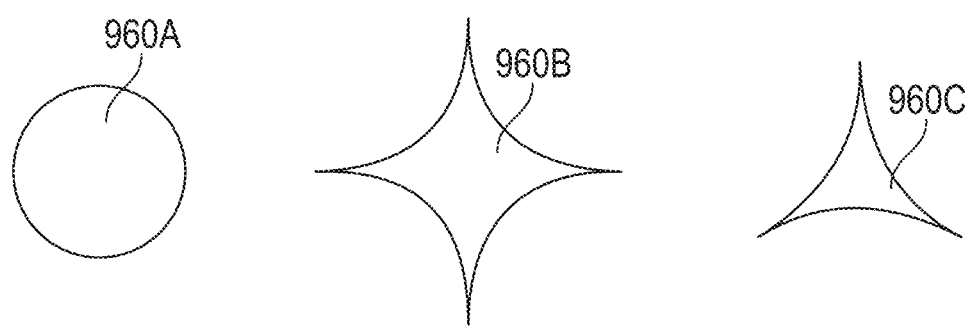
FIG. 9C is a schematic drawing of different example embodiments of multiple gonioscopic fixation points.

As shown in FIG. 9B, a gonioscopic fixation point can include multiple fixation points 960A, 960B, 960C. In one embodiment, the multiple fixation points can comprise a first fixation point 960A, a second fixation point 960B, and a third fixation point 960C. The multiple fixation points 960A-C can be light sources, similar to the description of the fixation point 960 in connection with FIG. 9A. The multiple fixation points 960A, 960B, 960C can be aligned along a linear path, although other special arrangements can be used depending on the desired orientation of the gonioscope relative to the eye. For example, when the eye is focused on a first fixation point 960A, the gonioscopic optical element 928 can be oriented relative to the eye to facilitate viewing a first structure or area in the eye, and when the eye is focused on the second fixation point 960B, the gonioscopic optical element 928 can be oriented relative to the eye to facilitate viewing a second structure or area in the eye. A third fixation point 960C can similarly be used to facilitate viewing a third structure or area in the eye, and additional fixation points can be used to facilitate viewing still additional structures or areas in the eye. The multiple fixation points 960A, 960B, 960C can comprise different appearances and different locations. For example, as shown in FIG. 9C, the first point 960A can comprise a circular shape, the second point 960B can comprise a star-shape, and the third point 960C can comprise a triangular shape, although various different shapes and other appearances can be used. In some embodiments, the different fixation points can have different colors. The multiple fixation points 960A, 960B, 960C can comprise one or more fixation points configured to be selectively illuminated. In some embodiments, the gonioscope can include one or more user input elements (e.g., one or more buttons or switches) configured to receive input from the user for controlling the selective illumination of the multiple fixation points 960A-C. For example, a user can illuminate a first fixation point 960A, while the one or more additional fixation point 960B and 960C are not illuminated. By this manner the user can direct the subject's vision to the illuminated fixation point 960A to facilitate proper orientation of the eye.

Figure 9D:
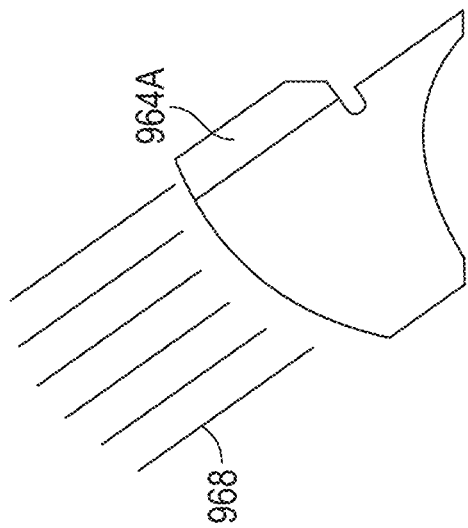
FIG. 9D is a schematic drawing of side views of different example embodiments of gonioscopic optical elements that include light pipes.
Figure 9D:
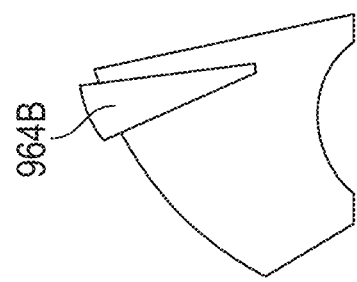
Figure 9D:
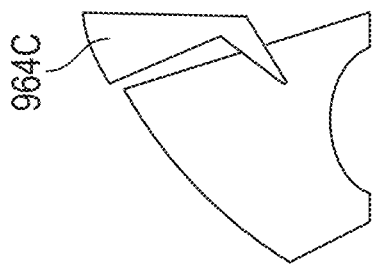
Figure 9E:
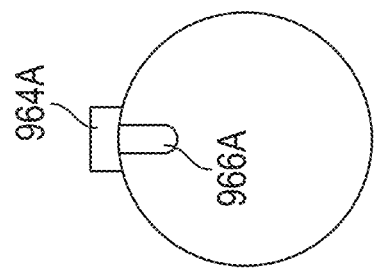
FIG. 9E is a schematic drawing of bottom views of different example embodiments of gonioscopic optical elements that include light pipes.
Figure 9E:
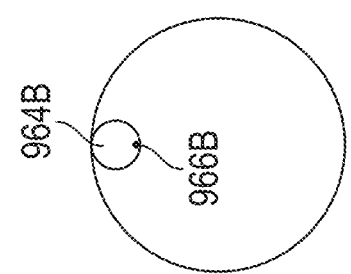
Figure 9E:
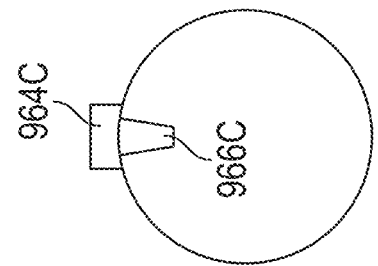

The gonioscopic fixation point can comprise a light pipe, in some embodiments. FIGS. 9D and 9E schematically show side and bottom views of different example embodiments of gonioscopic optical elements that include light pipes. The gonioscopic light pipes 964A. 964B. 964C can be configured to receive a light from the microscope 968. The gonioscopic light pipes 964A, 964B. 964C can be configured to redirect light from the microscope 968 to the patient's eye, to be visible to the patient as a fixation point. In some embodiments, the receiving end of the light pipe that receives light (e.g., light 968 from the microscope) can be larger than an exit end. The light pipe can be tapered from the receiving end to the exit end, for example to produce a small, bright fixation point 966A, 966B, and 966C for the patient to view.

In some embodiments, the light pipe 964B can be disposed at least partially inside the gonioscopic optical element. For example, the gonioscopic optical element can be overmolded around the light pipe 964B, or the light pipe can be inserted into a recess that is formed in the gonioscopic optical element. In some embodiments, the light receiving end of the light pipe can be exposed (e.g., on the proximal end of the gonioscopic optical element) to receive light into the light pipe 964B. A majority of the light pipe 964B can be disposed inside the gonioscopic optical element.

The light pipes 964A, 964B, 964C can be disposed partially or completely outside the gonioscopic optical element. The light receiving end of the light pipe 964B can be outside the gonioscopic optical element. The light pipe 964A can be outside the gonioscopic optical element and disposed directly adjacent and in contact with the gonioscopic optical element (e.g., on the thick side of the gonioscopic optical element). The light pipe 964C can be disposed outside and spaced apart from the gonioscopic optical element (e.g., on the thick side of the gonioscopic optical element). An air gap can be disposed between the gonioscopic optical element and the light pipe 964C, and the air gap can facilitate the propagation of light in the light pipe by total internal reflection. In some embodiments, a majority of the light pipe can be disposed outside the gonioscopic optical element, and in some cases a portion of the light pipe 964C (e.g., the light exit portion) can extend into the gonioscopic optical element (e.g., into a recess formed therein). In some embodiments, the light exit portion of the light pipe 964A can be disposed outside the gonioscopic optical element, and a feature (e.g., a recess) on the gonioscopic optical element can be configured to receive light emitted from the light exit portion to direct the light to the eye to provide the fixation point 966A. The light pipe 964A and 964B can be generally linear, or the light pipe 964 can include one or more turns to direct the light to form the fixation point 966A-C. In some embodiments, the material of the light pipe 964A-C can have a higher refractive index than the material of the gonioscopic optical element, to facilitate propagation of light in the light pipe by total internal reflection. The gonioscopic optical element can be configured to act as a cladding material on at least a portion of the outside of the light pipe 964A-C. In some embodiments, a reflective coating can be disposed on the outside of the light pipe 964A-C. The reflective coating can facilitate the propagation of light and/or can provide a separation from the main gonioscopic optical element 928.

Figure 9F:
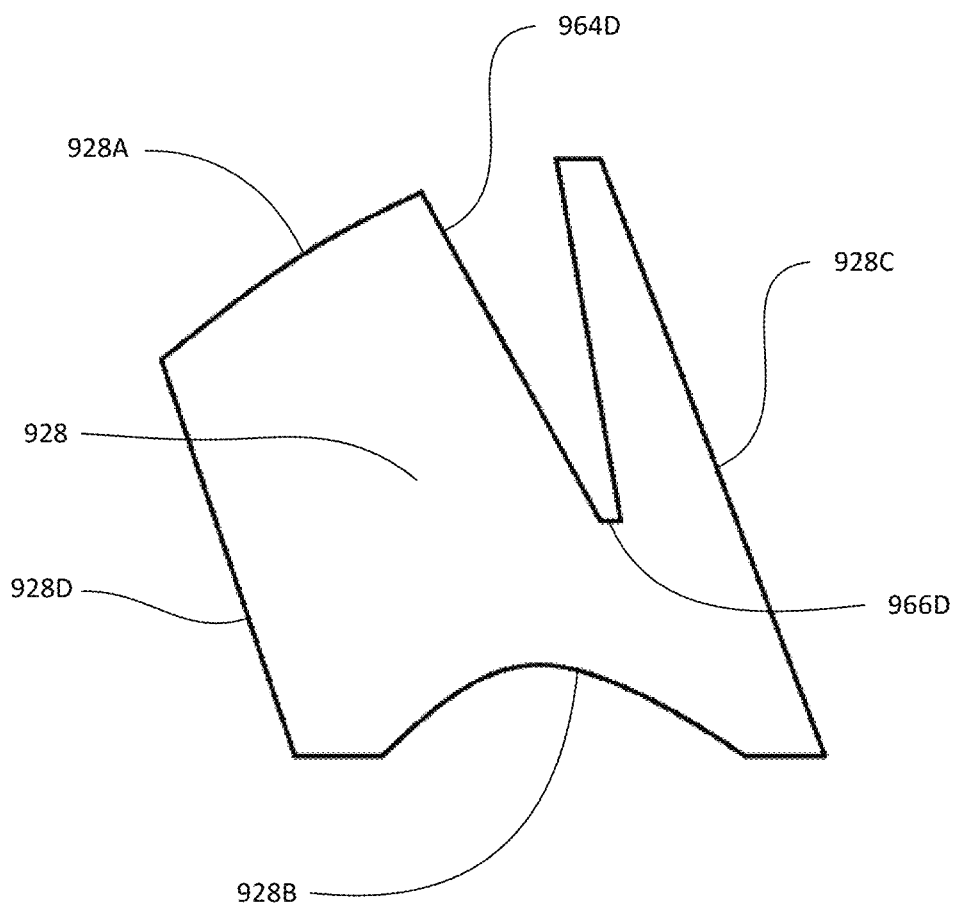
FIG. 9F is a schematic drawing of a side view of an example embodiment of a gonioscopic optical element.

With reference to FIG. 9F, in some embodiments, the gonioscopic optical element 928 can include a light guide 964D that is formed by one or more mirrored or reflective surfaces. The gonioscopic optical element 928 can include a recess (e.g., extending from the proximal surface 928A into the body of the gonioscopic optical element 928). One or more surfaces of the recess can be reflective to guide light along the recess (e.g., to create a fixation point 966D). In some embodiments, the sides of the recess can have a metallic coating or other reflective material thereon, and a bottom portion of the recess does not include the reflective material such that the light is reflected off the sides of the recess until the light reaches the bottom portion of the recess, where the light exits the recess and enters the material of the gonioscopic optical element 928 to be visible to a patient as an optical fixation point 966D. The light can propagate from the bottom portion of the recess, through the material of the gonioscopic optical element, to the distal surface 928B, in order to be visible to the eye of the patient. In some embodiments, the recess can be tapered having a larger width at the top and a narrower width at the bottom portion, such that the light guided down along the recess can be concentrated at the bottom portion of the recess. The recess can have a generally conical shape (e.g., a conical or frustoconical shape). The recess can have a generally circular, round, or oval cross-sectional shape, or a generally squared, rectangular, or polygonal cross-sectional shape.

Many variations are possible. For example, in some embodiments, the fixation point 960, 1060 can be a colored dot, an ink dot, a colored object, etc., which can be suspended inside the gonioscopic optical element or disposed on an outside surface of the gonioscopic optical element. The various embodiments disclosed regarding gonioscopes that include one or more fixation points can be used together with the embodiments disclosed herein with regards to the retention elements. For example, a gonioscope having one or more fixation points as shown or discussed in connection with any one of FIGS. 90A-10C can be used together with any one of the gonioscopic attachments or features shown or discussed in connection with FIGS. 1-8 and 11-13. In some implementations, the embodiments and features relating to the retention elements can be used without and independent of the embodiments and features disclosed herein relating to the fixation elements, and the embodiments and features relating to the fixation elements can be used without and independent of the embodiments and features relating to the retention elements.

Figure 14:
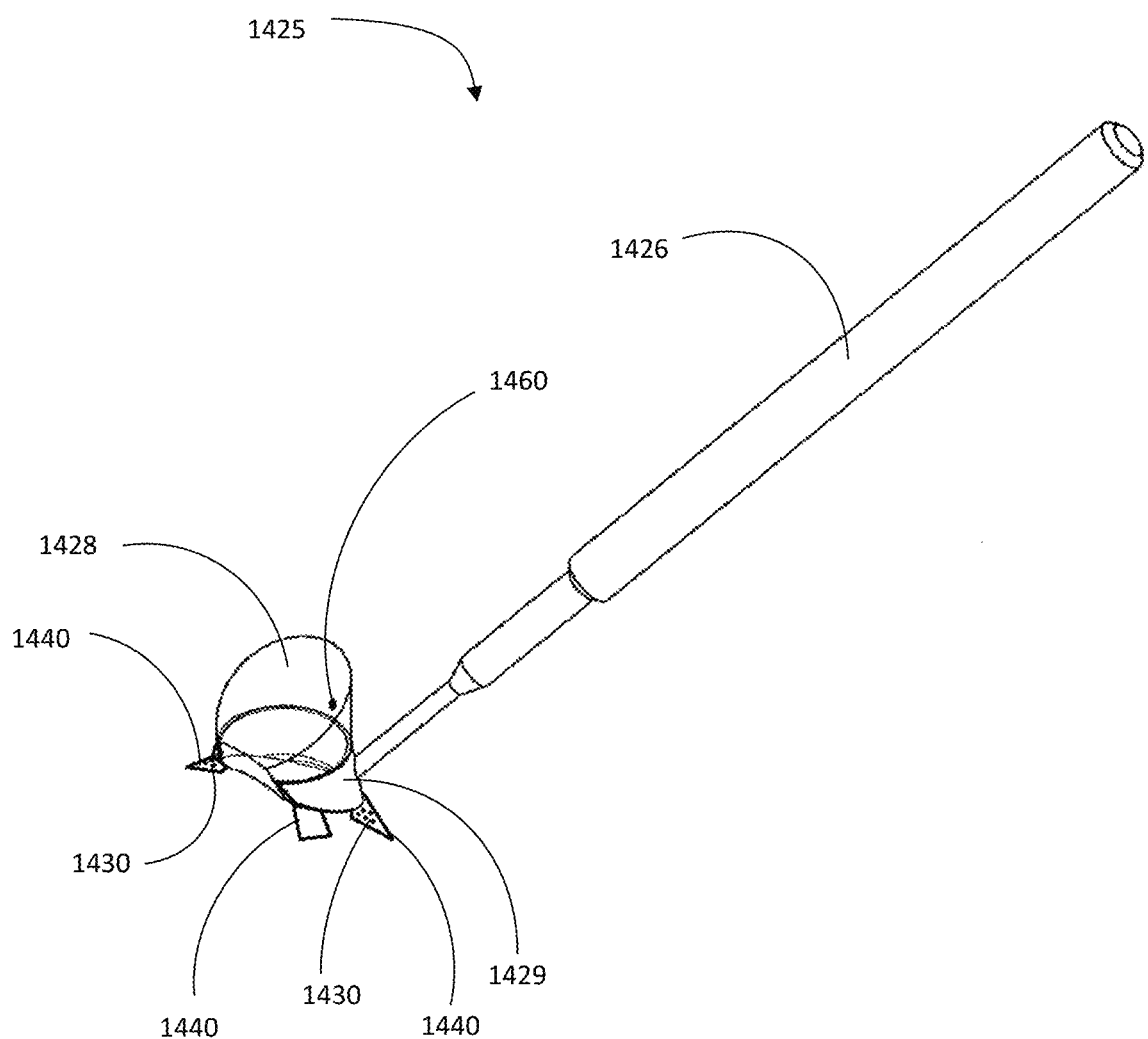
FIG. 14 shows an example embodiment of a gonioscope having retention elements.

FIG. 14 shows an example embodiment of a gonioscope 1425 having retention elements 1430 as an integral part of the gonioscope 1425, instead of on a gonioscopic attachment. The gonioscope 1425 can have features that are the same as, or similar to, the various gonioscopes descried herein. For example, a gonioscope can comprise a gonioscopic optical element 1428 having a concave distal surface and a proximal surface, a handle 1426 coupled to the gonioscopic optical element 1428, and a handle attachment element 1429, which can be similar to the other gonioscopes described herein.

The gonioscope 1425 can include a plurality of retention elements 1430 coupled to the gonioscopic optical element 1428 and configured to engage an eye to retain the gonioscope 1425 relative to the eye, similar to the other retention element embodiments disclosed herein. The plurality of retention elements 1430 can be stationary relative to the gonioscopic optical element 1428. Any of the various types of retention elements 1430 disclosed herein can be used for the gonioscope 1428. For example, the gonioscope 1428 can include one or more arms 1440 with one or more retention elements 1430 on distal portions of the arms 1440. In some embodiments, the arms 1440 can extend from the handle attachment element 1429, similar to the arms of other embodiments extending from the body of the gonioscopic attachment. The arms 1440 can extend distally. The arms can extend radially outward and can be configured to engage the sclera of the eye and can be configured to not contact the cornea. The retention elements 1430 can be configured to restrain movement of the eye relative to the gonioscope 1425. The retention elements 1430 can be configured to orient the gonioscopic optical element 1428 relative to the eye to facilitate viewing into the eye. For example, the retention elements 1430 (e.g., on the one or more arms 1440) can be configured to lift a portion or all of the distal surface of the gonioscopic optical element off of the eye (e.g., the cornea), and can offset the distal surface of the gonioscopic optical element 1428 relative to the curvature of the eye (e.g., of the cornea), for example, as discussed in connection with FIG. 12. Many other configurations are possible.

The gonioscope 1425 can further comprise one or more fixation points 1460 configured to be visible to the subject when the gonioscope 1425 is positioned on the eye. Any of the features relating to the fixation points described and shown in connection with FIGS. 9A-10C can be used for the gonioscope 1425. For example, the at least one fixation point 1460 can include one or more light sources, one or more light pipes, etc.

In some embodiments, a gonioscope or a gonioscopic attachment (such as the various embodiments disclosed herein) can be coupled to a lid speculum that is used to hold the eye open, in order to facilitate holding the gonioscope and/or gonioscopic attachment in place on the eye. In some embodiments, a handle can be removably attachable to the gonioscope and/or the gonioscopic attachment to enable a medical practitioner to adjust the position of the gonioscope and/or gonioscopic attachment on the eye and to remove the handle when a desired position is achieved. The handle can also be used to temporarily apply a downward force to restrain the eye while surgical tools are used. These features can be applied to various embodiments of the gonioscopes and gonioscopic attachments disclosed herein.

Figure 15:
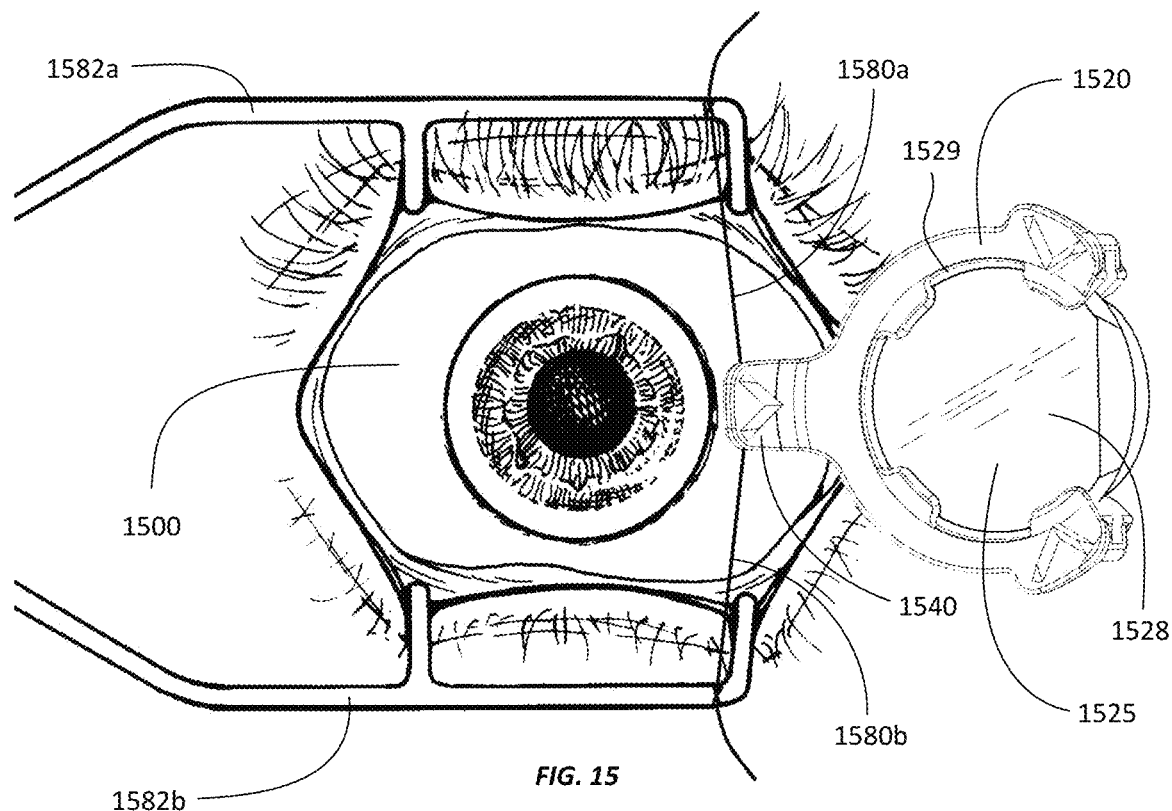
FIG. 15 shows and example embodiment of a gonioscopic attachment coupled to a lid speculum in a disengaged position.
Figure 16:
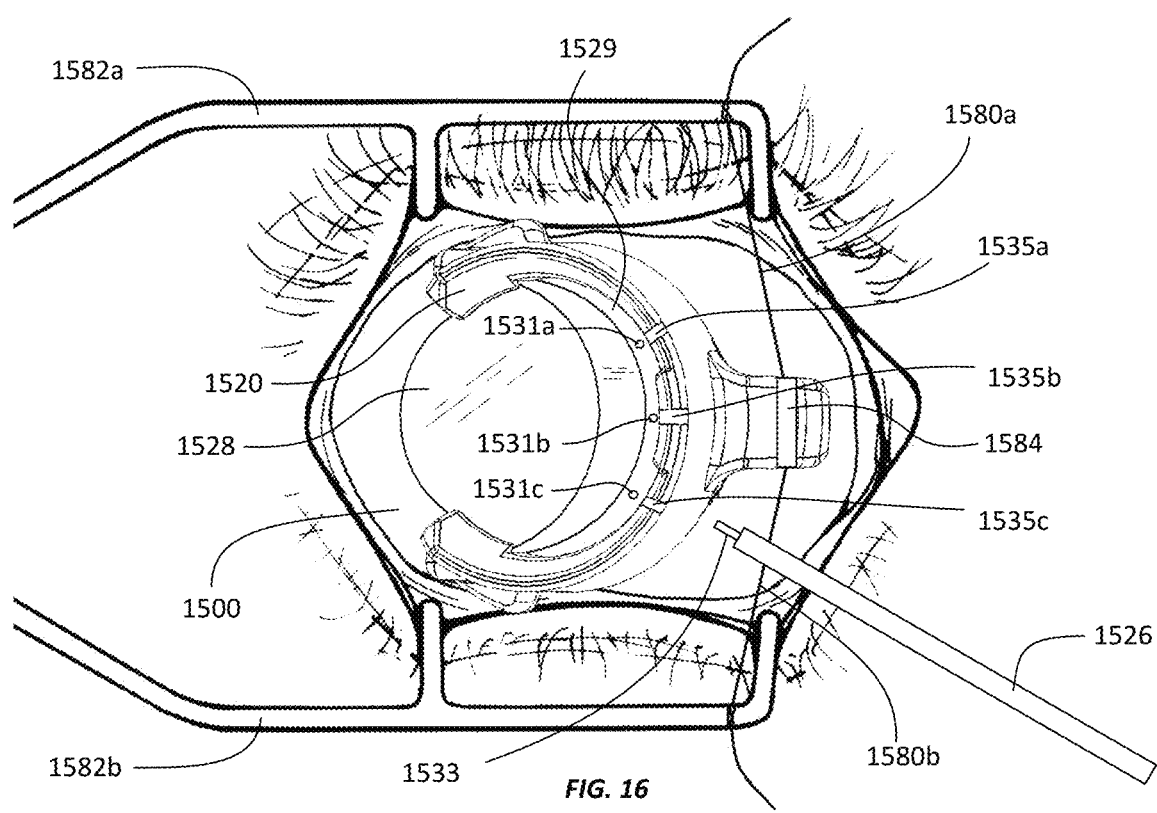
FIG. 16 shows and example embodiment of a gonioscopic attachment coupled to a lid speculum in an engaged position.

With reference to FIGS. 15 and 16, a gonioscopic attachment 1520 and gonioscope 1525 can be used to view structure inside of an eye 1500, as discussed herein. The gonioscopic attachment 1520 and the gonioscope 1525 can include features that are the same as or similar to the various other embodiments of gonioscopic attachments and gonioscopes discussed herein, and the disclosure recited herein for the other embodiments herein can be applied to the embodiment of FIGS. 15 and 16, and vice versa. The gonioscopic attachment 1520 can receive the gonioscope 1525 as discussed herein. The gonioscopic attachment 1520 can include a coupling mechanism, such as one or more tethers 1580*a-b*, which can be configured to couple the gonioscopic attachment 1520 to the lid speculum. The lid speculum can include an upper portion 1582*a* that is configured to hold open the upper eyelid and a lower portion 1582*b* that is configured to hold open the lower eyelid. In some implementations, the gonioscopic attachment 1520 can include a first tether 1580*a* that is configured to couple the gonioscopic attachment 1520 to the upper portion 1582*a* of the lid speculum and a second tether 1580*b* that is configured to couple the gonioscopic attachment 1520 to the lower portion 1582*b* of the lid speculum. The one or more tethers 1580*a-b* can be elongate flexible tethers, such as a string, lace, band, or the like. In some embodiments, the one or more tethers 1580*a-b* can be made of a resilient material (such as silicone or another elastomer), which can enable the tethers 1580*a-b* to stretch somewhat for positioning of the gonioscopic attachment 1520, or a non-resilient material.

The one or more tethers 1580*a-b* can be attached to an arm 1540 of the gonioscopic attachment 1520. In some embodiments, the gonioscopic attachment 1520 can include multiple arms, and the one or more tethers 1580*a-b* can be attached to the arm 1540 identified in FIGS. 15 and 16, which can be, for example, positioned opposite of the opening in the C-shaped body of the gonioscopic attachment 1520, as discussed herein. The one or more tethers 1580*a-b* can be attached to the gonioscopic attachment at various other locations as well, such as the C-shaped body or the other arms of the gonioscopic attachment 1520.

The one or more tethers 1580*a-b* can be attached to the gonioscopic attachment 1520 by overmolding. For example, material (e.g., silicone or other material suitable for molding processes) can be overmolded onto a portion of the gonioscopic attachment 1520 (e.g., onto the arm 1540) to form one or more overmolded attachment areas 1584. The one or more tethers 1580*a-b* can extend from the one or more overmolded attachment areas 1584. The one or more tethers 1580*a-b* can be integral with, can be made of the same material as, and/or can be molded together with, the one or more overmolded attachment areas 1584. The one or more tethers 1580*a-b* can be attached to the gonioscopic attachment 1520 in various other ways, such as by an adhesive, a clamp, a pinch or friction fitting, a knot tying the one or more tethers 1580*a-b* to the gonioscopic attachment 1520, one or more wraps in the one or more tethers 1580*a-b* around a corresponding feature or portion of the gonioscopic attachment 1520, or any other suitable attachment mechanism or manner.

The one or more tethers 1580*a-b* can attach to the lid speculum in various ways, such as by an adhesive, a clamp, a pinch or friction fitting, a knot tying the one or more tethers 1580*a-b* to the lid speculum, one or more wraps in the one or more tethers 1580*a-b* around a corresponding feature or portion of the lid speculum, or any other suitable attachment mechanism or manner. In some embodiments, the one or more tethers 1580*a-b* can be attached to the lid speculum by overmolding, similar to the discussion above. In some embodiments, the one or more tethers 1580*a-b* can be attached to the lid speculum by one or more overmolded attachment areas (not shown in FIGS. 15-16) and to the gonioscopic attachment 1520 by the one or more overmolded attachment areas 1584. In some implementations, the lid speculum, the coupling mechanism (e.g., the one or more tethers 1580a-b), and the gonioscopic attachment 1520 can be a single instrument. The coupling mechanism (e.g., the one or more tethers 1580a-b) can irremovably attach to one or both the lid speculum and the gonioscopic attachment 1520. The coupling mechanism (e.g., the one or more tethers 1580a-b) can removably attach to one or both the lid speculum and the gonioscopic attachment 1520.

The coupling mechanism (e.g., the one or more tethers 1580a-b) can be configured to enable the gonioscopic attachment 1520 and/or gonioscope 1525 to move between an engaged position and a disengaged position. In the engaged position, the gonioscope 1525 is positioned to enable the medical practitioner to view structure inside the eye 1500, as described herein. In the disengaged position, the gonioscope 1525 can be separated from the eye 1500 such that it does not enable viewing of structure inside the eye 1500. The coupling mechanism can be configured to enable the gonioscopic attachment 1520 and/or gonioscope 1525 to pivot between the disengaged position (e.g., as shown in FIG. 15) to the engaged position (e.g., as shown in FIG. 16). The one or more tethers 1580a-b can define a pivot axis about which the gonioscopic attachment 1520 can pivot. In the disengaged position (e.g., FIG. 15), the gonioscopic attachment 1520 and/or the gonioscope 1525 can be disposed to the side of the eye, away from the optical axis (e.g., to the nasal side of the eye), and the cornea of the eye can be uncovered. In the disengaged position (e.g., FIG. 15), the gonioscopic attachment 1520 and/or gonioscope 1525 can be positioned generally upside-down (e.g., having a contact surface or distal surface of the gonioscopic optical element 1528 facing upward, away from the eye 1500). The gonioscopic attachment 1520 and/or gonioscope 1525 can be pivoted from the disengaged position (e.g., FIG. 15) to the engaged position (e.g., FIG. 16), such as like a flap. In the engaged position, the contact surface or distal surface of the gonioscopic optical element 1528 can contact the eye 1500, or be positioned sufficiently close to the eye 1500 (e.g., having an index matching gel disposed between the contact surface or distal surface and the eye 1500) such that a medical practitioner can view structure within the eye 1500 using the gonioscopic optical element 1528.

In some embodiments, the first tether 1580a can extend in a first direction to attach to the lid speculum, and the second tether 1580b can extend in a second direction that is generally opposite of the first direction to attach to the lid speculum. The direction of the first tether 1580a can be within about 30 degrees, within about 20 degrees, within about 10 degrees, within about 5 degrees or less of the opposite of the direction of the second tether 1580b. Various other configurations are possible. The gonioscopic attachment 1520 and/or the gonioscope 1525 can be coupled to the lid speculum by a single tether, by three tethers, by four tethers, or more. Other coupling mechanisms can be used to couple the gonioscopic attachment 1520 and/or the gonioscope 1525 to the lid speculum. For example, the gonioscopic attachment 1520 can include a feature (e.g., a recess, groove, rod, snap, etc.) that is configured to engage a corresponding feature (e.g., a recess, groove, rod, snap, etc.) on the lid speculum to couple them together, for example, in a manner that enables moving (e.g., pivoting) the gonioscope 1525 between the disengaged and engaged positions. In some embodiments, the lid speculum can be configured to receive or otherwise couple to the gonioscopic attachment 1520 and/or the gonioscope 1525. In some embodiment, a conventional lid speculum can be used.

In some embodiments, a removable handle 1526 can be used to facilitate positioning of the gonioscope 1525 and/or the gonioscopic attachment 1520 on the eye. For example, the gonioscope 1525 can include a gonioscopic optical element 1528 and a handle attachment element 1529 (which can clamp onto the gonioscopic optical element 1528, as discussed herein). The handle attachment element 1529 can include one or more handle attachment features 1531a-c for receiving a corresponding attachment feature 1533 on the handle 1526. For example, the gonioscope 1525 can include a handle attachment feature 1531a for attaching the handle 1526 in a right-handed configuration, a handle attachment feature 1531b for attaching the handle 1526 in a center configuration, and a handle attachment feature 1531c for attaching the handle 1526 in a left-handed configuration. The handle attachment features 1531a-c on the gonioscope 1525 can be recesses, and the attachment feature 1533 on the handle 1526 can be a protrusion that is configured to selectively engage the recesses. In some embodiments, the gonioscopic attachment 1520 can include one or more handle support features 1535a-c, which can be configured to engage the handle 1526 when the handle 1526 is attached (e.g., to a corresponding one of the handle attachment features 1531a-c) to provide support to the handle 1526. The handle support features 1535a-c can be grooves that are sized and shaped to receive a portion of the handle 1526 therein. By way of example, the attachment feature 1533 (e.g., protrusion) on the handle 1526 can engage (e.g., insert into) one of the handle attachment features 1531a-c (e.g., recesses), and that engagement can provide a first point of contact with the handle 1526. In some implementations, the handle 1526 can pivot about the first point of contact across a range of motion. The handle 1526 can be laid into a corresponding handle support feature 1535a-c to provide a second point of contact to the handle 1526. The two points of contact between the gonioscope 1525 or gonioscopic attachment 1520 and the handle 1526 can provide sufficient stability to enable a medical practitioner to move the gonioscope 1525 and/or gonioscopic attachment 1520 on the eye by applying force via the handle 1526. When the gonioscope 1525 and/or gonioscopic attachment 1525 is located at the desired position, the handle 1526 can be removed by merely lifting the handle 1526 away from the gonioscope 1525 and/or the gonioscopic attachment 1520. The handle 1526 can attach to the gonioscopic attachment 1520 and/or gonioscope 1525 by a loose engagement that can be easily disengaged for removal of the handle 1526 without moving the position of the gonioscope 1525 and/or gonioscopic attachment 1520 on the eye. The handle 1526 can easily be reattached and removed as needed during a surgical procedure to adjust the position of the gonioscope 1525 and/or the gonioscopic attachment 1520 on the eye.

Other configurations are possible. For example, the gonioscope 1525 can include only one or two of the handle attachment features 1531a-c (and the associated handle support features 1535a-c), and one or more of the handle attachment features 1531a-c (and the associated handle support features 1535a-c) shown in FIG. 16 can be omitted. In some implementations, additional handle attachment features 1531a-c and/or handle support features 1535a-c can be used to provide additional handle attachment orientations (e.g., in addition to the right-handed, left-handed, and center orientations discussed herein). In some embodiments, multiple handle support features 1535a-c can be used with a single one of the handle attachment features 1531a-c. for example, a single handle attachment features 1531b can receive the handle 1526 with enough freedom of movement so that the handle 1526 can selectively engage a first handle support feature 1535a for a right-handed configuration, a second handle support feature 1535b for a centered configuration, and a third handle support feature 1535c for a left-handed configuration. In some embodiments, the attachment feature 1533 on the handle 1526 can be a recess or a groove, and the one or more handle attachment features 1531a-c on the gonioscope 1525 can be protrusions configured to removably engage the recess or groove. Other suitable attachment features can also be used.

In some embodiments, the handle 1526 can be infinitely positionable within a range of positions. For example, the handle 1526 can engage the gonioscope 1525 and/or gonioscopic attachment 1520 using a friction fitting, such that when pressure is applied the handle 1526 is held in place relative to the gonioscope 1525 and/or gonioscopic attachment 1520, and when pressure is released the handle 1526 can be moved relative to the gonioscope 1525 and/or gonioscopic attachment across the range of positions.

In some embodiments, the engagement between the handle 1526 and the gonioscope 1525 and/or gonioscopic attachment 1520 can include a hexagonal engagement such that the handle can be selectively positioned at six different orientations. The engagement between the handle 1526 and the gonioscope 1525 and/or gonioscopic attachment 1520 can use a polygonal engagement having various different numbers of sides (e.g., 3, 4, 5, 6, 8, 10, 12, etc. sides) to provide various different numbers of available handle positions. In some embodiments, a lock mechanism can lock the handle 1526 to the gonioscope 1525 and/or gonioscopic attachment 1520 such that the lock mechanism has to be released in order to remove the handle 1526, as opposed to merely releasing the handle 1526 by lifting it away from the gonioscope 1525 and/or gonioscopic attachment 1520 as in some other embodiments. The lock mechanism can be a snap fitting between the attachment feature 1533 on the handle 1526 and the one or more handle attachment features 1531a-c. In some embodiments the lock mechanism can include a release element that can be actuated by the user to disengage the lock mechanism to allow the handle 1526 to be released. Various other suitable lock mechanisms can be used.

Figure 17:
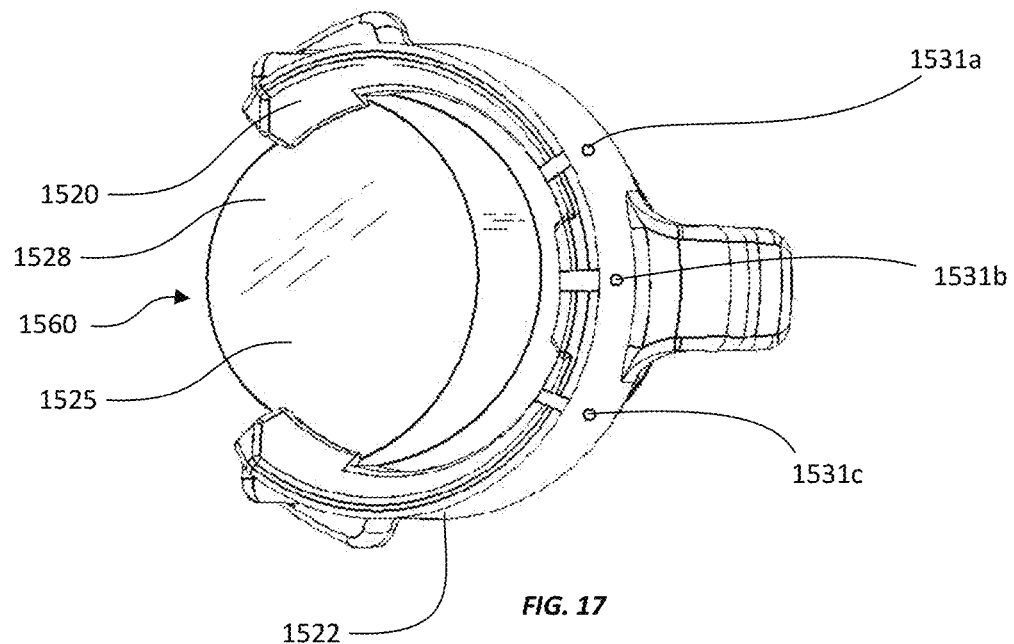
FIG. 17 shows an example embodiment of a gonioscope and a gonioscopic attachment that includes one or more handle attachment features.
Figure 18:
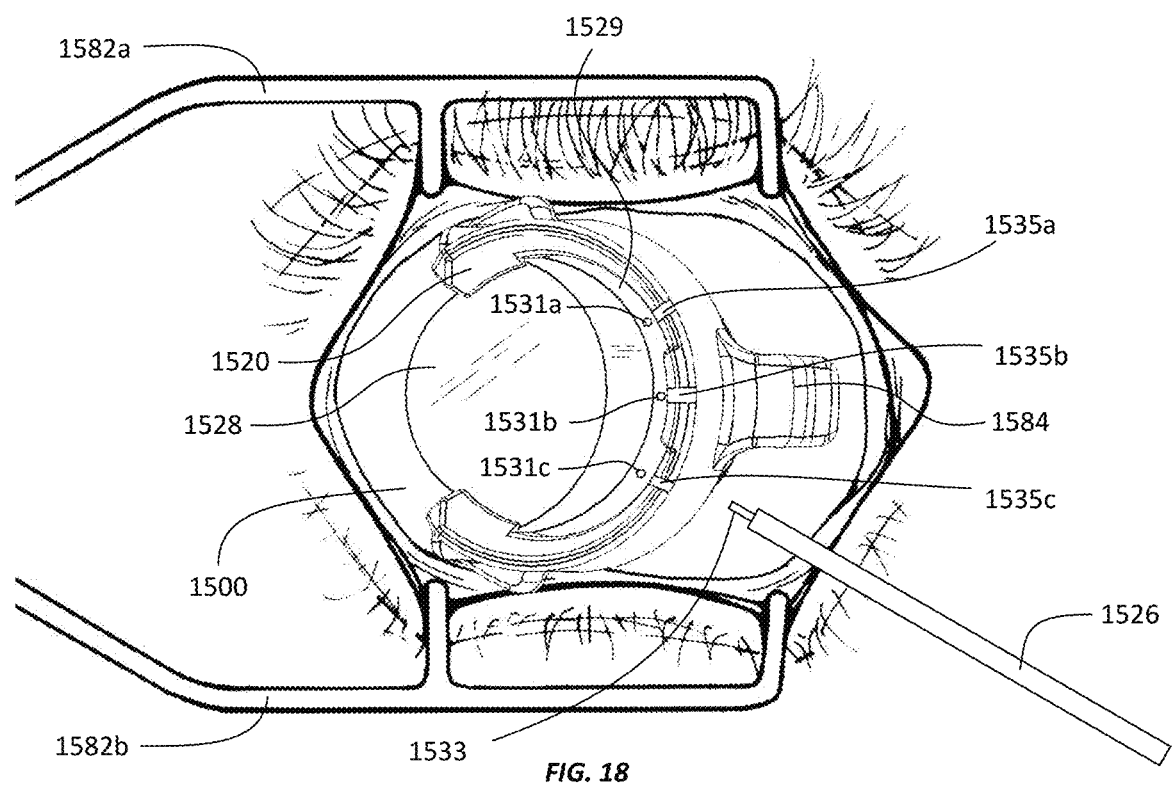
FIG. 18 shows an example embodiment of a gonioscope and gonioscopic attachment with a removable handle.

In some embodiments, the handle 1526 can removably attach to the gonioscopic attachment 1520. For example, the one or more handle attachment features 1531a-c can be located on the gonioscopic attachment 1520, for example on an outside surface of the C-shaped body 1522 of the gonioscopic attachment 1520, such as generally opposite of the open side 1560 of the C-shaped body. The disclosure herein relating to the handle attachment features 1531a-c can apply to features on the gonioscope 1520 (for example as shown in FIG. 16) or on the gonioscopic attachment 1525 (for example, as shown in FIG. 17). In some embodiments, the handle 1526 can removably attach to the gonioscopic optical element 1528, and in some implementations the handle attachment element 1529 can be omitted from the gonioscope 1525. For example, the one or more handle attachment features 1531a-c can be recesses, or other features, formed on the gonioscopic optical element 1528. In some embodiments, the handle 1525 is not removable, such as similar to the gonioscopes of FIGS. 13 and 14. With reference to FIG. 18, in some embodiments, the handle 1526 can be removably attachable to the gonioscope 1525 and/or gonioscopic attachment 1520, as discussed herein, without being coupled to the lid speculum by the one or more tethers 1580a-b or other coupling mechanism.

In some embodiments, the handle 1526 can be omitted entirely. For example, the coupling mechanism, such as the tethers 1580a-b, can hold the gonioscope 1525 and/or gonioscopic attachment 1520 in place on the eye 1500 without the handle. In some embodiments, the coupling mechanism, such as the tethers 1580a-b, can be configured to apply a force that pulls the gonioscope 1525 and/or gonioscopic attachment 1520 against the eye 1500 when in use. For example, the one or more tethers 1580a-b can attach to the gonioscopic attachment 1520 and/or gonioscope 1520 at one or more locations that are higher (or axially further away from the back of the eye along the eye's optical axis) than the one or more locations where the one or more tethers 1580a-b attach to the lid speculum. Accordingly, the tethers 1580a-b can pull the gonioscopic attachment 1520 and/or the gonioscope 1525 down against the surface of the eye, without any pressure applied from a handle 1526. The tethers 1580a-b can pull the gonioscopic attachment 1520 and/or the gonioscope 1525 down against the surface of the eye to restrain the eye during surgery, without any pressure applied from a handle 1526.

Figure 19:
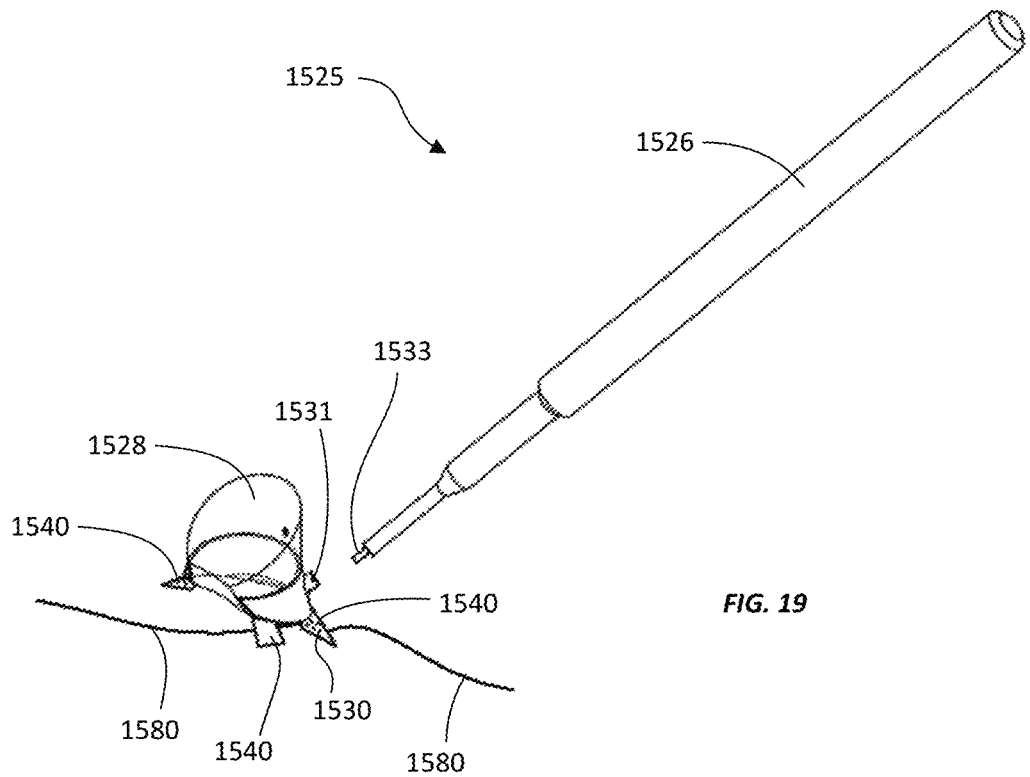
FIG. 19 shows an example embodiment of a gonioscope having a removable handle and one or more tethers for coupling the gonioscope to a lid speculum.
Figure 20:
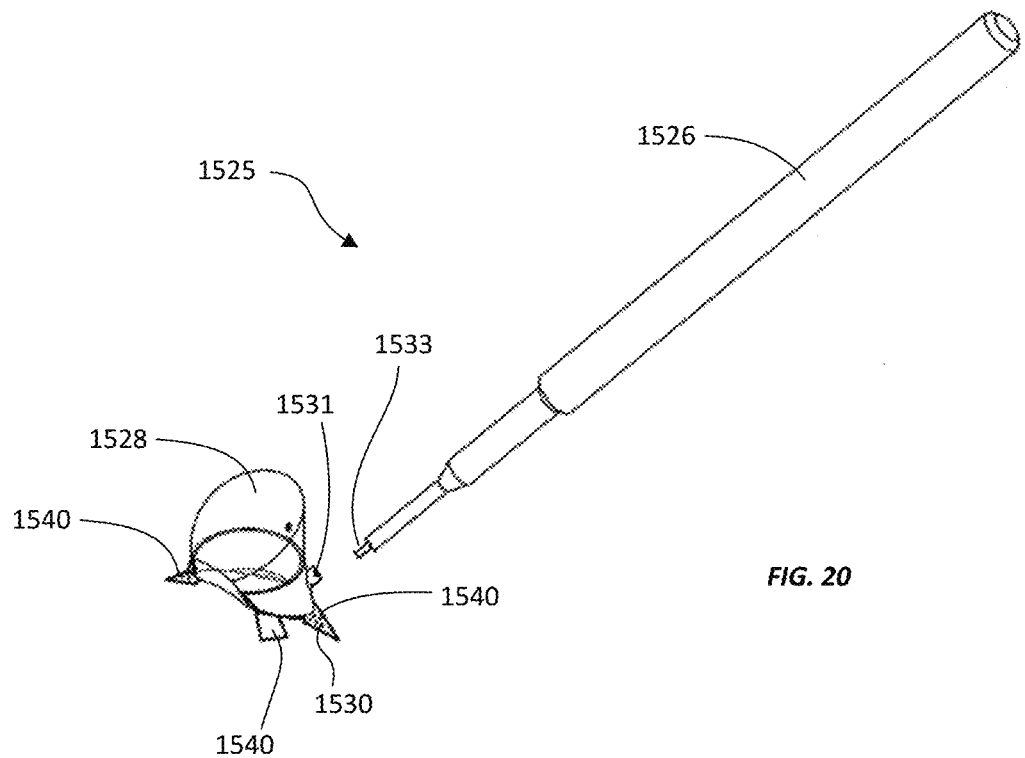
FIG. 20 shows an example embodiment of a gonioscope having a removable handle.

In some embodiments, the features of the gonioscopic attachment 1520 can be incorporated into the gonioscope 1525 itself. With reference to FIGS. 19 and 20, the gonioscope 1525 can have features that are the same as, or similar to, the various gonioscopes descried herein. For example, a gonioscope can comprise a gonioscopic optical element 1528 having a concave distal surface and a proximal surface, a removably handle 1526, and a handle attachment element 1529, which can be similar to the other gonioscopes described herein. For example, the handle 1526 can include an attachment features 1533 that is configured to engage one or more handle attachment features 1531, which can be on the handle attachment element 1529 in some embodiments, to couple the removable handle 1526 to the gonioscopic optical element 1528. The various types of attachment features described herein can be used to removably couple the handle 1525 to the gonioscopic optical element 1528. In some embodiments, the handle 1526 of FIGS. 19 and 20 is not removably, for example, similar to the handle of FIGS. 13 and 14.

The gonioscope 1525 can include a plurality of retention elements 1530 coupled to the gonioscopic optical element 1528 and configured to engage an eye to retain the gonioscope 1525 relative to the eye, similar to the other retention element embodiments disclosed herein. The plurality of retention elements 1530 can be stationary relative to the gonioscopic optical element 1528. Any of the various types of retention elements 1530 disclosed herein can be used for the gonioscope 1525. For example, the gonioscope 1528 can include one or more arms 1540 with one or more retention elements 1530 on distal portions of the arms 1540. In some embodiments, the arms 1540 can extend from the handle attachment element 1529, similar to the arms of other embodiments extending from the body of the gonioscopic attachment. The arms 1540 can extend distally. The arms can extend radially outward and the retention elements 1530 can be configured to engage the sclera of the eye and can be configured to not contact the cornea. The retention elements 1530 can be configured to restrain movement of the eye relative to the gonioscope 1525. The retention elements 1530 can be configured to orient the gonioscopic optical element 1528 relative to the eye to facilitate viewing into the eye. For example, the retention elements 1530 (e.g., on the one or more arms 1540) can be configured to lift a portion or all of the distal surface of the gonioscopic optical element off of the eye (e.g., the cornea), and can offset the distal surface of the gonioscopic optical element 1528 relative to the curvature of the eye (e.g., of the cornea), for example, as discussed in connection with FIG. 12.

As can be seen, for example, in FIG. 19, the gonioscope 1525 can include a coupling mechanism, such as one or more tethers 1580, which can be configured to couple the gonioscope 1525 to a lid speculum. The disclosure herein relating to the coupling mechanism (e.g., in connection with FIGS. 15-18) can apply to the embodiment of FIG. 19. For example, the tethers 1580 can enable the gonioscope 1525 to be moved (e.g., pivot) between a disengaged position (e.g., in which the gonioscope 1525 is positioned generally upside-down) to an engaged position for viewing structure in the eye, as discussed herein. The one or more tethers 1580 can be configured to pull the gonioscope 1525 against the eye such that the force facilitates retention of the gonioscope 1525 at a desired position relative the eye, as discussed herein. In some embodiments, the handle 1526 of FIG. 19 can be omitted. The coupling mechanism, such as the one or more tethers 1580, can be configured to position and retain the gonioscope 1525 on the eye without the handle 1525. With reference to FIG. 20, in some embodiments, the coupling mechanism, such as the one or more tethers 1580, can be omitted. In some embodiments, the gonioscope 1525 is not configured to couple to the lid speculum. Various other features disclosed herein can be used with the embodiments of FIGS. 19 and 20. For example, the gonioscope 1525 can further comprise one or more fixation points, as discussed herein.

In some instances it can be advantageous to direct light into the eye of the patient. For example, light can be directed into the eye to facilitate producing an image of the inside of the eye (e.g., of the anterior chamber). In some implementations, transillumination and/or retroillumination can be used to view structure inside the eye. By way of example, light can be directed through the tissue of the eye to facilitate assessment of a stent implanted in the eye that is designed to facilitate flow of aqueous humor from the anterior chamber through the stent into Schlemm's canal. If a stent was inserted too far into the tissue of the eye, the eye tissue can block or impede flow into the inlet of the stent. Using transillumination and/or retroillumination, a medical practitioner can view the position of the stent (e.g., the light can produce a silhouette of the stent) to assess the implantation.

Figure 21:
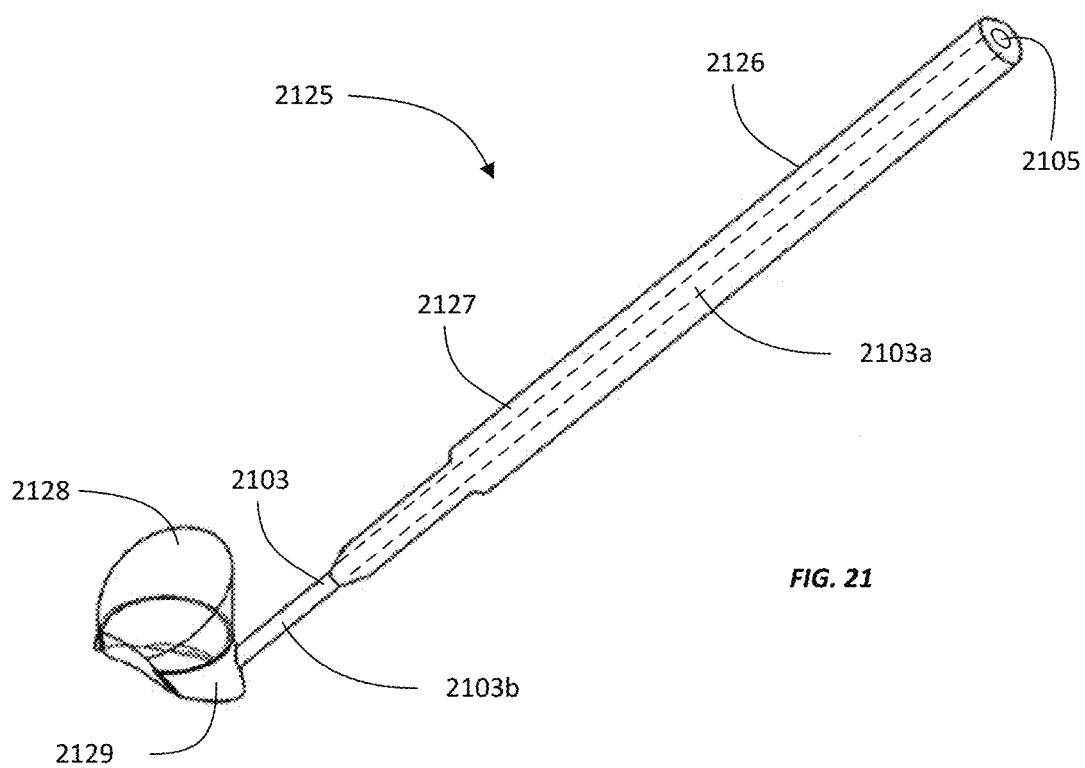
FIG. 21 shows an example embodiment of a gonioscope that is configured to direct light into an eye.

In some implementations, light can be directed into the eye through a gonioscope. FIG. 21 shows an example embodiment of a gonioscope 2125 that is configured to direct light into an eye of a subject. The gonioscope 2125 can include a gonioscopic optical element 2128, a handle 2126, and a handle attachment element 2129, which can be similar to the other gonioscope embodiments disclosed herein. The gonioscope 2125 can include a light pipe 2103 for directing light from outside the gonioscope, through the gonioscope, and into the eye. The light pipe 2103 can extend through the handle 2126. The handle 2126 can include a light inlet 2105 that is configured to receive light (e.g., from outside the gonioscope 2125) so that the received light can propagate along the light pipe 2103 toward the patient's eye. The light inlet 2105 can be positioned at an end of the handle 2126 opposite the gonioscopic optical element 2128. The light inlet 2105 can be on a proximal end of the handle 2126 and the gonioscopic optical element 2128 can be positioned at the distal end of the handle 2126.

The handle 2126 can include an outer handle portion 2127, which can surround at least a portion of the light pipe 2103. The outer handle portion 2127 can surround a full circumference of the light pipe 2103. The outer handle portion 2127 can be concentric with the light pipe 2103. Either or both of the light pipe 2103 and the handle 2126 can be generally cylindrical in shape, although other shapes can also be used. The light pipe 2103 can be disposed inside the outer handle portion 2127.

Figures 22, 23, 24:
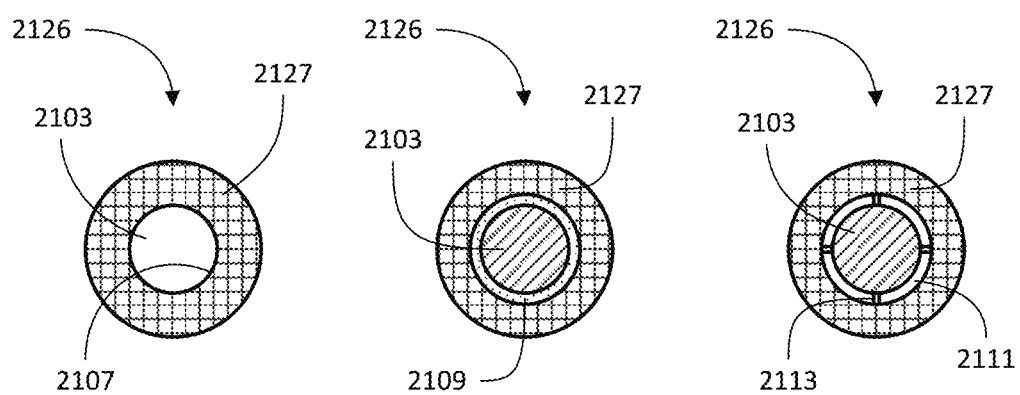
FIG. 22 is a cross-sectional view of an example embodiment of a gonioscope handle having a light pipe.
FIG. 23 is a cross-sectional view of another example embodiment of a gonioscope handle having a light pipe.
FIG. 24 is a cross-sectional view of another example embodiment of a gonioscope handle having a light pipe.

FIGS. 22, 23, and 24 show cross-sectional views of example embodiments of handles 2126 for the gonioscope 2125. With reference to FIG. 22, in some embodiments, the handle 2126 can be hollow. The outer handle portion 2127 can form an internal cavity, which can be filled with air, one or more other gasses, a partial vacuum, etc. The inner surface 2107 of the outer handle portion 2127 can be reflective. For the example, the inner surface 2107 can include a metal or other reflective material. In some embodiments, the outer handle portion 2127 can be made of a reflective material (e.g., a metal). In some embodiments the inner surface 2107 can be covered with the reflective material (e.g., a metal), and the outer handle portion 2127 can be made of a different material (e.g., a plastic) than the reflective inner surface 2107. The reflective material can be attached to the outer handle portion to form the inner surface 2107 by coating, plating, adhering, or any other suitable manner. The inner surface 2107 can be polished or can otherwise be sufficiently smooth to reflect light along the light pipe 2103 on the inside of the handle 2126. In some embodiments, the light pipe 2103 can be formed by the hollow interior of the outer handle portion.

In some embodiments, the light pipe can include a transparent material, such as glass, quartz, silica, a transparent plastic, acrylic (e.g., poly(methyl methacrylate)), or other solid transparent compounds. In some embodiments, the inner surface 2107 of the outer handle portion 2127 can include a reflective material, similar to the discussion of FIG. 22, and the reflective material can facilitate guiding of the light through the transparent material of the light pipe 2103.

In some embodiments, light can be guided along the light pipe 2103 by total internal reflection (TIR). In some embodiments, the outer handle portion 2127 can have a lower index of refraction than the transparent material of the light pipe 2103, such that light is guided along the light pipe 2103 by total internal reflection. The outer handle portion 2127 can be a cladding to cause total internal reflection of light in the light pipe 2103. The outer handle portion 2127 can be a transparent material or an opaque material. With reference to FIG. 23, a cladding material 2109 can be disposed between the light pipe 2103 and the outer handle portion 2127. The cladding material 2109 can have an index of refraction that is sufficiently lower than an index of refraction of the transparent material of the light pipe 2103 that the cladding material 2109 can function as a cladding so that light propagates along the light pipe 2103 by total internal reflection. The cladding material 2109 can be a solid transparent material (e.g., similar to the light pipe 2103, only having a lower index of refraction).

With reference to FIG. 24, in some embodiments, a gap 2111 is disposed between the outer handle portion 2127 and the light pipe 2103. The gap 2111 can have a material (e.g., air, one or more other gasses, a partial vacuum, etc.) that has an index of refraction that is sufficiently lower than the index of refraction of the transparent material of the light pipe 2103 that light propagates along the light pipe 2103 by total internal reflection. One or more offset structures 2113 can be positioned between the outer handle portion 2127 and the light pipe 2103 so offset the light pipe 2103 from the outer handle portion 2127 to form the gap 2111 therebetween. For example, the offset structures 2113 can include one or more posts, ridges, or other features, e.g., which can extend inwardly from the inner surface of the outer handle portion 2127. The light pipe 2103 can be contact the inward ends of the offset structures 2113 and can be held in place (e.g., by an adhesive, sonic welding, a friction fitting, a snap fitting, or any other suitable securement mechanism). In some embodiments, at least a portion of the light pipe 2103 can be removable from the handle 2126, and the light pipe 2103 can slide relative to the offset structures 2113.

In some example embodiments, a plurality of posts (e.g., as shown in FIG. 24) can extend between the outer handle portion 2127 and the light pipe 2103. The cross-sectional view of FIG. 24 shows four posts, although different configurations are possible. A cross-section of the handle 2126 can include one, two, three, four, or any suitable number of posts. Posts can be positioned at various locations along the longitudinal length of the light pipe, to facilitate the spacing of the light pipe 2103 from the outer handle portion 2127 to form the gap 2111. The offset structures 2113 can cover a relatively small portion of the outer surface of the light pipe 2103, so as to not interfere with the total internal reflection of light in the light pipe 2103, while also providing sufficient structural support to reliably provide the gap 2111. For example, the offset structures 2113 can cover between about 0.1% and about 10%, between about 0.5% and about 5%, between about 1% and about 2.5% of the outer surface of the light pipe 2103, although other values can be used, such as less than about 10%, less than about 7%, less than about 5%, less than about 3%, less than about 1%, or less (or any values or ranges therebetween) of the outer surface of the light pipe 2103.

In some embodiments, the outer handle portion 2127 can be omitted. For example, the light pipe 2103 can be exposed to the air of the environment surrounding the gonioscope 2125. The light pipe 2103 can be made of a rigid material. For example, a user can grip the light pipe 2103 directly to use the light pipe 2103 as a handle to hold the gonioscope 2125. In some embodiments, the light pipe 2103 can include one or more grip portions disposed over the light pipe so that the user can grip the grip portions without directly touching the light pipe 2103. The one or more grip portions can cover relatively little of the light pipe 2103 so as to minimize interfere with the guiding of the light while also providing enough space for the user to grip the gonioscope 2125. The one or more grip portions can cover between about 1% and about 25%, although other values can be used, such as less than about 25%, less than about 20%, less than about 15%, less than about 10%, less than about 5%, or less (or any values or ranges therebetween) of the outer surface of the light pipe 2103.

In the example embodiment shown in FIG. 21, the light pipe 2103 can include a covered portion 2103*a* that is covered by the outer handle portion 2127, and/or the light pipe 2103 can include an uncovered portion 2103*b* that is not covered by the outer handle portion 2127. The uncovered portion 2103*b* can be exposed (e.g., to air or the environment outside the gonioscope 2125). In some embodiments, the light pipe 2103 can be covered by the outer handle portion 2127 along the full length thereof. For example, the uncovered portion 2103*b* can be omitted. The gonioscope 2125 can be similar to the example embodiment shown in FIG. 21, except that the outer handle portion 2127 can extend to the gonioscopic optical element 2128 or to the handle attachment element 2129.

Figure 25:
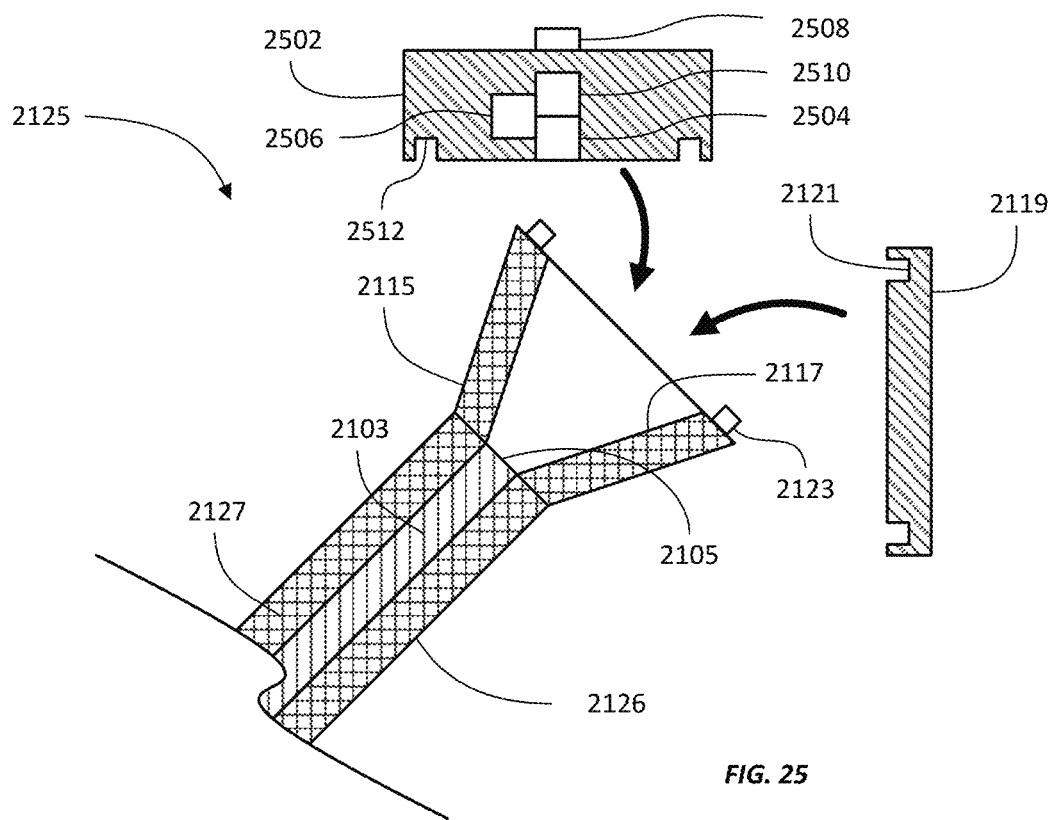
FIG. 25 is a cross-sectional view of an example embodiment of the proximal end of a gonioscope having a light pipe.

FIG. 25 shows a cross-sectional view of the proximal end of an example embodiment of a gonioscope 2125. The gonioscope 2125 can have a light collector 2115 (e.g., at the proximal end of the gonioscope 2125) that can be configured to direct light into the light pipe 2103. The light collector 2115 can have an input end (e.g., at the proximal end thereof) that is wider than an output end (e.g., at the distal end thereof). The output end can be configured to direct collected light into the light inlet 2105 of the light pipe 2103 so that the light propagates along the light pipe 2103. In some embodiments, the output end of the light collector can be coextensive with and/or adjacent to the light inlet 2105 of the light pipe 2103. The light collector 2115 can be generally conical or generally frustoconical in shape. The inner surface 2117 of the light collector 2115 can be reflective. For the example, the inner surface 2117 can include a metal or other reflective material. In some embodiments, the light collector 2115 can be made of a reflective material (e.g., a metal), which in some embodiments can be the same material as the outer handle portion 2127. In some embodiments the inner surface 2117 can be covered with the reflective material (e.g., a metal), and the body of the light collector 2115 can be made of a different material (e.g., a plastic) than the reflective inner surface 2117. The reflective material can be attached to the light collector 2115 body to form the reflective inner surface 2117 by coating, plating, adhering, or any other suitable manner. The inner surface 2117 can be polished or can otherwise be sufficiently smooth to reflect light so as to collect light to be directed along the light pipe 2103. In some embodiments, the inside of the light collector 2115 can be empty (e.g., filled with air). In some embodiments, the inside of the light collector 2115 can be filled with a transparent material (e.g., the same material as the light pipe 2103). In some embodiments, the light pipe 2103 can extend into the light collector 2115 so that a portion of the light pipe 2103 is configured to collect light (e.g., by having a light inlet 2105 that is wider than the shaft of the light pipe 2103).

In some embodiments, the gonioscope 2125 can include a removable cap 2119 that can be configured to cover the light inlet 2105 to impede light from entering the light pipe 2103 when the cap 2119 is attached to the gonioscope 2125. The cap 2119 can cover the input end of the light collector 2115, for example. In some embodiments, the light collector 2115 can be omitted, and the cap 2119 can attach to the handle 2126 (e.g., at the proximal end thereof). The cap 2119 can have side walls and can slip over the proximal end of the handle 2126. The cap 2119 can include one or more engagement features 2121, which can be configured to interface with one or more corresponding engagement features 2123 on the gonioscope 2125 to couple the cap 2119 to the gonioscope 2125. The engagement features 2121 and 2123 can be configured to disengage to enable removal of the cap 2119. The cap 2119 can be removed to enable light to enter the light pipe 2103 (e.g., for illuminating the eye as discussed herein). The engagement features 2121 and/or 2123 can include one or more clips, snap-fit features, clamps, friction-fit features, screw threading, or any other attachment mechanism. The cap 2119 can be attached to impede light from entering the light pipe 2103 (e.g., so that light from the light pipe 2103 does not illuminate the eye, as discussed herein).

In some embodiments, a removable lighting assembly 2502 can be removably coupled to the gonioscope. The lighting assembly 2502 can be used with the light collector 2115 (as shown for example if FIG. 25) or without the light collector 2115. The lighting assembly 2502 can include a light source 2504, which can be configured to input light into the light pipe 2103 (e.g., via the light inlet 2105). The light source 2504 can include one or more light emitting diodes (LEDs) or any other suitable type of light emitter. The lighting assembly 2502 can include a power source 2506 (e.g., a battery), which can be configured to provide electrical power to the light source 2504. In some embodiments, the lighting assembly housing can open to provide access to the power source 2506 and/or light source 2504 (e.g., to replace a battery or light emitter). The lighting assembly 2502 can include a user interface 2508, which can have one or more user input elements to receive input from a user (e.g., to control the light source 2504). The one or more user input elements can include one or more buttons, switches, dials, a touchscreen, or any other suitable device configured to receive input from a user. A controller 2510 can be configured to receive input from the user interface 2508 and can control the light source 2504 based on the received input. For example, user interface 2508 can be configured to receive input from the user to turn the light source 2504 on or off, and/or to change a brightness of the light source 2504, and light source 2504 can be responsive to the input (e.g., via the controller 2510) to perform the corresponding action, such as to turn on, to turn on, and/or to change the brightness. In some embodiments, the light source 2504 can include light emitters of different colors and the user interface 2508 can be configured to receive input from a user to select or change a color of the light emitted by the light source 2504. The lighting assembly 2502 can include one or more engagement features 2512 which can be configured to engage corresponding one or more engagement features 2123 on the gonioscope 2125 to couple the lighting assembly 2502 to the gonioscope 2125. The engagement features 2512 and 2123 can disengage to enable the lighting assembly 2502 to be removed from the gonioscope 2125. The engagement features 2512 and/or 2123 can include one or more clips, snap-fit features, clamps, friction-fit features, screw threading, or any other attachment mechanism. In some embodiments, the gonioscope 2125 can be disposable, and the lighting assembly 2502 can be removable from the gonioscope 2125 so that the lighting assembly 2502 can be reused with multiple disposable gonioscopes 2125. In some embodiments, the lighting assembly 2502 can be removed from a reusable gonioscope 2125 after use, such as when the gonioscope 2125 is to be cleaned and/or sterilized, and the lighting assembly 2502 can be reattached to the gonioscope 2125 for a later use after cleaning and/or sterilization. Although FIG. 25 shows the light collector 2115, the cap 2119, and the lighting assembly 2502, those features can be used independent of each other, or in any combination or subcombination, and/or together with other features disclosed herein.

Figure 26:
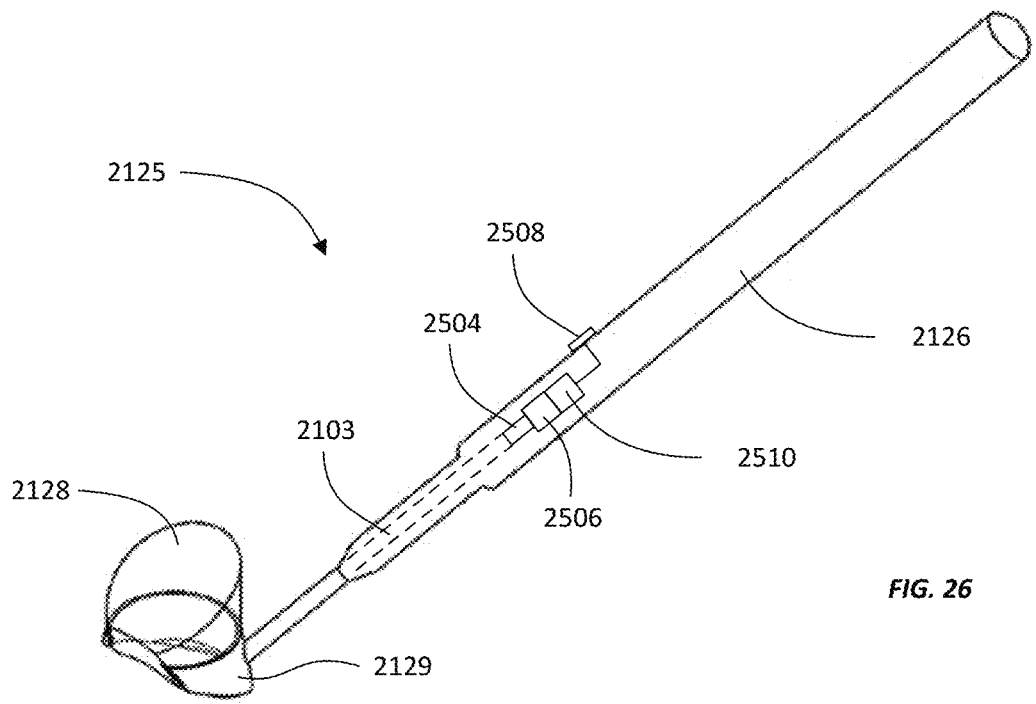
FIG. 26 shows an example embodiment of a gonioscope that includes a lighting assembly.

With reference to FIG. 26, in some embodiments, a light assembly (e.g., having features similar to the removable lighting assembly 2502 shown in FIG. 25) can be incorporated into the gonioscope 2125 (e.g., into the handle 2126 of the gonioscope). The light source 2504 can be disposed inside the handle 2506, and the light source 2504 can be configured to input light into a light pipe 2103, which can extend along at least a portion of the handle 2126 toward the gonioscopic optical element 2128, as discussed herein. A power source 2506 (e.g., a battery) can supply electrical power to the light source 2504, and can be disposed inside the handle 2126. In some embodiments, the handle 2126 can be configured to provide access to the power source 2506 and/or light source 2504 (e.g., to replace a battery or light emitter). For example, the handle 2126 can open or separate to provide access to the inside of the handle 2126. The user interface can be disposed on an outside of the handle 2126 to enable a user to control the light source 2504, as discussed herein. A controller 2510 can be disposed inside the handle 2126 and can be configured to control the light source 2504 in response to input received by the user interface 2508, as discussed herein.

Figure 27:
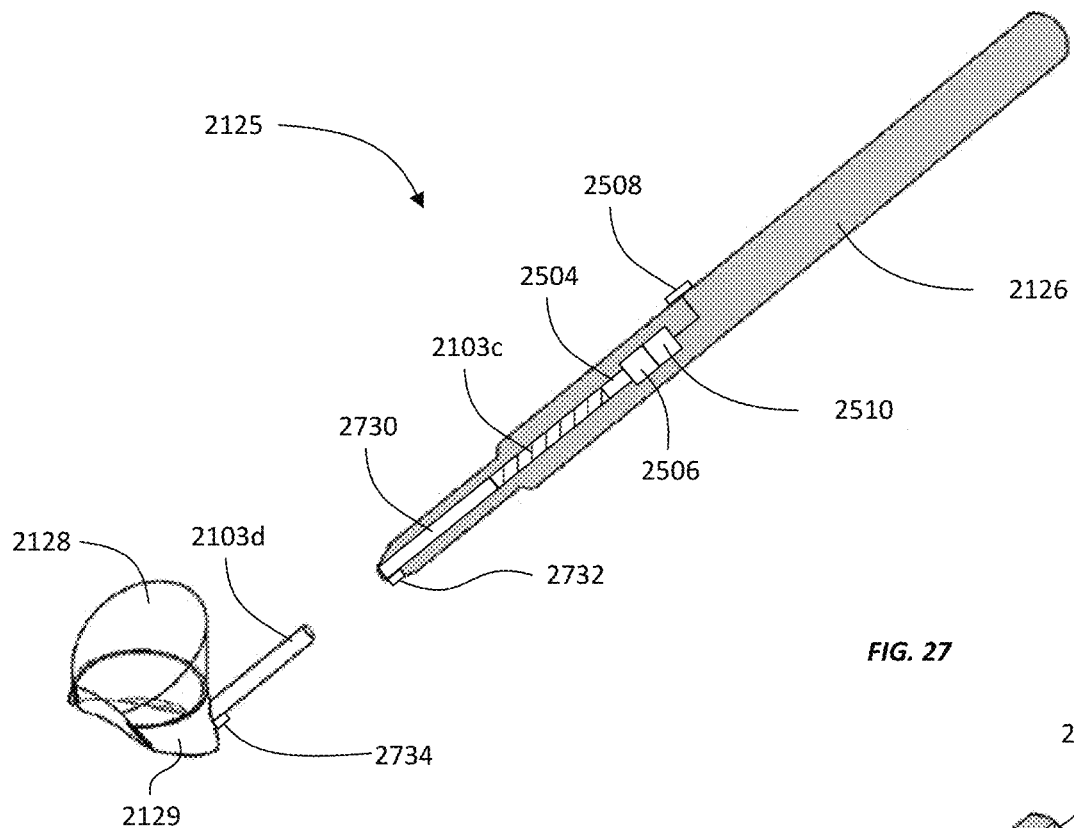
FIG. 27 shows an example embodiment of a gonioscope that includes a lighting assembly in a removable handle.

With reference to FIG. 27, in some embodiments, the handle 2126 of the gonioscope 2125 can be removable. The handle 2126 can include the lighting assembly elements, for example, as discussed in connection with FIG. 26. For example, handle can include a light source 2504, a power source 2504, a controller 2510, and/or a user interface 2508. Accordingly, the handle 2126 can be the removable lighting assembly 2502. The handle can include a first light guide portion 2103c, which can be configured to receive light from the light source 2504 and guide the received light along the handle 2126. The handle 2126 can include a recess 2730 configured to receive a second light guide portion 2103d therein. The second light guide portion 2103d can be configured to receive light from the first light guide portion 2103c when the handle 2126 is attached, and to direct the light into the eye (e.g., through the gonioscopic optical element 2128). When the handle 2126 is attached, the first light pipe portion 2103c and be optically coupled to the second light guide portion 2103d. In some implementations an index matching gel can be disposed between the ends of the first and second light guide portions 2103c and 2103d to facilitate the transition of light from the first light guide portion 2103c to the second light guide portion 2103d.

The handle 2126 can include one or more engagement features 2732, which can be configured to engage corresponding one or more engagement features 2734 on the gonioscope 2125 (e.g., on the gonioscopic optical element 2128 or on the handle attachment element 2129) to couple the handle 2126 to the rest of the gonioscope 2125 (e.g., to the gonioscopic optical element 2128). The engagement features 2732 and 2734 can disengage to enable the handle 2126 to be removed from the rest of the gonioscope 2125 (e.g., from the gonioscopic optical element 2128). The engagement features 2732 and/or 2734 can include one or more clips, snap-fit features, clamps, friction-fit features, screw threading, or any other attachment mechanism. In some embodiments, the second light guide portion 2103d inserting into the recess 2730 of the handle 2126 can provide the coupling mechanism (e.g., to couple the handle 2126 to the gonioscopic optical elements 2128). In some embodiments, the dedicated engagement features 2732 and 2734 can be omitted.

In some embodiments, the gonioscopic optical element 2128 and the first light guide portion 2103d can be integrally formed of the same material. In some embodiments, the gonioscopic optical element 2128 and the first light guide portion 2103d can be disposable, and the removable handle 2126 (e.g., including the lighting assembly and the second light pipe portion 2103c) can be reusable.

Figure 28:
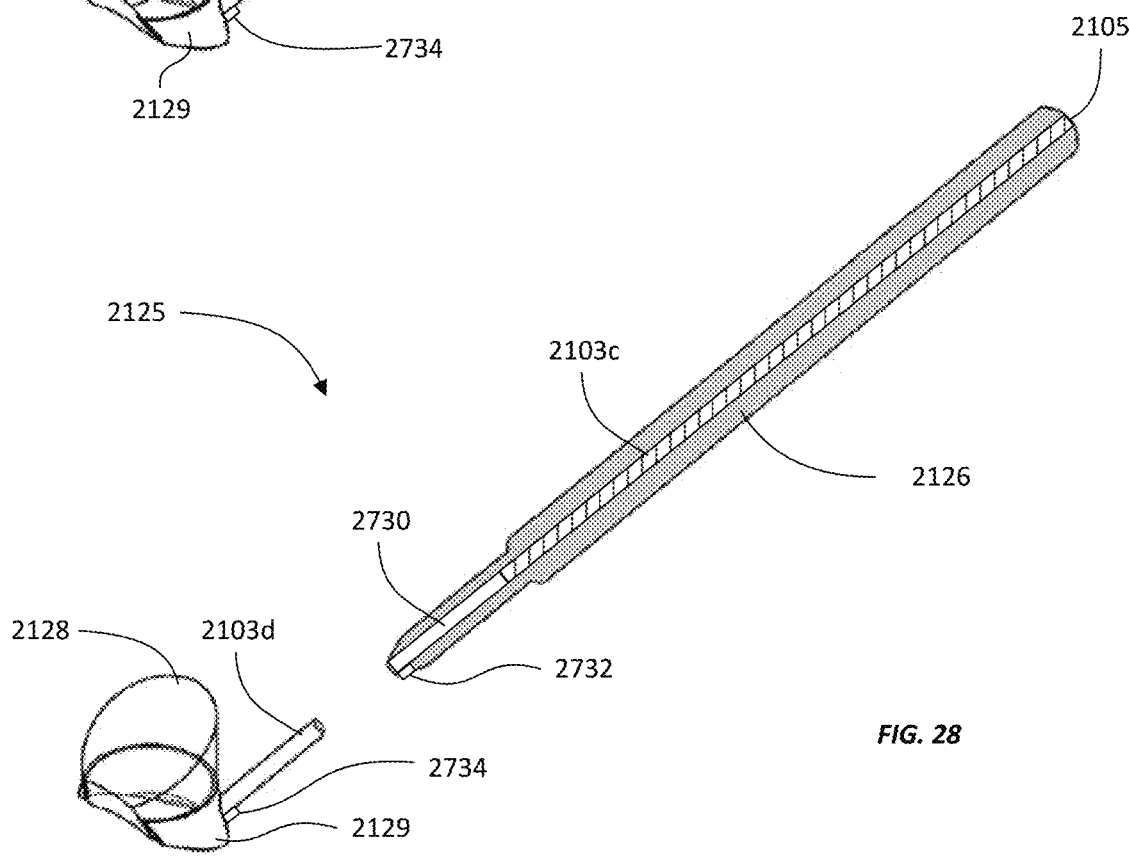
FIG. 28 shows an example embodiment of a gonioscope that includes a light pipe in a removable handle.

Many variations are possible. With reference to FIG. 28, in some embodiments, the removable handle 2126 does not include a lighting assembly. The first light pipe portion 2103c can extend to a light inlet 2105 (e.g., positioned at the proximal end of the handle 2126). Many variations are possible, and various features disclosed in connection with one embodiment can be combined with other embodiments disclosed herein.

Figure 29:
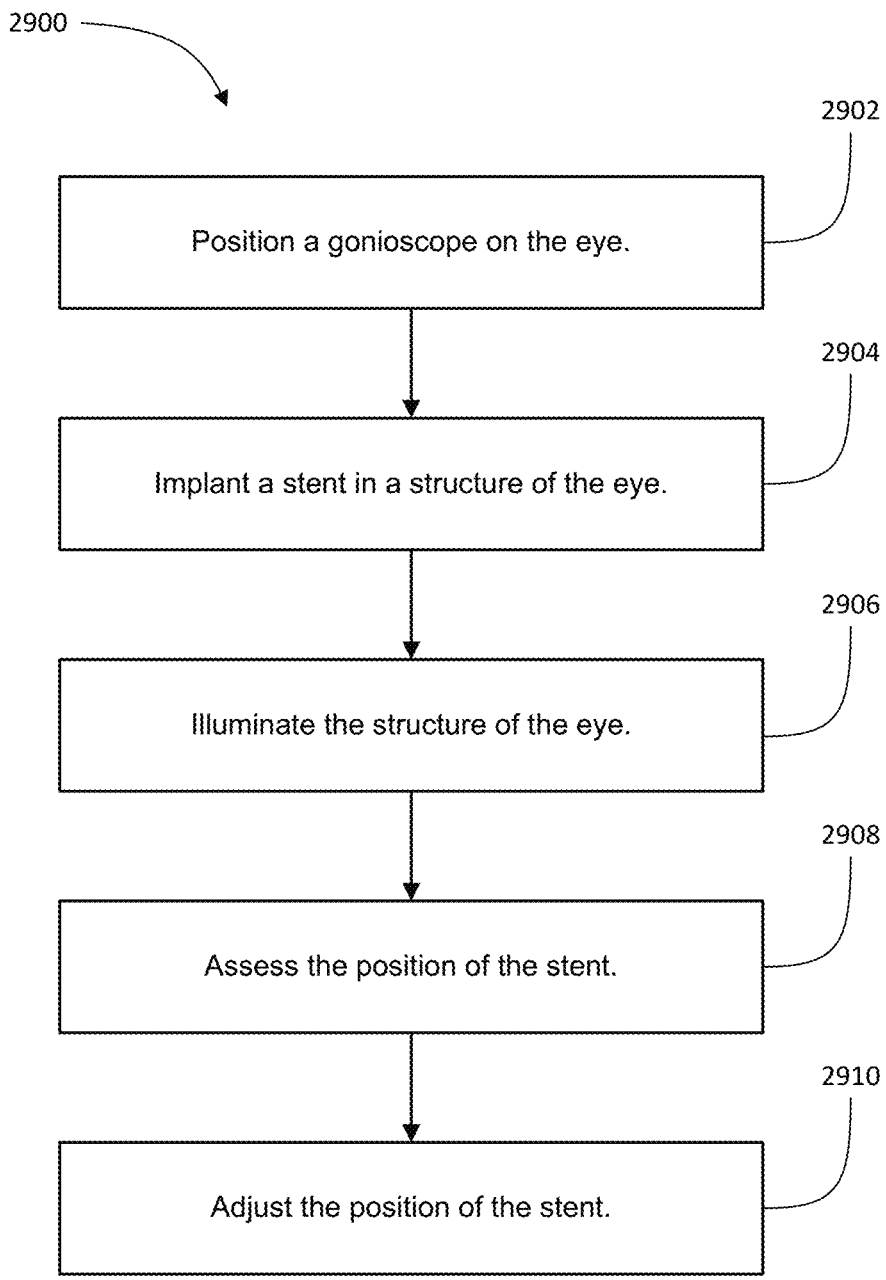
FIG. 29 shows a flowchart of an example embodiment of a method for assessing the position of a stent in an eye.
Figure 30:
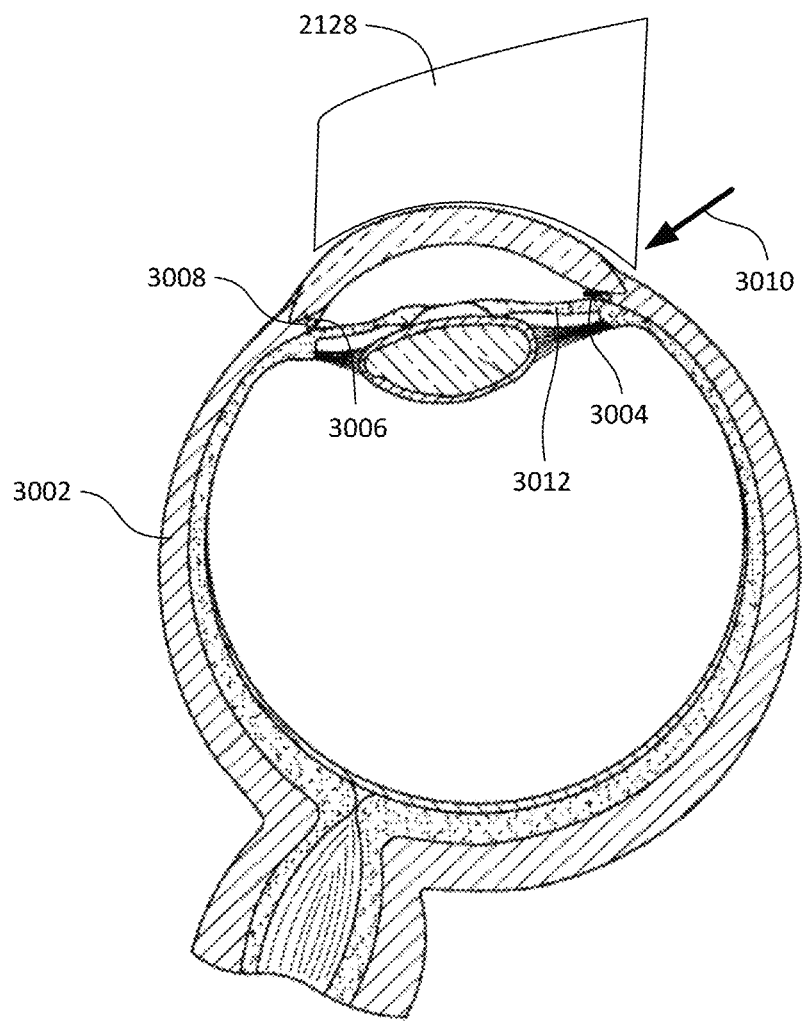
FIG. 30 shows an example embodiment of light directed into an eye for illuminating a stent to facilitate assessment of the position of the stent.

FIG. 29 is a flowchart showing an example embodiment of a method 2900 for assessing the position of a stent in the eye of a patient. At block 2902 a user can position a gonioscope on the eye, for example to view structures within the eye. Various gonioscopes and figures disclosed herein can be used to implement the method 2900. FIG. 30 shows a gonioscopic optical element 2128 positioned on an eye 3002. The other features of the gonioscope are omitted from view in FIG. 30, for ease of illustration. At block 2904, the user can implant a stent 3004 in a structure of the eye. For example, a stent can be implanted into the trabecular meshwork 3006. A stent 3004 can be implanted to facilitate flow of aqueous humor from the anterior chamber through the stent into Schlemm's canal 3008. The gonioscope can facilitate viewing of the structure inside the eye during implanting of the stent. Various features and details relating to stents and implantation of stents into the eye are disclosed in U.S. Patent Application Publication No. 2015/0342875, the entirety of which is hereby incorporated by reference herein.

At block 2906, the user can illuminate the structure of the eye where the stent 3004 was implanted. In some implementations, transillumination and/or retroillumination can be used at block 2906 to illuminate the structure of the eye. By way of example, light can be directed through the tissue of the eye and can produce a silhouette of the stent 3004 in the structure of the eye. Light 3010 be directed to the eye by the gonioscope 2125 (e.g., such as the example embodiments of FIGS. 21-28). For example, light 3010 can be guided along a light pipe 2013 in a handle 2126 of the gonioscope 2125. In some embodiments, light 3010 can be directed through the gonioscopic optical element 2128 to the eye 3002. The light 3010 can enter the eye on the side of the eye where the stent 2004 was implanted. The light 3010 can enter the eye through the scleral tissue and/or through the cornea tissue. The light 3010 can reflect and/or scatter off of structure in the eye, such as the iris 3012 of the eye, the trabecular meshwork 3006, the structure into which the stent 3004 is inserted, etc. The reflected and/or scattered light can exit the eye (e.g., via the gonioscopic optical element 2128) and can be viewed by the user.

At block 2908, the user can assess the position of the stent 3004. For example, the user can view the position of the stent 3004 relative to the structure of the eye to evaluate whether the stent 3004 is positioned properly. By way of example, if a stent 3004 is over inserted too far, the trabecular meshwork can occlude, or otherwise impede fluid flow into, a fluid inlet on the stent 3004.

At block 2910, the user can adjust the position of the stent 3004. In some embodiments, the user can remove the stent 3004 from the 3002. In some embodiments, the user can remove the stent 3004 and then redo the implantation of the stent 3004 into the eye. In some embodiments, the user can leave the stent 3004 implanted and the user can retract the stent 3004 to an appropriate position.

Many variations are possible. For example, in some instances, the stent 3004 may not require adjustment and block 2910 can be omitted. In some embodiments, light 3010 can be directed into the eye 3002 from a light source that is not associated with the gonioscope. For example, a flashlight or other light source can be positioned close to the eye to direct the light 3010 into the eye 3002.

The embodiments discussed herein are provided by way of example, and various modifications can be made to the embodiments described herein. Certain features that are described in this disclosure in the context of separate embodiments can also be implemented in combination in a single embodiment. Conversely, various features that are described in the context of a single embodiment can be implemented in multiple embodiments separately or in various suitable subcombinations. Also, features described in connection with one combination can be excised from that combination and can be combined with other features in various combinations and subcombinations. Various features can be added to the example embodiments disclosed herein. Also, various features can be omitted from the example embodiments disclosed herein. As used herein the term "comprises" and its variants are used as open-ended terms. For example, the phrase "A comprises B" should be understood to mean that A includes B, and that A may include additional features, elements, etc. in addition to B. Various example claims are provided below reciting various different combinations of features. Various additional combinations of features are also contemplated, as described herein and as would be understood to the skilled artisan.

What is claimed is:

1. A gonioscope comprising:
a gonioscopic optical element that includes:
a concave distal surface configured to be positioned on an eye of a subject; and
a proximal surface, wherein the gonioscopic optical element is configured to receive light from a structure inside the eye through the distal surface, and to output the light from the proximal surface to produce an image of the structure inside the eye, and wherein the proximal surface is angled relative to the distal surface so that a distance between the proximal surface and the distal surface on a first side of the gonioscopic optical element is smaller than a distance between the proximal surface and the distal surface on a second side of the gonioscopic optical element;
a handle coupled to the gonioscopic optical element, wherein the gonioscopic optical element has a plane of symmetry, and wherein the handle has a centered position with the handle extending generally upward from the gonioscopic optical element along the plane of symmetry; and
a plurality of arms extending distally from the gonioscopic optical element, wherein the plurality of arms have retention elements configured to engage scleral tissue of the eye to retain the gonioscope relative to the eye.

2. The gonioscope of claim 1, wherein the handle is removable from the gonioscopic optical element.

3. The gonioscope of claim 1, further comprising an optical fixation point.

4. The gonioscope of claim 3, wherein the optical fixation point is configured to be visible to the subject when the gonioscopic optical element is positioned over the eye of the subject, wherein the optical fixation point is configured so that when the eye of the subject looks directly at the optical fixation point, the gonioscopic optical element is oriented relative to the eye so that the light output from the proximal surface of the gonioscopic optical element produces an image of the anterior chamber angle of the eye.

5. The gonioscope of claim 1, wherein the plurality of arms includes a first arm having a centered position that extends along the plane of symmetry of the gonioscopic optical element, a second arm positioned on a left side of the gonioscopic optical element, and a third arm positioned on a right side of the gonioscopic optical element.

6. The gonioscope of claim 5, wherein the first arm includes a plurality of the retention elements that comprise protrusions, wherein the second arm includes a plurality of the retention elements that comprise protrusions, and wherein the third arm includes a plurality of the retention elements that comprise protrusions.

7. The gonioscope of claim 1, wherein the retention elements comprise protrusions.

8. The gonioscope of claim 1, wherein the proximal surface of the gonioscopic optical element is curved.

9. The gonioscope of claim 1, wherein the handle has a distal portion having a first thickness and a proximal portion having a second thickness that is larger than the first thickness.

10. A gonioscope comprising:
- a gonioscopic optical element having a concave distal surface and a proximal surface, wherein the gonioscopic optical element is configured to be positioned over an eye of a subject for imaging a structure inside the eye;
- a handle coupled to the gonioscopic optical element, wherein the handle has a centered position with the handle extending generally proximally from the gonioscopic optical element; and
- a plurality of arms extending distally from the gonioscopic optical element, wherein the plurality of arms have retention elements configured to engage scleral tissue of the eye to retain the gonioscope relative to the eye.

11. The gonioscope of claim 10, wherein the handle is removable from the gonioscopic optical element.

12. The gonioscope of claim 10, further comprising an optical fixation point.

13. The gonioscope of claim 12, wherein the optical fixation point is configured to be visible to the subject when the gonioscopic optical element is positioned over the eye of the subject, wherein the optical fixation point is configured so that when the eye of the subject looks directly at the optical fixation point, the gonioscopic optical element is oriented relative to the eye so that light output from the proximal surface of the gonioscopic optical element produces an image of the anterior chamber angle of the eye.

14. The gonioscope of claim 10, wherein the plurality of arms includes a first arm having a centered position that extends along the plane of symmetry of the gonioscopic optical element, a second arm positioned on a left side of the gonioscopic optical element, and a third arm positioned on a right side of the gonioscopic optical element.

15. The gonioscope of claim 14, wherein the retention elements comprise protrusions, wherein the first arm includes one or more of the protrusions, wherein the second arm includes one or more of the protrusions, and wherein the third arm includes one or more of the protrusions.

16. The gonioscope of claim 10, wherein the retention elements comprise protrusions.

17. The gonioscope of claim 10, wherein the proximal surface of the gonioscopic optical element is curved.

18. The gonioscope of claim 10, wherein the handle has a distal portion having a first thickness and a proximal portion having a second thickness that is larger than the first thickness.

19. The gonioscope of claim 10, wherein the proximal surface of the gonioscopic optical element is angled relative to the distal surface so that a distance between the proximal surface and the distal surface on a first side of the gonioscopic optical element is smaller than a distance between the proximal surface and the distal surface on a second side of the gonioscopic optical element.

20. The gonioscope of claim 10, wherein the gonioscopic optical element has a shape with a single plane of symmetry, and handle extends along the plane of symmetry.

* * * * *